(12) United States Patent
Wimpenny et al.

(10) Patent No.: US 12,138,430 B2
(45) Date of Patent: Nov. 12, 2024

(54) DRUG DELIVERY DEVICES

(71) Applicant: Sanofi, Paris (FR)

(72) Inventors: Steven Wimpenny, Warwick (GB);
David Aubrey Plumptre, Warwick (GB); Robert Veasey, Warwick (GB);
Ian McFaul, Warwick (GB); Hugh Smith, Warwick (GB); Paul Griffin, Warwick (GB)

(73) Assignee: Sanofi, Paris (FR)

( * ) Notice: Subject to any disclaimer, the term of this patent is extended or adjusted under 35 U.S.C. 154(b) by 871 days.

(21) Appl. No.: 17/259,617

(22) PCT Filed: Jul. 15, 2019

(86) PCT No.: PCT/EP2019/068974
§ 371 (c)(1),
(2) Date: Jan. 12, 2021

(87) PCT Pub. No.: WO2020/016165
PCT Pub. Date: Jan. 23, 2020

(65) Prior Publication Data
US 2021/0290850 A1    Sep. 23, 2021

(30) Foreign Application Priority Data

Jul. 18, 2018  (EP) .................................. 18305979

(51) Int. Cl.
*A61M 5/31* (2006.01)
*A61M 5/24* (2006.01)
*A61M 5/315* (2006.01)

(52) U.S. Cl.
CPC ................ *A61M 5/31* (2013.01); *A61M 5/24* (2013.01); *A61M 5/31548* (2013.01); *A61M 5/31568* (2013.01); *A61M 5/3157* (2013.01); *A61M 2205/581* (2013.01); *A61M 2205/582* (2013.01); *A61M 2207/00* (2013.01)

(58) Field of Classification Search
CPC ...... A61M 5/31; A61M 5/24; A61M 5/31548; A61M 5/31568; A61M 5/3157
See application file for complete search history.

(56) References Cited

U.S. PATENT DOCUMENTS

| 2,904,043 A | 9/1959 | Friedman |
| 2005/0171476 A1 | 8/2005 | Judson et al. |
| 2012/0143146 A1 | 6/2012 | Strehl et al. |
| 2013/0211377 A1 | 8/2013 | Butler et al. |

(Continued)

FOREIGN PATENT DOCUMENTS

| CN | 1780652 | 5/2006 |
| CN | 102245235 | 11/2011 |

(Continued)

OTHER PUBLICATIONS

PCT International Preliminary Report on Patentability in International Application No. PCT/EP2019/068974, dated Jan. 19, 2021, 7 pages.

(Continued)

*Primary Examiner* — Dung T Ulsh
(74) *Attorney, Agent, or Firm* — Fish & Richardson P.C.

(57) ABSTRACT

An arrangement of drug delivery devices is provided with interchangeable members and non-interchangeable members.

23 Claims, 28 Drawing Sheets

(56) References Cited

U.S. PATENT DOCUMENTS

| | | | |
|---|---|---|---|
| 2013/0310746 A1 | 11/2013 | Wozencroft | |
| 2016/0129196 A1 | 5/2016 | Hirschel et al. | |
| 2017/0000955 A1 | 1/2017 | McLoughlin et al. | |
| 2017/0312435 A1* | 11/2017 | Stefansen | A61M 5/2033 |
| 2018/0056009 A1 | 3/2018 | Filman et al. | |

FOREIGN PATENT DOCUMENTS

| | | |
|---|---|---|
| CN | 102458520 | 5/2012 |
| CN | 103313742 | 9/2013 |
| CN | 107206166 | 9/2017 |
| CN | 107789707 | 3/2018 |
| EP | 1423079 | 7/2006 |
| EP | 2043708 | 12/2010 |
| EP | 3290075 | 3/2018 |
| JP | 2006-519077 | 8/2006 |
| JP | 2014-503286 | 2/2014 |
| JP | 2015-526217 | 9/2015 |
| JP | 2017-527404 | 9/2017 |
| JP | 2017-533767 | 11/2017 |
| KR | 10-2012-0027291 A | 3/2012 |
| RU | 2648866 | 3/2018 |
| WO | WO 2004/078239 | 9/2004 |
| WO | WO 2004/078241 | 9/2004 |
| WO | WO 2010/043533 | 4/2010 |
| WO | WO 2010/139635 | 12/2010 |
| WO | WO 2011/032883 | 3/2011 |
| WO | WO 2012/064258 | 5/2012 |
| WO | WO 2012/085588 | 6/2012 |
| WO | WO 2012/130704 | 10/2012 |
| WO | WO 2014/033195 | 3/2014 |
| WO | WO 2016/042076 | 3/2016 |
| WO | WO 2016/065220 | 4/2016 |
| WO | WO 2016/075254 | 5/2016 |
| WO | WO 2016/091554 | 6/2016 |
| WO | WO 2016/150900 | 9/2016 |
| WO | WO 2017/186435 | 11/2017 |

OTHER PUBLICATIONS

PCT International Search Report and Written Opinion in International Application No. PCT/EP2019/068974, dated Sep. 30, 2019, 12 pages.

\* cited by examiner

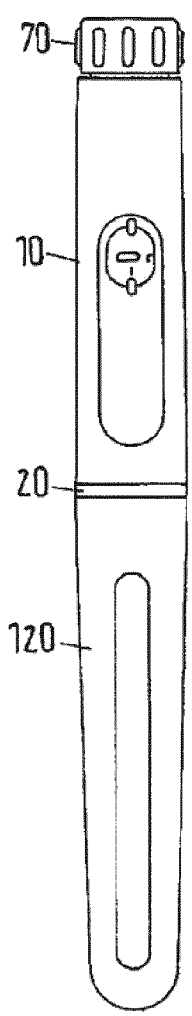
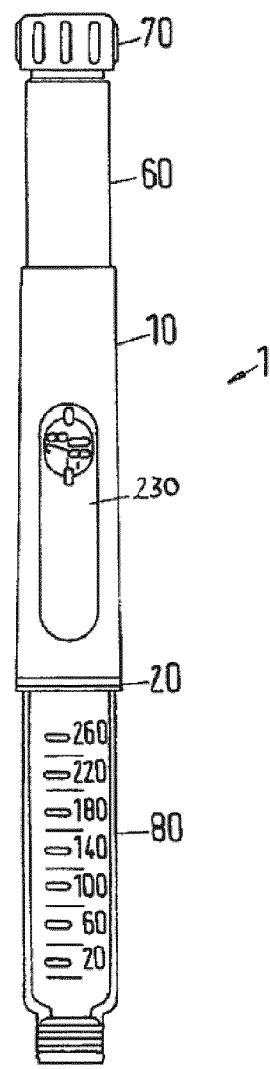

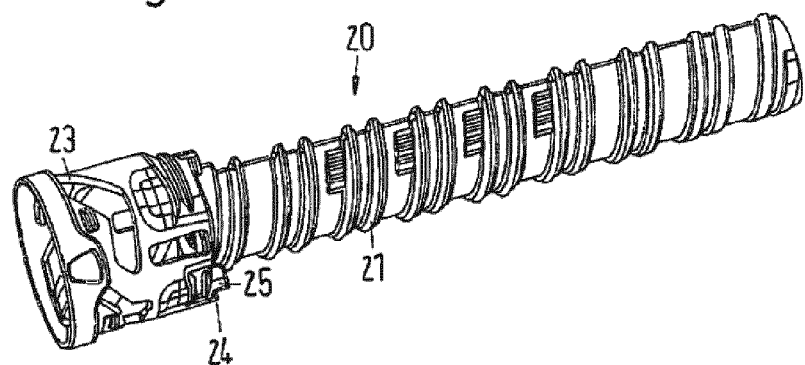
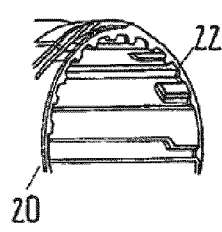
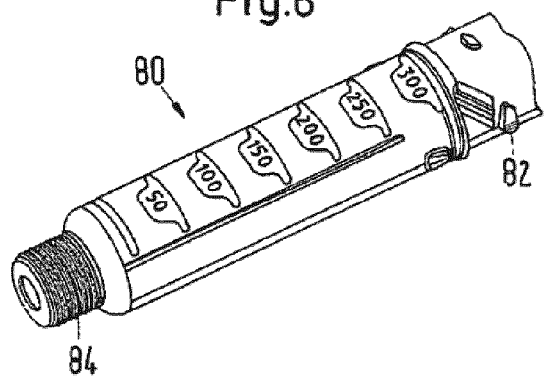
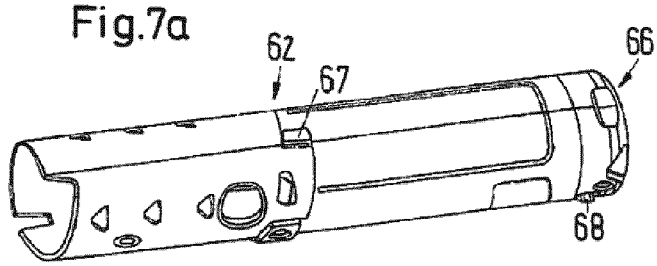
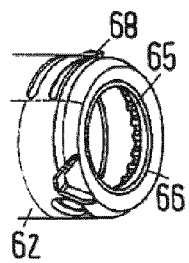

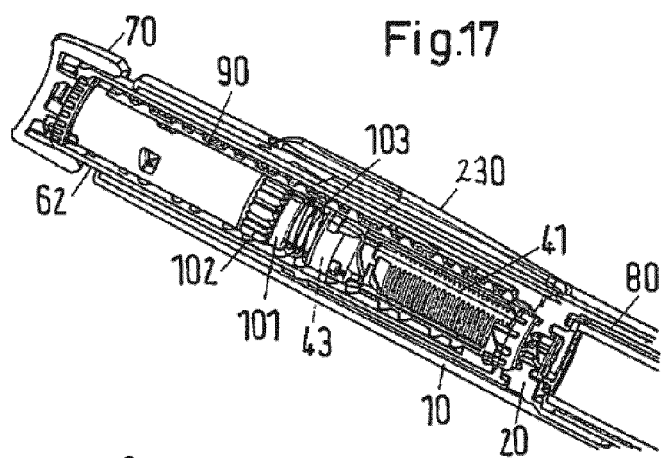
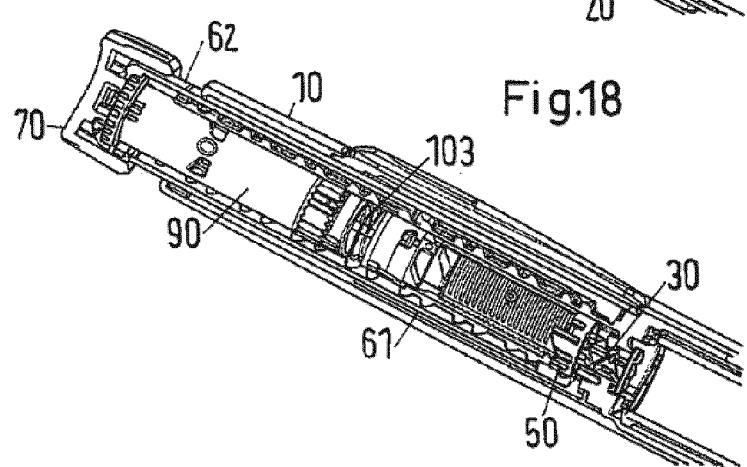
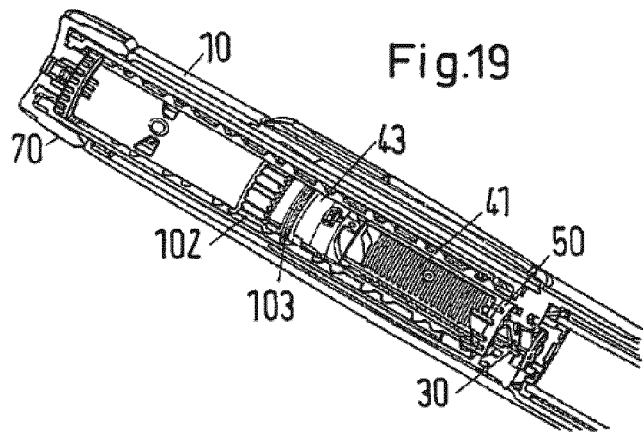

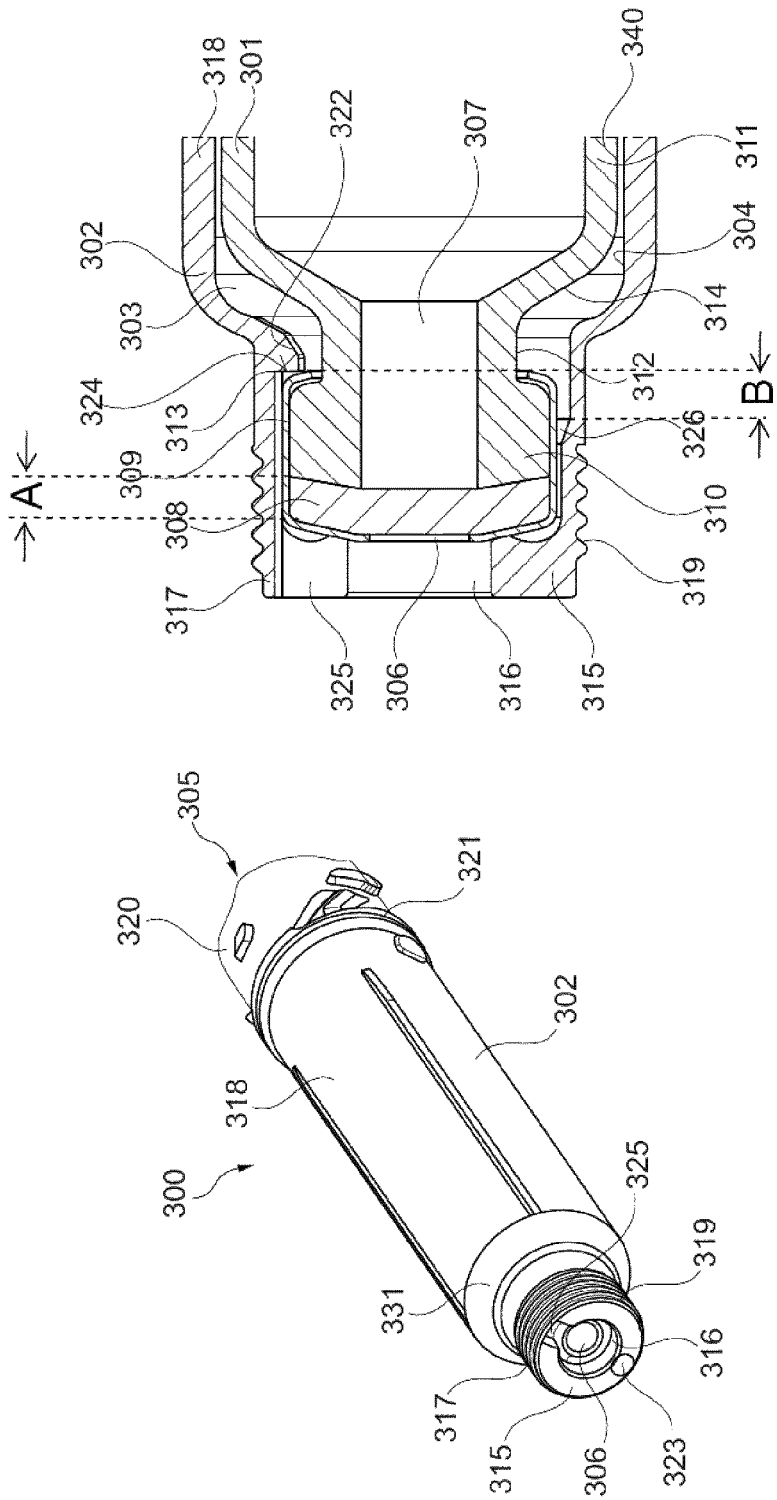

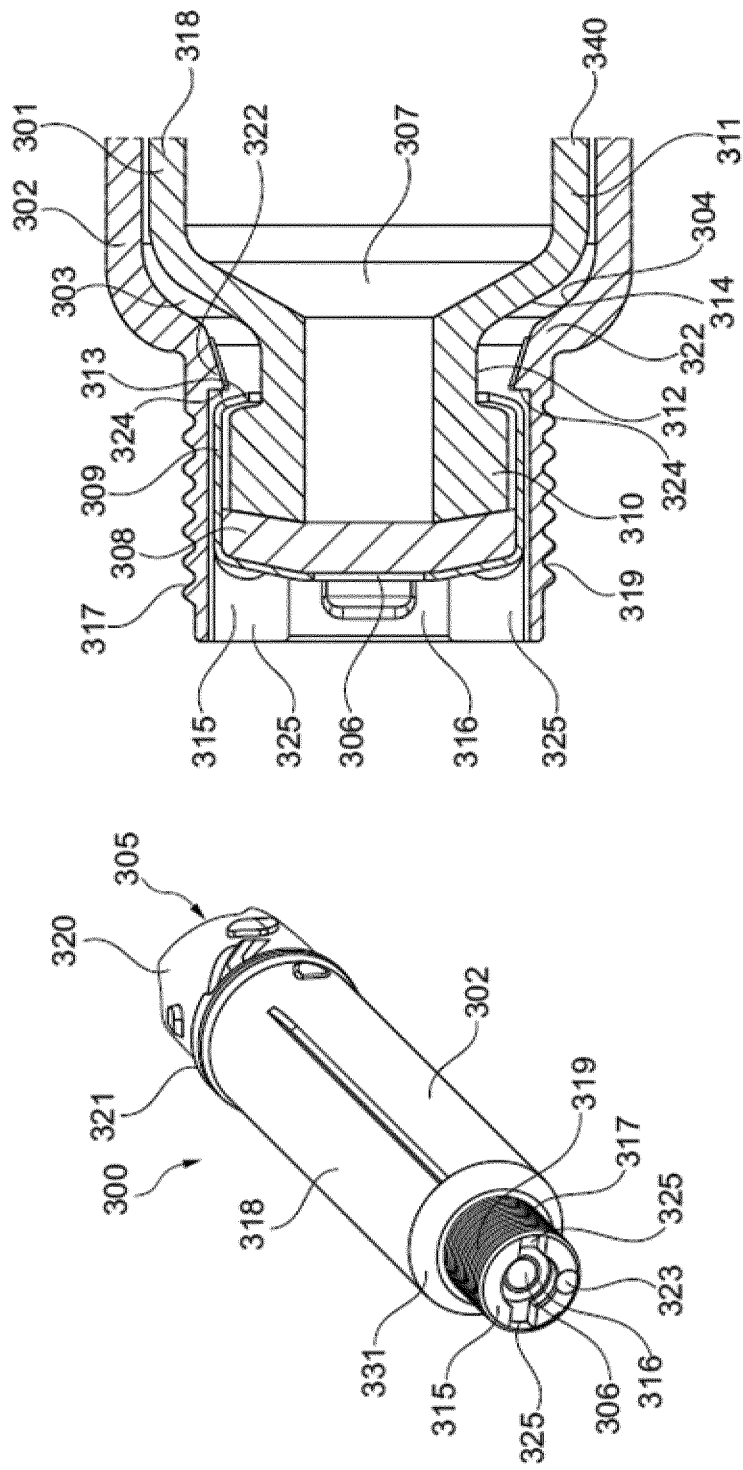

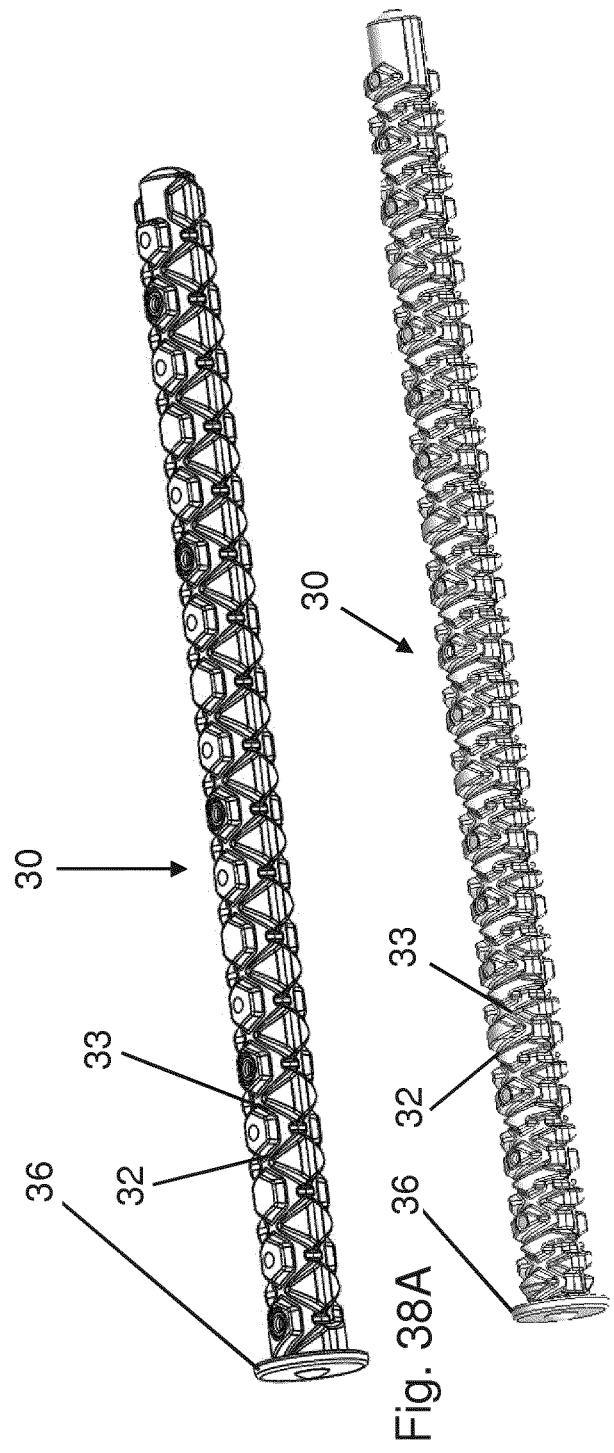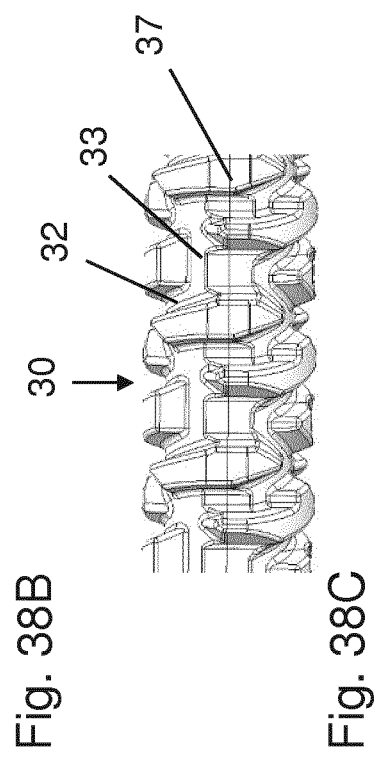
Fig. 38A
Fig. 38B
Fig. 38C

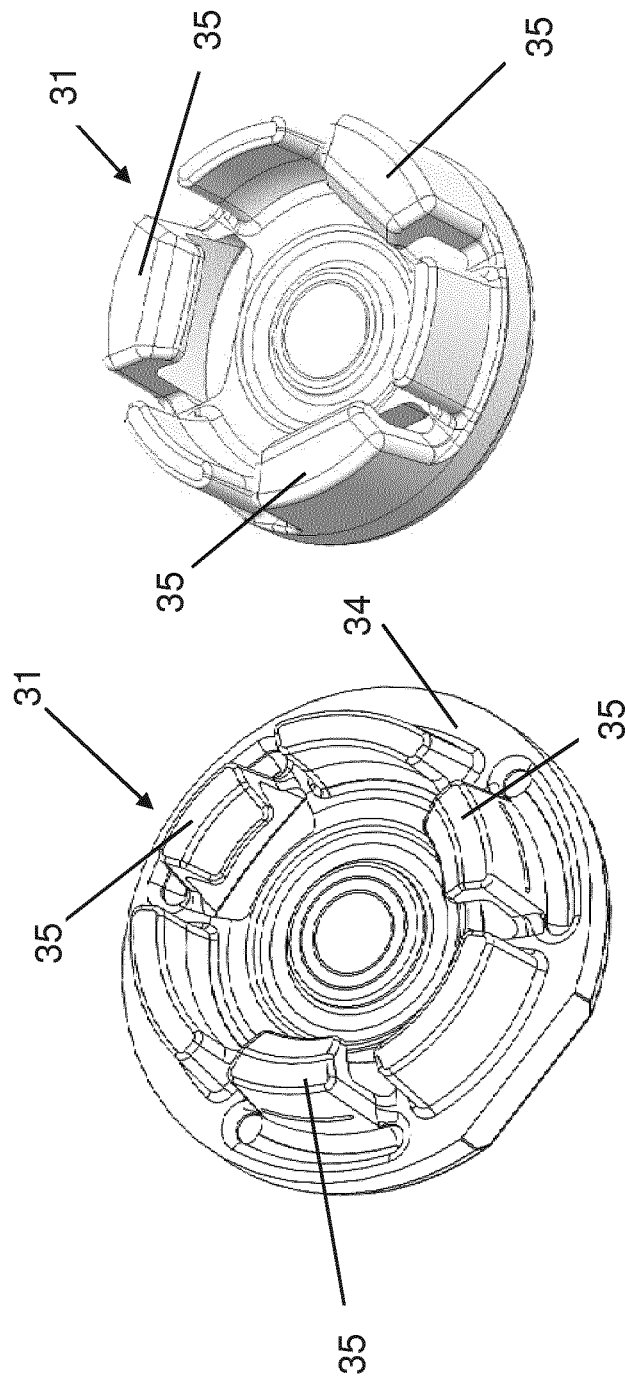

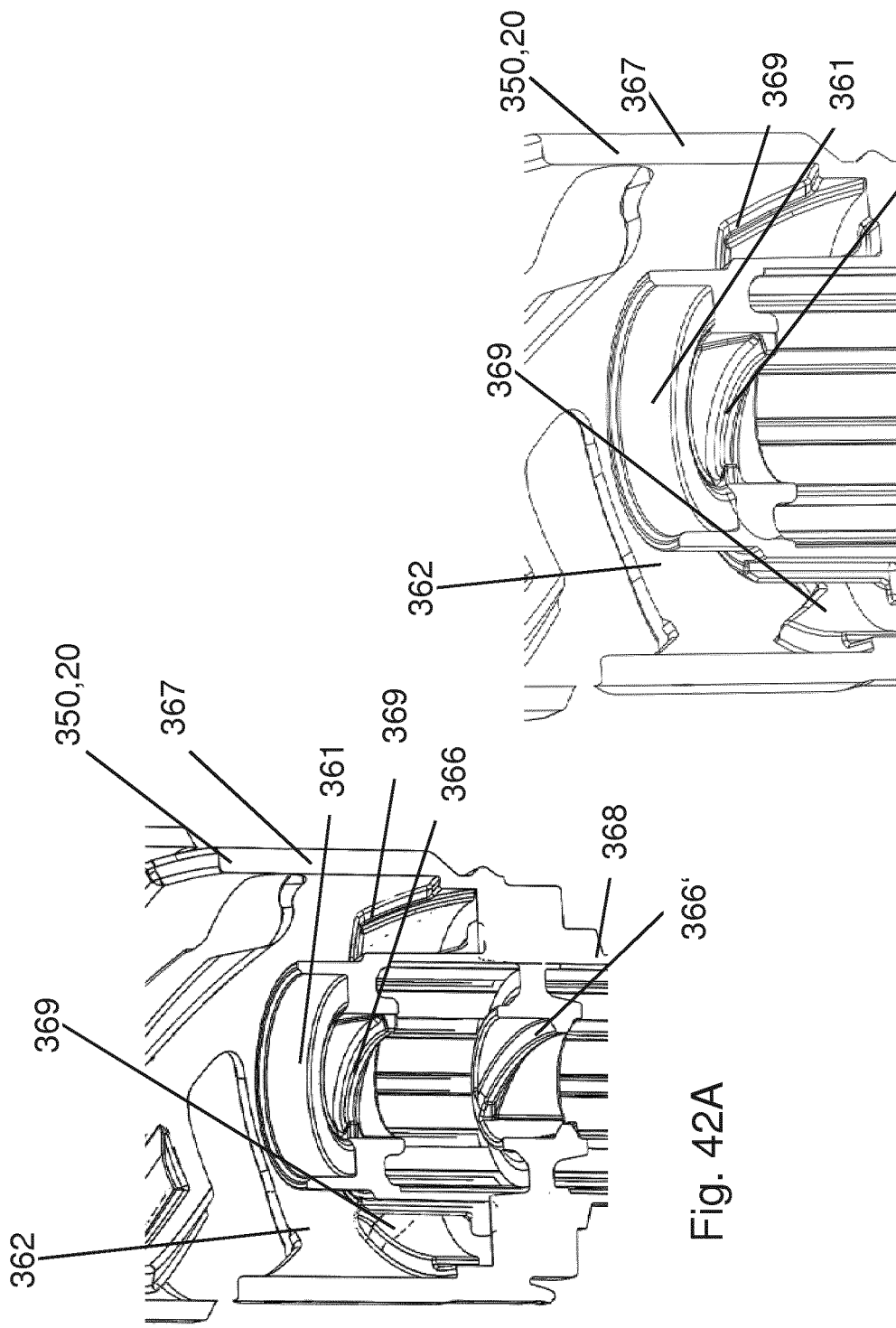

DRUG DELIVERY DEVICES

CROSS REFERENCE TO RELATED APPLICATIONS

The present application is the national stage entry of International Patent Application No. PCT/EP2019/068974, filed on Jul. 15, 2019, and claims priority to Application No. EP 18305979.9, filed on Jul. 18, 2018, the disclosures of which are incorporated herein by reference.

TECHNICAL FIELD

The present disclosure relates to a drug delivery device. Particularly, the present disclosure relates to an arrangement of drug delivery devices and/or to a method for the modification of one drug delivery device or parts thereof to provide a different drug delivery device. The respective drug delivery device is preferably an injection device and/or a pen-type device, such as a pen-type injector.

BACKGROUND

In recent times, drug delivery devices, e.g. the ones which are used by medically non-trained users such as patients, have become very sophisticated with respect to the mechanisms which they use for dose setting and/or dose delivery. Users have become very accustomed to the way specific drug delivery devices operate and got to know advantages of certain types of devices and their dose setting and drive mechanisms. It is also not unheard of that users of drug delivery devices told their friends of the specific advantages and the friends, who might suffer from a different disease than the user, want to try the device, which has been recommended by their friend, but with a different drug or drug formulation which suits the needs of the friend.

SUMMARY

Therefore, it is an object of the present disclosure to provide improvements associated with drug delivery devices, which are, preferably, modified for different purposes, e.g. for dispensing different drugs or drug formulations.

This object is achieved, for example, by the subject-matter defined in the independent claims and/or other subject-matter disclosed herein. Further advantageous solutions, embodiments and refinements are subject-matter of the dependent claims and/or of the following disclosure.

One aspect of the present disclosure relates to the drug delivery device. The drug delivery device, in the present disclosure, comprises a housing. The housing may have a proximal end and a distal end. The housing may have a tubular shape. The housing may define a section of the exterior shape or contour of the drug delivery device. The drug delivery device preferably further comprises a dose setting and drive mechanism. The dose setting and drive mechanism is expediently at least partly arranged in the housing. The dose setting and drive mechanism may comprise one or more mechanism members. The mechanism members are preferably movable relative to the housing and/or relative to one another during a dose setting operation and/or during a dose delivery operation. A dose setting operation may be an operation, where the size of a dose of liquid, which is to be dispensed from the drug delivery device is set. The size may be varied. Therefore, the drug delivery device may be a variable dose device. In the dose delivery operation, the previously set dose may be dispensed from the device.

A mechanism unit of the drug delivery device may comprise the housing and the dose setting and drive mechanism. The drug delivery device may be a resettable or reusable device. That is to say, after the content of a drug reservoir or cartridge has been emptied, the reservoir or cartridge may be replaced with a new reservoir or cartridge and the mechanism unit may be reused to dispense the drug from the new reservoir or cartridge. As opposed to the mechanism members, the housing may be static during the dose setting operation and the dose delivery operation, preferably also during a reset operation, when the mechanism is reset to an initial condition and ready to be used together with a new reservoir or cartridge. The respective mechanism member may move relative to the housing and/or relative to other mechanism members at least during the dose setting operation or the dose delivery operation or during both operations. The respective mechanism member may be static relative to the housing during only one of the dose setting operation and the dose delivery operation or move relative to the housing during the dose setting operation and the dose delivery operation.

The drug delivery device preferably comprises a cartridge unit, which is, preferably releasably or permanently, connected or connectable to the housing or retained in the housing. The cartridge unit may be configured to provide a cartridge and/or to connect the cartridge to the housing. The cartridge unit may comprise or may be provided to retain a cartridge containing a liquid, e.g. a drug or medicament. The cartridge may comprise a bung and a cartridge body. The bung may be movable in the distal direction relative to the cartridge body to dispense liquid from the cartridge. The liquid may be dispensed through a dispensing opening of the cartridge, which may be arranged at the distal end of the cartridge. The quantity of liquid in the cartridge may be sufficient for a plurality of doses to be dispensed form the drug delivery device. The dispensing opening may be closed by a septum, which may be pierced, e.g. by a needle, to provide fluid communication between the interior of the cartridge body and the exterior. The bung may seal the cartridge proximally. The cartridge unit may comprise a cartridge holder, in particular if the cartridge unit is connected to the housing either releasably or permanently, i.e. irreleasably. The cartridge may be arranged within the cartridge holder and preferably be retained therein. The cartridge may be permanently retained or secured in the cartridge holder. The cartridge holder may be releasably secured to the housing. If the cartridge is permanently secured in the cartridge holder, the cartridge unit may be a single disposable item or an item of consumable material, which is exchanged when the cartridge has been emptied. Thus, the cartridge may be protected by the cartridge holder all the time. Exchanging a cartridge within a cartridge holder can then be dispensed with. The entire cartridge unit may be disposed of after the cartridge has been emptied and replaced with a new cartridge unit. As an alternative to a cartridge unit which comprises the cartridge holder and the cartridge, the cartridge unit being connected to the housing, a cartridge retaining section may be defined in the housing, within which the cartridge unit, which then preferably consists of the cartridge, can be retained. If the housing has a cartridge retaining section in its interior, the housing may be unitary and/or may cover members of the dose setting and drive mechanism as well as the cartridge, the latter one preferably along its entire axial extension. The housing may have a generally tubular shape.

One aspect or the present disclosure relates to an arrangement of drug delivery devices. The arrangement comprises a first drug delivery device and a second drug delivery device. The arrangement may comprise further devices. The first and the second drug delivery device may have the features or parts discussed above, where the features or parts associated with the first device may be identified by the prefix "first" in the following text and in the claims and the features associated with the second drug delivery device may be identified by the prefix "second". Thus, the first drug delivery device comprises a first housing and the second drug delivery device comprises a second housing and so on. When a drug delivery device is generally discussed or the features of drug delivery devices are described in general the prefix is usually not used. In this case, the first and/or the second drug delivery device may comprise the associated features. When discussing differences between the first drug delivery device and the second drug delivery device the prefixes may be used.

In an embodiment, the first mechanism members and the second mechanism members, that is to say the mechanism members of the dose setting and drive mechanisms of the first and second drug delivery devices, comprise at least one interchangeable mechanism member, e.g. one or more. The interchangeable mechanism member may be a member, which can be used to assemble both, the first dose setting and drive mechanism and the second dose setting and drive mechanism. When a mechanism member is an interchangeable mechanism member, advantageously no structural modifications have to be made to the member to be applied in the first drug delivery device and in the second drug delivery device. Thus, an interchangeable mechanism member can be used in both devices, without structural modifications and/or without changing the operation characteristics of the respective device. Interchangeable members may be structurally identical. The first and the second drug delivery device, in particular the first and second dose setting and drive mechanisms, may nevertheless be different. Having interchangeable members or parts in different drug delivery devices makes production of drug delivery devices more economic, as one specific component can be used for different devices.

In an embodiment, the first mechanism members and the second mechanism members each comprise at least one non-interchangeable or unique mechanism member, e.g. one or more. As opposed to the interchangeable mechanism member, a non-interchangeable mechanism member of one dose setting and drive mechanism cannot be used to assembly the other dose setting and drive mechanism. Via the non-interchangeable mechanism member, the respective drug delivery device may be adjusted to the specific liquid contained in the cartridge unit, for example different drugs or drug formulations. As opposed to interchangeable mechanism members, non-interchangeable mechanism members can only be used to assemble one of the first and second dose setting and drive mechanisms and not the other one. Accordingly, these members may be unique to the respective drug delivery device. For example, non-interchangeable mechanism members may be structurally different although they may be of the same type, e.g. piston rods, as will be discussed in more detail below. Interchangeable members may perform the same movements during dose setting and/or dose delivery, preferably not only the same types of movements but also by the same amount e.g. angular and/or axial displacement, with respect to the associated housing and/or with respect to the other mechanism members of the associated dose setting and drive mechanism. For example, interchangeable members may not change the way the mechanism operates and, in particular, may not alter the axial displacement of the bung relative to the cartridge body for a specific dose setting movement, e.g. by a specific angle and/or axial displacement, for setting of a particular dose. Non-interchangeable members, however, may have an effect on the axial displacement of the bung relative to the cartridge body. However, the non-interchangeable mechanism members expediently perform the same types of movement during dose setting and dose delivery as a mechanism member in the other dose setting and drive mechanism of the same type. Thus, on account of the non-interchangeable mechanism member(s) of the first dose setting and drive mechanism, the axial displacement of the bung relative to the cartridge body may be different for the first and second dose setting and drive mechanisms for the same dose setting movement, e.g. of the same rotation angle and/or axial displacement.

In an embodiment, the first and/or second mechanism members comprise a plurality of interchangeable mechanism members. Alternatively or additionally, the first and second mechanism members comprise a plurality of non-interchangeable mechanism members.

In an embodiment, the number of interchangeable mechanism members is greater than the number of non-interchangeable mechanism members. Accordingly, adjusting or modifying the dose setting and drive mechanism for a different drug delivery device may be facilitated by replacing just a few of the mechanism members and re-using interchangeable ones.

In an embodiment, the number of interchangeable mechanism members in the first and second dose setting and drive mechanism, which move relative to one another and/or relative to the first or second housing during the dose setting operation, is greater than the number of interchangeable members, which move relative to one another and/or to the first or second housing during the dose delivery operation. Preferably, the majority of mechanism members, which move or move significantly relative to the housing during the dose setting operation, such as 55% or more, 70% or more, or 90% or more, and/or two or more, three or more, or four or more members, are interchangeable members. The proportion and/or number of interchangeable members, which move or move significantly relative to the housing during the dose delivery operation is preferably less than the one during the dose setting operation. This has the advantage that the feeling during the dose setting operation for a user can be kept constant even between different drug delivery devices and the adjustment can be largely made in the mechanism members which move during dose delivery. That is to say, for setting a dose, in particular a dose of a particular size, e.g. a particular amount of international units (IU), the movements which have to be performed may be same in the first and second drug delivery device, e.g. with respect to rotation angle and/or axial displacement. The adjustment to how much the bung is displaced relative to the cartridge body, which effectively corresponds to how much liquid is dispensed from the cartridge for a pre-defined dose setting movement of mechanism members, can be effected by adjusting the mechanism members, which move, preferably only or only significantly, during the dose delivery operation, i.e. by providing one or more non-interchangeable members in these members.

In an embodiment, the number of non-interchangeable mechanism members between the first and the second drug delivery device, is greater in the mechanism members which move, preferably only or only significantly, relative to one another and/or to the housing during the dose delivery operation than in the mechanism members which move, preferably only or only significantly, relative to one another and/or to the housing during the dose setting operation.

In an embodiment, the dose setting and drive mechanism of the (respective) drug delivery device may comprise any arbitrary one of, an arbitrarily selected plurality of, or all of the following members or types of members:

A piston rod. The piston rod may be arranged to drive moment of the bung during the dose delivery operation. Thus, when the piston rod moves in the distal direction relative to the housing the bung may be displaced distally relative to the cartridge body. The piston rod may be a leadscrew or a tooth rod for example. The piston rod may be moved distally relative to the housing during dose delivery. The piston rod may be prevented from movement, distally and/or proximally, during the dose setting operation.

A bung interface member, e.g. a bearing. The bung interface member may be coupled to the piston rod, e.g. axially secured to the piston rod, and/or be configured to abut the bung. The piston rod may be rotatable relative to the bung interface member. If the piston rod rotates during dose delivery relative to the bung interface member, a separate bung interface member is advantageous, as the rotation of the piston rod is then not transferred to the bung. If the piston rod is only axially displaced, the piston rod may abut the bung immediately without a bung interface member associated with the piston rod, for example.

A drive member. The drive member may be operatively coupled to, e.g. engaged with, the piston rod to transfer a driving force or torque to the piston rod, e.g. from the user to the piston rod. Thus, the drive member may be that element, e.g. the only element, of the dose setting and drive mechanism, which is directly coupled to the piston rod. When the drive member moves during the dose delivery operation this movement is preferably transferred to the piston rod to cause movement of the piston rod in the distal direction. The drive member may or may not move during the dose setting operation. The drive member may be a sleeve. The drive member may comprise a plurality of parts, which act as one part during dose setting and dose delivery.

A dose setting member, e.g. a dial sleeve. The dose setting member is preferably movable relative to the housing in order to set a dose, e.g. the size of a dose of liquid to be delivered from the cartridge. The dose setting member may be a sleeve. The dose setting member may be rotatable and/or axially displaceable relative to the housing to set the size of a dose. The rotation angle and/or the axial displacement distance relative to the housing during the dose setting operation may be indicative for the size of the set dose. The dose setting member may move during dose setting and/or during dose delivery.

A user interface member, e.g. one or more user interface members. The user interface member may be a button. The user interface member may be operable, e.g. touched and/or moved, by the user for performing the dose setting operation and/or the dose delivery operation. The dose setting operation and/or the dose delivery operation may use a common user interface member or use different user interface members. For example, one user interface member may be associated with a dose setting operation, e.g. the dose setting member, and another one, e.g. a button or trigger member, which is moveable relative to that user interface member, which moves during dose setting, for initiating and/or switching to the dose delivery operation.

A tracking member. The tracking member may be coupleable or coupled to a tracking member path. The tracking member path, e.g. a thread, may be provided on the housing or on a mechanism member, e.g. the drive member, such as on one part thereof. During dose setting, there may be relative movement between the tracking member and the member on which the path is provided. The tracking member may be coupled to the dose setting member. In particular, movement of the dose setting member during the dose setting operation relative to the housing may be converted into movement of the tracking member relative to the tracking member path. The position of the tracking member along the tracking member path before dose setting is commenced may be indicative for the volume of liquid still available in the cartridge. that is to say for the volume of liquid which is currently in the cartridge. If the tracking member is arranged in an initial position relative to the path, the cartridge may be full. When it is arranged in an end position, the cartridge may be considered empty. When the tracking member is in the end position, increasing the size of the currently set dose further may be prevented. However, a previously set dose, which may be less than the maximum settable dose, may still be delivered during a dose delivery operation. A tracking member of this kind is often also designated as last dose member and, as it is sometimes implemented as a nut traveling along a helicon path, as a last dose nut.

A dose indication member. The dose indication member may be configured to indicate the size of the set dose. As the size of the dose may vary, the indication provided by the dose indication member may change. On an outer surface of the dose indication member indicia, e.g. numbers, may be provided to indicate the size of the currently set dose. The dose indication member may be a sleeve, such as a number sleeve, for example. The dose indication member may be coupled to the dose setting member, for example so as to convert movement of the dose setting member relative to the housing to set a dose into the movement of the dose indication member, where the size of the currently set dose, which is indicated by the dose indication member, changes as the dose setting member is operated to vary, e.g. increase or decrease, the currently set dose.

A dosing clutch member. The dosing clutch member may be provided to couple two mechanism members of the dose setting and drive mechanism during one of the dose setting operation and the dose delivery operation, preferably during only one of the operations. Thus, during one of the operations, the clutch member may couple the two mechanism members and during the other one of the operations the members may be uncoupled. The coupling may be a rotational lock such that the members co-rotate during one of the operations and relative rotation between the members is allowed during the other operation.

A reset clutch member. The reset clutch member may be provided to couple two mechanism members during the dose setting operation and the dose delivery operation.

However, the coupling may be released for a reset operation that is to say an operation, which moves the piston rod, which has been displaced relative to the housing from an initial position towards an end position to empty the cartridge, back towards the initial position. If the two mechanism members are coupled by the reset clutch member, movement towards the initial position of the piston rod may be prevented. Thus, decoupling the two mechanism members may be mandatory for a reset operation. The two mechanism members may be permanently coupled to one another, e.g. rotationally and axially locked, during dose setting and dose delivery and be decoupled, preferably only, for the reset operation, e.g. when the cartridge unit has been disconnected from the mechanism unit. The two mechanism members coupled by the reset clutch member may be two parts of the drive member.

A clicker member. The clicker member may be provided to generate an audible and/or tactile feedback. The feedback may be generated during the dose setting operation and/or the dose delivery operation. The feedback is preferably generated by a relative rotation between two parts during the relevant operation. One of the parts may be the clicker member and the other part may be another one of the mechanism members, which may rotate during the dose setting and/or the dose delivery operation, or the housing, for example.

The members discussed above may be unitary members, except where a multipart construction is explicitly disclosed and/or required for the function discussed in the context, e.g. for the drive member, which may have a plurality of parts, to provide a resettable or reusable device.

In an embodiment, the first dose setting and drive mechanism and the second dose setting and drive mechanism consist of first mechanism members and second mechanism members of mutually corresponding types of members. That is to say, if the first mechanism comprises a piston rod, so does the second and vice versa, for example. The same may hold for any one of the other types of mechanism members, which have been discussed above.

In an embodiment, the first liquid and the second liquid are different. Thus, the first cartridge and the second cartridge may be provided to dispense different liquids. The first liquid and the second liquid may comprise different drugs or different drug formulations. That is to say, the first liquid may comprise a first drug or drug formulation and the second liquid may comprise a second drug or drug formulation. Different drugs may mean different active pharmaceutical ingredients. Different drug formulations may mean that the first and second liquids may comprise the same drug or active pharmaceutical ingredient, e.g. insulin, but in different concentrations.

In an embodiment, the first cartridge and the second cartridge have different dimensions. For example, the first cartridge body and the second cartridge body may have different lengths and/or diameters. The length of the cartridge may be the axial extension from the proximal end to the distal or dispensing end of the cartridge. The diameter may be the width of the cartridge in the radial direction. The diameter may be the maximum or minimum diameter and/or an inner diameter and/or an outer diameter of the cartridge, e.g. of the cartridge body. The first cartridge and the second cartridge may define different volumes. The first and the second cartridge may have different filling volumes or maximum volumes of liquid, which can be filled into the respective cartridge. The volume of the first cartridge or cartridge body may be less than the one of the second cartridge or cartridge body, preferably less than 80% or less than 60% of the one of the second cartridge body, e.g. 50% of the one of the second cartridge body. The first cartridge body may be shorter than the second cartridge body. The first cartridge body may have a smaller diameter than the second cartridge body. The first cartridge body may be a 1.5 mL cartridge body and the second cartridge may be a 3.0 mL cartridge body, for example. The number of International Units (IU) of the drug contained in the first cartridge may be greater than the number of International Units (IU) of the drug contained in the second cartridge. The first liquid may have a higher drug concentration than the second liquid. For example, the concentration in the first liquid may be greater than or equal to the one in the second liquid multiplied by any one of the following values: 1.5, 2, 2.5, 2.75, 3. Even though the volume of liquid provided in the first cartridge may be less than the one in the second cartridge, the number of available (international) units of drug in the first cartridge may still be greater than the one available in the second cartridge. For example, the first cartridge may contain 450 IU and the second cartridge 300 IU of a drug, such as insulin.

In an embodiment, any arbitrary one of, any arbitrarily selected plurality of, or all of the following members are non-interchangeable mechanism members, particularly if comprised by the first mechanism members and the second mechanism members:
- the piston rod;
- the bung interface member;
- the drive member; if the drive member is composed of a plurality of parts which operate as one part during dose setting and/or dose delivery, not all of the parts may be non-interchangeable; Preferably that part of the drive member, which interacts with the piston rod may be non-interchangeable, the remaining part(s) of the drive member may be interchangeable part(s); and/or
- the tracking member and/or the member on which the tracking path is provided, e.g. that part of the drive member which engages the piston rod.

The non-interchangeable mechanism members mentioned above may be particularly suitable for cartridges of different dimensions, different volumes, different filling levels, and/or different drugs or drug formulations.

In an embodiment, the first cartridge and the second cartridge may have the same dimensions and/or filling levels. The liquid contained in the cartridges may, however, be different. For example, the drug concentration in the first cartridge may be greater than the one in the second cartridge as indicated above. The initial volume of liquid in the cartridges may be the same.

In an embodiment, any arbitrary one of, any arbitrarily selected plurality of, or all of the following members are non-interchangeable mechanism members, particularly if comprised by the first mechanism members and the second mechanism members:
- the piston rod;
- the drive member, e.g. the distal part thereof;
- the tracking member;
- the dose indication member.

These non-interchangeable mechanism members may be particularly useful if the first and second cartridges have the same dimensions, filing levels and/or volumes but different drugs or drug formulations.

In an embodiment, the remaining mechanism members, i.e. the ones which are not expressly recited as being non-interchangeable further above, may be interchangeable mechanism members. Thus, even though the mechanism members of the first drug delivery device and the second drug delivery device may comprise a piston rod, the piston rod cannot be exchanged between the two drug delivery devices, for example. If the piston rod were attempted to be exchanged, the mechanism of the other device would jam or be severely damaged. The same consequences may ensue in the event it is attempted to use one of the further non-interchangeable mechanism members in the other mechanism.

In an embodiment, any arbitrary one of, any arbitrarily selected plurality of, or all of the following mechanism members are interchangeable members, particularly if comprised by the first mechanism members and the second mechanism members:
- one or more parts of the drive member, if the drive member comprises a plurality of parts; one part of the drive member is preferably non-interchangeable as discussed above;
- the dose setting member;
- the user interface member(s);
- the dose indication member;
- the dosing clutch member;
- the reset clutch member; and/or
- the clicker member.

These interchangeable mechanism members may be particularly useful if the first cartridge and the second cartridge have different dimensions, filling volumes, and/or different drugs or drug concentrations in the liquid which is retained in the cartridge.

In an embodiment, the first drug delivery device and the second drug delivery device comprise the same or equivalent outer dimensions and/or outer shape. "Equivalent outer dimensions" may mean that the length, the maximum outer diameter, the minimum outer diameter, and/or the outer diameter at corresponding axial and/or angular positions, of the first and the second device do not deviate significantly from one another, e.g. by 5% or less, or 2% or less. The same outer dimension may mean that the quantities specified above are equal. Furthermore, "equivalent outer dimensions" may mean that as seen along an axial direction from a proximal end of the device to a distal end, the changes in the outer diameter of the two devices occur at the same or equivalent axial positions. This may hold for cartridges of different dimensions as well as for cartridges of the same dimensions.

In an embodiment, the first tracking member path and the second tracking member path are different, e.g. of a different length. Helical first and second tracking member paths may have different pitches and/or leads or the same pitch and/or lead. Specifically, the first tracking member path may be longer than the second tracking member path and/or of a smaller pitch and/or lead. As the length of the tracking member path may be associated with the amount of drug, the maximum number of doses, and/or the number of international units contained in the cartridge and the first cartridge may contain more drug, more doses or more units than the second cartridge, the first tracking member path is expediently longer than the second one. If the lengths are different but the pitch and/or lead is maintained, the mould for the member which comprises the tracking member path need not be completely re-designed but only the length of the tool feature defining the path has to be varied.

In an embodiment, the housing comprises a plurality of housing parts. The housing parts may be assembled to one another. Preferably the housing parts are assembled so as to be non-rotatable and/or non-axially displaceable relative to each other. Both housing parts may define a section of the outer contour of the drug delivery device. Both housing parts may be visible from the exterior of the device at least partly. One of the parts may be fully visible and one only partly. The one which is visible only partly may be partially arranged in the other housing part, e.g. as an inner body.

In the two drug delivery devices discussed above, one of the second housing parts, i.e. one of the plurality of parts of the housing of the second device, and one of the first housing parts, i.e. one of the plurality of parts of the housing of the first device, may be interchangeable. That is to say, both parts may be used in an interchangeable fashion in both devices. Another one of the second housing parts and another one of the first housing parts may be non-interchangeable. The housing parts, which are non-interchangeable, may be used to interact with one or more non-interchangeable mechanism members of the dose setting and drive mechanism of the respective device. These parts expediently engage with the associated piston rod. Also, further modifications may be provided on the non-interchangeable housing part, which may accommodate additional parts or provide space for them such as a cartridge bias system as will be discussed further below. The non-interchangeable housing part is expediently at least partially covered by the other housing part.

In an embodiment, the drug delivery device comprises a cartridge bias system. The cartridge bias system may comprise at least one resilient member. The cartridge bias system is preferably configured to exert a force on the cartridge to maintain the cartridge in a defined position, expediently relative to the mechanism unit and/or the housing. The force may be provided by the at least one resilient member. The force may act in the distal direction. The defined position may be a defined position relative to the cartridge holder. The force may be an elastic restoring force resulting from a deformation of the resilient member.

In the two drug delivery devices, the first cartridge bias system, i.e. the one of the first drug delivery device, comprises a rigid body, e.g. a rigid force transfer body. The rigid body may form a spacer to compensate the difference in dimension between the first cartridge and the second cartridge. The rigid body may be a non-interchangeable part, and, consequently, cannot be applied in the second drug delivery device. The at least one first resilient member and the at least one second resilient member of the first and second cartridge bias system may be interchangeable parts. Thus, the first resilient member may be usable in the second device and the second resilient member may be usable in the first device.

In an embodiment, the cartridge bias system of the drug delivery device may comprise a further resilient member. The further resilient member may be a non-interchangeable part or an interchangeable part.

In an embodiment, the first drug delivery device and the second drug delivery device have a first number of parts and a second number of parts, respectively. The first drug delivery device may have a greater number of parts than the second drug delivery device. The difference in part count between the two devices may be less than or equal to one of the following values: 5, 4, 3, 2, 1. For example, the first drug delivery device may comprise the rigid body in the first cartridge bias system in addition to the parts of the second drug delivery device. Otherwise, the part count may be the same.

In an embodiment, the first mechanism unit, the first cartridge unit, the second mechanism unit and/or the second cartridge unit are adjusted to one another such that the first cartridge unit cannot be connected to the second mechanism unit and/or the second cartridge unit cannot be connected to the first mechanism unit. Accordingly, although the cartridge unit may be releasable connected to the housing it can be avoided that cartridge units associated with one of the mechanism units can be connected to another mechanism unit. In this way, account can be taken for different drugs or for drug formulations contained in the liquids and/or of different filling levels. This increases user safety significantly, as dispensing drug with a wrong drive mechanism does have potentially lethal consequences. The risks can be reduced, if it is prevented that one cartridge unit is connected to another mechanism unit as it was intended for. Thus, the first mechanism unit and the first cartridge unit may be coded to one another as may the second mechanism unit and the second cartridge unit. The codings, e.g. mechanical codings, may be configured to prevent cross-connection or crosswise use of elements of different drug delivery devices.

In an embodiment, the housing of the drug delivery device may have a housing guide feature and the cartridge unit of the device may have a cartridge guide feature. The guide features may be configured to cooperate to form a guiding interface to guide movement of the cartridge unit relative to the housing to a relative position, where the housing and the cartridge unit are connected to one another. The guiding interface may guide this movement while the cartridge unit is being connected to the housing.

The first housing and the second cartridge unit may have matching guide features. That is to say, the housing guide feature of the first housing and the cartridge unit guide feature of the second cartridge unit may be adapted to form a guiding interface, which theoretically guide movement of the second cartridge unit relative to the first housing to a relative position, where the first housing and the second cartridge unit are connected. Alternatively or additionally the above applies for the second housing and the first cartridge unit. However, even though the respective guide features are adjusted such that units from different drug delivery devices could be connected to one another, it is expedient that this connection is prevented, as explained above.

In an embodiment, the second cartridge unit, which may have the longer cartridge, and the first housing are adjusted such that the second cartridge abuts the first housing and/or the rigid body of the first cartridge bias system to prevent connection of the second cartridge unit to first housing. Accordingly, before the connection position, where the second cartridge unit and the first housing were connected is reached, the cartridge abuts the first housing or the body which, preferably prevents further movement of the second cartridge unit relative to the first housing. The surface of the first housing which the second cartridge, e.g. the bung of the second cartridge, abuts may be a surface of the non-interchangeable housing part. Thus, a surface of the second cartridge may be used for coding purposes.

In an embodiment, the first cartridge holder has a first cartridge coding structure and the second mechanism unit has a second mechanism coding structure. The respective structure may comprise one or more coding features. The coding structures may be adjusted to prevent, e.g. by abutment of coding features of the mechanism unit and the cartridge holder, connection of the first cartridge holder to the second mechanism unit or the second housing. The coding structures may be configured to prevent, e.g. by abutment of coding features, relative movement of the first cartridge holder towards the second housing, particularly before the first cartridge unit is connected to the second housing. That is to say, the cartridge unit with the potentially shorter cartridge may have a coding structure to prevent connection to the second housing. In the second cartridge unit with respect to the first housing, the cartridge may be utilized to provide the coding feature, which prevents that the second cartridge and the first housing are connected. Alternatively or additionally, the second cartridge holder may have a second cartridge coding structure. The second cartridge coding structure may be compatible with the second mechanism coding structure and be incompatible with the first mechanism coding structure to prevent connection of the second cartridge unit to the first housing.

In an embodiment the (respective) cartridge coding structure is integrated into a proximally facing surface of the cartridge holder, e.g. into a proximal rim of the cartridge holder. The structure may have protruding portions and/or ramp surfaces, which are circumferentially disposed on the cartridge holder. The protruding portions may be oriented in the proximal direction. The protruding portions may form coding features.

In an embodiment, the cartridge unit guide features and the cartridge coding structure are axially offset, e.g. by a distance greater than or equal to a distance required for an axial movement to connect the cartridge unit to the housing while the guiding interface is established.

In an embodiment, the first cartridge holder has three or more axially extending cartridge support features. The cartridge support features may define a cartridge retaining space between them. The cartridge retaining space may have a diameter greater than or equal to the one of the first cartridge. Accordingly, the first cartridge may be received within the cartridge retaining space. The cartridge retaining space may have a diameter less than the one of the second cartridge. Accordingly, the second cartridge may abut the cartridge retaining feature before it can be received entirely in the first cartridge holder. In this way, it is avoided that the wrong cartridge is assembled within the first cartridge holder. Likewise, a radial position is stabilized of the first cartridge. Thus, the cartridge support features may bridge a void, which is present within the interior of the first cartridge holder, which may have the same or substantially the same outer dimensions as the second cartridge holder. Accordingly, the cartridge support features may distinguish the first cartridge holder from the second cartridge holder.

In an embodiment, the first cartridge holder and the second cartridge holder both have a length, which is greater than the length of the first cartridge and the one of the second cartridge. Accordingly, the respective cartridge can be received entirely in the associated cartridge holder.

In an embodiment, when the cartridge holder is connected to the housing, a portion of the cartridge holder protrudes, e.g. distally, from the housing. The length of the first portion of the first cartridge holder which protrudes from the first housing and the second portion of the second cartridge holder which protrudes from the second housing may be identical or substantially identical, e.g. with a deviation of 5% or less or 2% or less.

In an embodiment, the first cartridge holder and the second cartridge holder may have identical outer contours or shapes.

In an embodiment, the first cartridge holder and the second cartridge holder may have the same or equivalent outer dimensions and/or outer shape. Equivalent may have the meaning defined further above.

In an embodiment, the drug delivery device comprises a cap. The cap of the first drug delivery device and the one of the second drug delivery device may be interchangeable parts or non-interchangeable parts. The cap may designed to be connected to the housing or the cartridge holder. The cap, when connected, preferably covers at least the majority of the length of the cartridge holder or the entire cartridge holder.

In an embodiment, the second piston rod has one or more blocking features, which are arranged to block movement of the second piston rod in the distal direction relative to the first cartridge body. The respective blocking feature may protrude radially from the second piston rod. A distally facing surface of the blocking feature of the second piston rod may be arranged to abut a proximally facing surface of the first cartridge, e.g. the proximal rim of the first cartridge or cartridge body. The blocking feature may define a radial extension or diameter of the piston rod in the region of the blocking feature, which is less than the inner diameter of a proximal opening of the second cartridge or cartridge body and/or greater than or equal to the inner diameter of a proximal opening of the first cartridge or cartridge body. Thus, if accidentally, a first cartridge unit is attempted to be assembled to a second mechanism unit, for example if no coding is provided or the coding is destroyed, it is still prevented that the second piston rod can displace the first bung distally relative to the first cartridge body as the blocking feature abuts the cartridge or cartridge body. Accordingly, user safety is increased by this measure. The blocking feature may be offset axially from a distal end of the second piston rod. The distance by which the blocking feature is offset is preferably small, e.g. less than the distance by which the second piston rod is moved during the dose delivery operation, if the minimum settable dose is set by the second dose setting and drive mechanism. Thus, the delivery operation can be stopped timely by the blocking feature abutting the cartridge, for every dose which can be set.

In an embodiment, as seen from the distal end along the axis of the second piston rod, the second bung interface member connected to the second piston rod has a radial extension or diameter greater than the one of the second piston rod in the region of the blocking feature. The second bung interface member may be dimensioned so as not to fit into the interior of the first cartridge body, i.e. it may be a non-interchangeable mechanism member. The bung interface member may be accessible for manipulation by the user when the cartridge unit has been disconnected from the housing. Thus the user could theoretically remove the second bung interface member from the second piston rod and use the second piston rod to drive the first bung distally. This may be prevented by the blocking feature(s).

In an embodiment, the force transfer chain or coupling sequence in the dose setting and drive mechanism from the user interface member or dose setting member to the piston rod when the member is manipulated by the user is the same for the first dose setting and drive mechanism and for the second dose setting and drive mechanism, expediently during the dose delivery operation and/or the dose setting operation. Thus, the couplings in the mechanisms may be equal, equally acting, and/or the same couplings may be present between the same types of members. The couplings may comprise splined or rotationally locked couplings, helical, e.g. threaded, couplings and/or axial couplings such as axial locks between members. Accordingly, the components of the two different dose setting and drive mechanisms may move relative to one another in a corresponding way as seen from the user interface during dose setting and dose delivery. Nevertheless, the same dose setting operation, e.g. by rotation and/or axial displacement of the user interface member or dose setting member by the same angle or axial distance preferably results in a different axial displacement of the piston rod during dose delivery for the first dose setting and drive mechanism and the second dose setting and drive mechanism.

In an embodiment, during the dose setting operation, relative movement between the mechanism members of the drug delivery devices is governed by a dose setting coupling system where a load is propagated from the user interface member through the mechanism members in a dose setting load transfer sequence. The first dose setting coupling system and the second dose setting coupling system may have the same load transfer sequences. They may have the same types of relative movement (axial, rotational, or helical) and also the same absolute relative displacements (angle and/or axial distance) between the components or member, expediently of corresponding types, which move relative to another during the dose setting operation.

In an embodiment, during the dose delivery operation, relative movement between the mechanism members is governed by a dose delivery coupling system, where a load is propagated from the user interface member through the mechanism members in a dose delivery load transfer sequence. The dose delivery coupling system may differ from the dose setting coupling system, e.g. on account of the coupling provided by the clutch member being released. This load may be transferred to the bung or the bung interface member by the piston rod. For the first and the second drug delivery device, the first dose delivery coupling system may have the same load transfer sequences. Also, the couplings between equal types of members may be equal in or along the load transfer sequence. However, the couplings may generate different relative displacements between the components during dose delivery.

In an embodiment, the device may be a manually operated device. Thus, the entire dispensing force may be provided by a user. Alternatively, the device may be a spring-assisted device, where only a part of the force is provided by the user and the remaining part is provided by a spring. As a further alternative, the device may be a spring-driven device, where the entire dispensing force is provided by the spring.

In an embodiment, in one of the drug delivery devices, for example in the first drug delivery device which may have the cartridge of reduced length and/or diameter, the piston rod may be moved proximally, i.e. away from the bung, in the dose setting operation. Moving the piston rod away from the bung may reduce the risk of 'weeping' of drug from the cartridge during dose setting. The distance by which the piston rod is moved in the dose setting operation may be greater than a distance by which the piston rod in the other drug delivery device of the two drug delivery devices, e.g. the second device, moves in the proximal direction during dose setting. Particularly, in the other drug delivery device, movement in the proximal direction of the piston rod during dose setting may be avoided. Thus, the bung interface member or the piston rod may be consistently in contact with the bung in the other device. The distance by which the piston rod is moved proximally relative to the bung during dose setting may be less than or equal to one of the following values: 1 mm, 0.5 mm, 0.3 mm, 0.2 mm, 0.1 mm. The distance by which the piston rod is moved proximally may depend on the size of the dose which is set. The values may relate to the distance by which the piston rod is moved if, during the dose setting operation the maximum settable dose which can be delivered by the drug delivery device is set. The distance by which the piston rod is moved proximally may be insignificant as compared to the movement of the other mechanism members during dose setting.

The distance (D) by which the piston rod is moved proximally for the maximum settable dose multiplied by the mechanical advantage (MA) of the dose setting and drive mechanism, which may be greater than 1, is preferably less than or equal to the relative axial displacement (AD), e.g. in the distal direction, between members which are coupled by a clutch member, e.g. the dosing clutch member, said axial displacement being required to release the coupling provided by the clutch member, for example in order to switch from the dose setting operation to the dose delivery operation. For example, D*MA may be less than or equal to one of the following value: 0.5AD, 0.3AD, 0.2AD. The movement for releasing the coupling may be necessary anyway and the user may not even notice that there is an additional movement which he has to perform before the piston rod contacts the bung again and drug is actually dispensed during dose delivery. The proximal movement of the piston rod during dose setting should, of course, preferably be less than the distal movement of the piston rod required to deliver the set dose or maximum settable dose, e.g. less than 10%, less than 5%, or less than 2%.

The difference between the two devices in the proximal movements of the piston rod during dose setting may originate from an interchangeable member, e.g. the dose indication member, which is used in both devices, where said member is, however, mismatched somewhat to the remaining mechanism members in one device, expediently the one where the piston rod moves proximally during dough setting. Such a slight mismatch may be still tolerable, on account of the benefits of an interchangeable member, e.g. regarding cost efficiency.

In one device, two different threaded couplings, e.g. couplings between two different pairs of members or parts, may be governed or formed by threads, e.g. helical threads, of the same pitch and/or lead. One coupling may be between the drive member and the piston rod. The other coupling may be between the dose indication member and the housing. In the other drug delivery device, e.g. the first drug delivery device, the couplings may still be threaded couplings between corresponding members or types of members. However, the leads and/or pitches of the threads may be different, preferably by less than 5%, less than 2%, or less than 1%. Such a slight mismatch may result in a proximal movement of the piston rod during dose setting in one of the devices as discussed above.

Another aspect relates to a method of producing a first mechanism unit which is configured to be connected to a first cartridge unit to form first a drug delivery device, comprising the following steps:
  providing a second mechanism unit as a model for the first mechanism unit, the second mechanism unit being configured to be connected to a second cartridge unit which is different from the first cartridge unit, wherein the second mechanism unit comprises a second housing and a second dose setting and drive mechanism which is at least partly arranged in the second housing, the second dose setting and drive mechanism comprising a plurality of second mechanism members which are movable relative to the second housing and/or relative to one another during a dose setting operation for setting a dose of the second liquid and/or a dose delivery operation for delivering the set dose,
  providing a first housing for the first mechanism unit;
  producing one interchangeable mechanism member in accordance with one of the second mechanism members;
  producing one non-interchangeable mechanism member which is adjusted to the first cartridge unit,
  assembling a first dose setting and drive mechanism for the first mechanism unit, the first dose setting and drive mechanism comprising the interchangeable mechanism member, which expediently could be used in the second dose setting an drive mechanism, and the non-interchangeable mechanism member, which expediently cannot be used in the second dose setting and drive mechanism, and arranging the interchangeable mechanism member and the non-interchangeable mechanism member in the first housing, e.g. during or after the first dose setting and drive mechanism has been assembled.

With the proposed concepts, drug delivery devices can be adjusted to specific drugs or different drug concentrations, filling levels in cartridges, and/or cartridge dimensions. Although the drugs and drug concentrations may be different, the same dose setting movements, that is to say the same rotation angles and/or axial displacements of members, which are manipulated by the users, such as the dose indication member, the dose setting member and/or the user interface member, occur. However, the resulting axial displacement of the piston rod relative to the housing and/or the cartridge body may be different. This has various advantages. For example, the moulds or assembling tools for the interchangeable parts can be reused. Only a few parts of the mechanism need adjustment, which then are non-interchangeable parts. As the general mechanism of an existing device may have a proven functionality already, slightly readjusting an existing device may provide a regulatory advantage. Thus, approval by the regulatory authorities like the FDA, for example, may be more easily gained for a device architecture which has a proven record already, where this architecture is slightly modified.

The terms "distal" and "proximal" as used herein may refer to opposite axial directions or ends. "Distal" may refer to a direction towards the dispensing end or an end of a component of a drug delivery device which is or is to be arranged closest to the dispensing end of the cartridge, the cartridge unit or the drug delivery device. "Proximal" may refer to a direction away from the dispensing end or an end which is or is to be arranged further away from the dispensing end.

Features disclosed above in conjunction with the drug delivery device should not be regarded as referring to only the recited aspect or embodiment. Rather, the features also apply for other embodiments or aspects. Features disclosed in conjunction with the device do also apply for the method, for example, and vice versa. Of course, features disclosed in specific embodiments, be it above or further below, can also be applied in combination with one another and/or with other features of other aspects or embodiments. Features disclosed for the arrangement with two drug delivery devices may, of course, also apply for one drug delivery device and vice versa.

Further features, advantages and advantageous embodiments of the present disclosure will become apparent from the following description of the exemplary embodiments in conjunction with the drawings.

BRIEF DESCRIPTION OF FIGURES

FIG. 1 shows a drug delivery device with a cap attached.

FIG. 2 shows the drug delivery device of FIG. 1 with the cap removed and a dose of 79 units dialed.

FIG. 5a shows the inner body of the drug delivery device of FIG. 1.

FIG. 5b shows a detail of the inner body of FIG. 5a.

FIG. 6 shows the cartridge holder of the drug delivery device of FIG. 1.

FIG. 7a shows a first display member component of the drug delivery device of FIG. 1.

FIG. 7b shows a detail of the first display member of FIG. 7a.

FIG. 17 shows a cut-away view of the proximal part of the drug delivery device of FIG. 1 in a zero unit position with the button released.

FIG. 18 shows a cut-away view of the proximal part of the drug delivery device of FIG. 1 in a position with some units dialed.

FIG. 19 shows a cut-away view of the proximal part of the drug delivery device of FIG. 1 in a zero unit position with the button pressed.

FIGS. 20A through 21B schematically illustrate embodiments of cartridge assemblies where a cartridge is assembled to a cartridge holder.

FIG. 28A shows the unassembled state and FIG. 28B shows the assembled state.

FIGS. 38A through 38C illustrate modifications to a piston rod.

FIGS. 39A and 39B illustrate modifications to a bearing.

FIGS. 42A and 42B illustrate modifications in a housing part.

Figure 3:
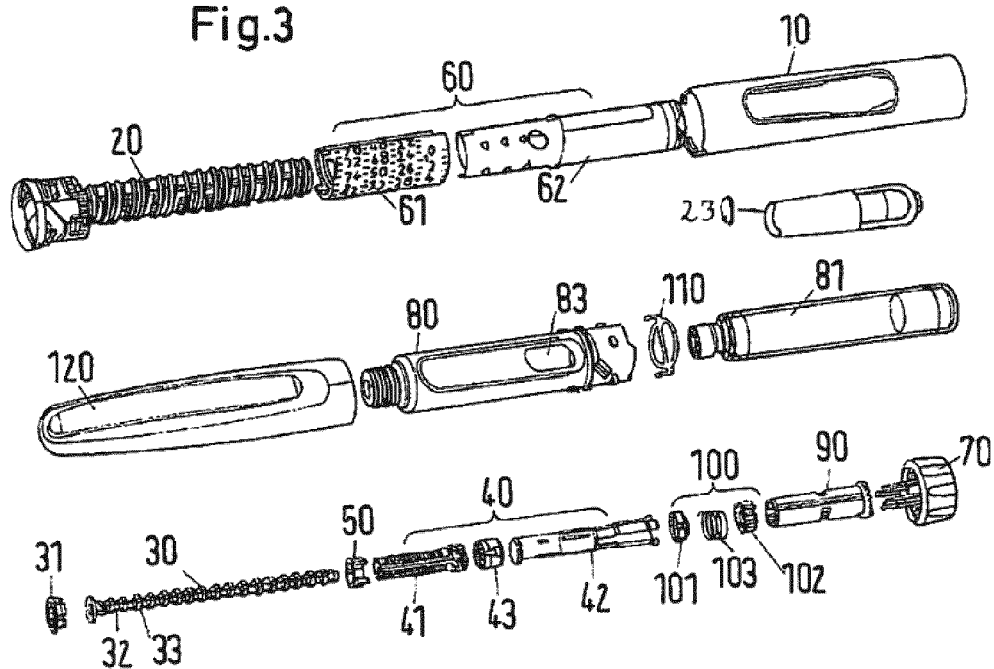
FIG. 3 shows in an exploded view the components of the drug delivery device of FIG. 1.

Like elements, elements of the same kind and identically acting elements may be provided with the same reference numerals in the figures. Additionally, the figures may be not true to scale. Rather, certain features may be depicted in an exaggerated fashion for better illustration of important principles.

DETAILED DESCRIPTION

FIGS. 1 and 2 show a drug delivery device 1 in the form of an injection pen. The device has a distal end (lower end in FIG. 1) and a proximal end (upper end in FIG. 1). The component parts of the drug delivery device 1 are shown in FIG. 3 in more detail. The drug delivery device 1 comprises an outer housing part 10, an inner body 20, a piston rod 30, a driver or drive member 40, a nut or tracking member 50, a display mechanism 60, a button or user interface member 70, a cartridge holder 80 for receiving a cartridge 81, a clutch 90, a clicker 100, a spring or a plurality of springs 110, a cap 120 and a window insert 230. A needle arrangement (not shown) comprising a needle hub and a needle cover may be provided as additional components, which can be exchanged as explained above. The piston rod 30 comprises a bearing 31. The driver 40 comprises a distal driver part 41 and a proximal driver part 42. The parts 41 and 42 are coupled by a coupler 43. The display mechanism 60 or the drug delivery device comprises a number sleeve or dose indicator 61 and a dial sleeve or dose setting member 62. The clicker 100 comprises a distal clicker part 101, a proximal clicker part 102 and a spring 103.

Figure 4:
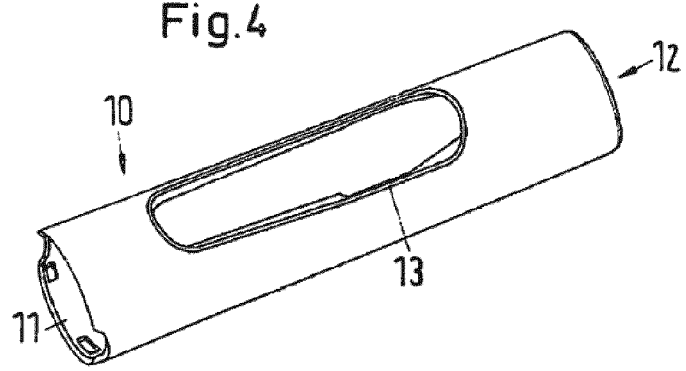
FIG. 4 shows the outer body of the drug delivery device of FIG. 1.

The outer housing part 10, which is shown in FIG. 4, is a generally tubular element having a distal part 11 for attaching the inner body 20 and a proximal part, which is provided with a rotational hard stop 12 on its inner surface (not shown) which contacts one or more mating faces of the display mechanism 60 when the maximum units (in this example 80U, e.g. 80IU) stop is engaged. A proximal end face of the housing part also serves as the end of dose dispense stop for the button 70, and the bore in the end face centers the display mechanism 60 during both dialing and dispense. An aperture 13 is provided for receiving window insert 230. The outer body 10 provides the user with a surface to grip and react against during dispense.

The inner body 20 is a generally tubular element having different diameter regions. As can be seen in FIGS. 17 to 19, the inner body 20 is received in the outer body 10 and permanently fixed therein to prevent any relative movement of the inner body 20 with respect to the outer body or housing part 10. The inner body has the functions to house the drive mechanism within, guiding the clickers and the last dose nut 50 via internal splines, to provide an internal thread through which the piston rod 30 (lead screw) is driven, to support and guide the number sleeve 61 and the dial sleeve 62 on an external thread form, to secure the cartridge holder 80 and to secure the outer body 10 and the window insert 230. Thus, the inner body interacts with components of the dose setting and drive mechanism. The inner body and the outer housing part may together form a housing of the device 1.

The outermost diameter of the inner body 20 also forms part of the visual design and remains visible when the cap 120 is secured to the cartridge holder 80 as a ring separating the cap 120 from the outer body 10. This visible ring also has depressions which align with the cap snap features on the cartridge holder 80 to indicate that the cartridge holder has been correctly fitted.

An external thread 21 is provided on the outer surface of the inner body 20. Further, splines 22 (FIG. 5b) are provided on the inner surface of the inner body 20. These internal splines 22 guide the clicker 100 axially during both dialing/setting and dispense and also prevent the last dose nut 50 from rotating. Some of the splines may be wider to ensure correct rotational assembly of the internal components, and these wider splines may have a stepped entry and angled surface to encourage the last dose nut 50 to rotate up against the stop face on the distal drive sleeve 41 during assembly. At the open end shown in FIG. 5b there are additional short splines which together with the alternating long splines 22 are used to rotationally lock the button 70 (dose dial grip) at the end of dispense and serve to increase the strength of the 0U dial stop when the button 70 is depressed. This is achieved by engagement with male spline features on the clutch component 90.

Bayonet features 23 guide the cartridge holder 80 into the mechanism, e.g. during cartridge replacement, compressing the cartridge bias spring 110, and then back off the cartridge holder 80 a small distance in order to reduce axial play in the mechanism. Snap features inside the inner body 20 lock the cartridge holder 80 rotationally when it has been correctly fitted. The profile of these snaps aims to prevent the user from partially fitting the cartridge holder 80, the cartridge bias spring 110 ejecting the cartridge holder 80 if the snaps have not at least started to engage. A window retention nose 24 retains the window insert 230 when the outer body 10 and window insert 230 assembly is axially inserted onto the inner body 20. Two diametrically opposite stop faces 25 define the rotational end position for the number sleeve 61. This end position may be the end of dose detent position (e.g. corresponding to a zero dose being set, e.g. of 0U, such as 0IU).

The piston rod 30 is an elongate element having two external threads 32, 33 with opposite hand which overlap each other. One of these threads 32 engages the inner thread of the inner body 20. A disk-like bearing 31 is provided at the distal end of the piston rod 30. The bearing 31 may be a separate component as shown in FIG. 3 or may be attached to the piston rod 30 as a one-piece component via a predetermined breaking point.

The piston rod 30 transfers the dispense load from the driver 40 to the bearing 31, creating a mechanical advantage greater than 1:1 by converting the torque generated on the piston rod 30 by the driver 40 thread interface into additional axial load as the piston rod passes through the thread in the inner body 20. The piston rod 30 is reset by pressing on the bearing 31 and this in turn rotates the piston rod back into the inner body 20. This disengages and then rotates the distal drive sleeve 41, thereby resetting the last dose nut 50 back to its starting position on the distal drive sleeve 41.

Figure 9:
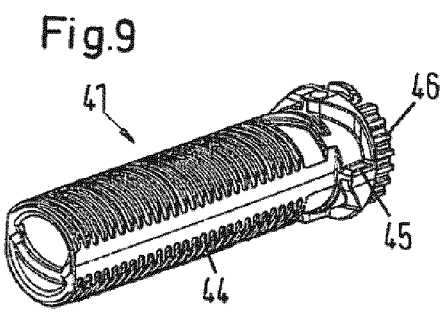
FIG. 9 shows a first driver component of the drug delivery device of FIG. 1.
Figure 10:
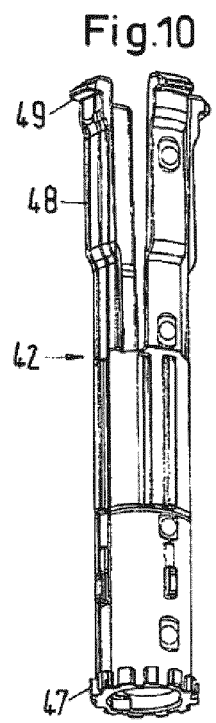
FIG. 10 shows a second driver component of the drug delivery device of FIG. 1.
Figure 11:
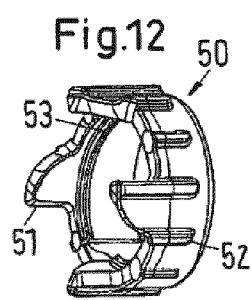
FIG. 11 shows a third driver component of the drug delivery device of FIG. 1.

The driver 40 is a generally tubular element having in the embodiment shown in the Figures a plurality of components which are depicted in FIGS. 9 to 11 in more detail.

The distal drive sleeve 41 engages with the piston rod thread 33 to drive the piston rod 30 through the inner body 20 during dose delivery. The distal drive sleeve 41 is also permanently connected to the coupler 43 which in turn is releasably engaged through reset clutch features to the proximal drive sleeve 42. The two halves of the drive sleeve are rotationally and axially connected during dialing and dispense, but are de-coupled rotationally during device reset so that they can rotate relative to each other.

The external thread 44 engages with the last dose nut 50. The thread form has three stages, a shallow first stage (left hand side in FIG. 9) over which the nut 50 travels to count the majority of the units dialed, a fast stage over which the last dose nut moves rapidly axially prior to engaging the stop faces, and a final shallow section which ensures that when the stop faces have engaged, the axial restraint on the nut 50 extends over a reasonable length of thread form. Four equi-spaced stop faces 45 engage with mating stop faces 51 on the last dose nut 50 to limit the number of units that can be dialed. Splines 46 are provided at the proximal end of distal drive sleeve 41 to transfer torque from or to the coupler 43, which may be snapped on the distal drive sleeve 41.

The proximal drive sleeve 42 shown in FIG. 10 supports the clicker components 100 and the clutch 90 and transfers rotational movement from the dose button 70 to the coupler 42 and distal drive sleeve 41.

Teeth features 47 located at the distal end of proximal drive sleeve 42 engage with the reset clutch features on the coupler 43 to connect both halves of the drive sleeve during dialing and dispense. During reset these teeth 47 disengage.

Several splines are provided on the outer surface of proximal drive sleeve 42 engaging with the distal and/or proximal clicker part 101,102, preventing relative rotation during dialing and dispense. Further splines, which are located in the middle region of proximal drive sleeve 42, engage with the clutch 90 component. They may be arranged to be non-rotationally symmetric so that the various clicker components cannot be assembled accidentally upside down.

The proximal portion of proximal drive sleeve 42 has four arms or fingers 48. A hook-like bearing surface 49 exists on the underside (as seen in FIG. 10) of flange segments on the end of the flexible fingers 48. The flexible fingers 48 are separated with gaps or slots that make space for the button 70 to snap to the clutch 90 and also enable these fingers to flex inwards during assembly of the proximal drive sleeve 42 to the dial sleeve 62. After assembly the hooks 49 retain the proximal drive sleeve 42 relative to the dial sleeve 62 under the reaction force from the spring 103. During dispense the button 70 depresses the spring 103 via the clutch 90 and the clicker components and this spring 103 is reacted through the coupler 43 to the proximal drive sleeve 42 which then through these bearing surfaces applies axial load to the dial sleeve 62. This axial load drives the dial sleeve 62 and hence number sleeve 61 along the helical thread of the inner body 20, back into the body of the device, until the 0U stop faces on the number sleeve 61 contact the inner body 20.

The coupler 43 shown in FIG. 11 rotationally couples the two halves of the drive sleeve together during dialing and dispense, whilst allowing them to de-couple during reset. The coupler 43 also has to transfer the last dose protection stop load from the proximal drive sleeve 42 to the distal drive sleeve 41. Two sets of teeth are provided in the coupler 43 for engaging teeth 46 and teeth 47, respectively. The coupler 43 is snapped onto distal drive sleeve 41 allowing limited relative axial movement with respect to the proximal drive sleeve 42.

The nut 50 is provided between the inner body 20 and the distal drive sleeve 41 of driver 40. Stop faces 51 are located on the proximal face of last dose nut 50 to limit the number of units that can be dialed if the stop faces 51 contact stops 45 of distal drive sleeve 41. The function of the last dose nut 50 is to prevent the user from dialing beyond a finite amount. This limit is based on the dispensable volume of the cartridge 81 and when reached, the user must replace the cartridge 81 and reset the device.

External ribs 52 of the nut 50 engage splines 22 of inner body 20. An internal thread 53 of the nut engages the external thread 44 of distal drive sleeve 41. As an alternative, splines and ribs could be provided on the interface between the nut 50 and the driver 40 and threads could be provided on the interface between the nut 50 and the inner body 20. As a further alternative, the nut 50 may be designed as e.g. a half nut.

The display mechanism or display member 60 is a generally tubular element or system which is composed of number sleeve or dose indicator 61 and dial sleeve 62 which may be snapped together during assembly to axially and rotationally constrain these two components, which may thus act as a single part or member. However, other device architectures may involve a dose setting member or dial sleeve 62 which moves axially and/or rotationally relative to the dose indicator or number sleeve 61 during dose setting and/or dose delivery. For example, the dose setting member may be manipulated by a user for setting a dose and the button may only be operated when dispensing the set dose. In the present embodiment, however, the button 70 is manipulated for setting and dispense.

Figure 8:
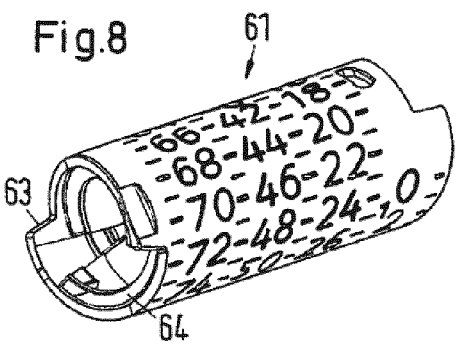
FIG. 8 shows a second display member component of the drug delivery device of FIG. 1.

The main functions of the number sleeve 61 depicted in FIG. 8 are to provide a surface onto which dose numbers can be printed to display the dialed dose, to guide the helical path of the internal mechanism during dialing to follow the helical thread form on the piston rod 30 when threaded to the inner body 20 and to attach to the dial sleeve 62.

The number sleeve 61 is designed to be fully enclosed in the outer body 10 during dialing and dispense and therefore only the dialed dose is visible to the user through the window aperture. The number sleeve has a 0U (minimum or zero dose) stop face 63 to limit its travel when dialed in but the 80U (maximum dose) stop faces that limit the dialed out condition are located on the dial sleeve 62. At the end of each dispense stroke, this stop face 63 engages with mating surface 25 on the inner body 20 to limit the rotational position of the number sleeve 61.

A helical drive face 64 forms a thread that guides the number sleeve 61 during dialing and dispense to follow the helical path 21 on the inner body.

The dial sleeve 62 is assembled to the number sleeve 61 such that once assembled, no relative movement is allowed. The parts are made as separate components to enable both molding and assembly. Also, whereas the number sleeve 61 is preferably white to give contrast for the e.g. black dose numbers, the dial sleeve 62 color can be chosen to suit the aesthetics or perhaps to distinguish the drug type, if desired.

At the dose proximal end, the dial sleeve 62 has internal clutch features 65 that engage with the clutch component 90 during dialing and disengage from the clutch during dispense. These clutch features 65 rotationally lock the dial sleeve 62 to the clutch 90 during dialing and when the 0U and 80U stops are engaged. When the button 70 is depressed these clutch features disengage to allow the clutch 90 and drive mechanism to move axially whilst the dial sleeve 62 and number sleeve 61 spin back to the 0U start position.

The dial sleeve 62 rotates out during dialing through its engagement with the clutch 90 and number sleeve 61, and rotates back in during dispense under the axial force applied by the proximal drive sleeve 42 to a flange-like bearing face 66 on the end of the dial sleeve. This bearing face 66 engages with the flexible arms 48 of the proximal drive sleeve 42 during dispense. Two diametrically opposite faces 67 engage with the outer body 10 when the maximum dose (e.g. 80U) has been dialed, forming the maximum dose stop faces.

A ratchet arm 68 engages with ratchet features on the button 70 (dose dial grip) to provide audible feedback during dispense, giving one click per unit delivered. Further, this prevents the user from gripping and rotating the number sleeve 61 outwards from a partially dialed out position whilst holding the button 70 pressed in. This would back wind the piston rod 30 which would result in an under dose on the subsequent dialed dose. It may further strengthen the 0U stop.

Figure 16:
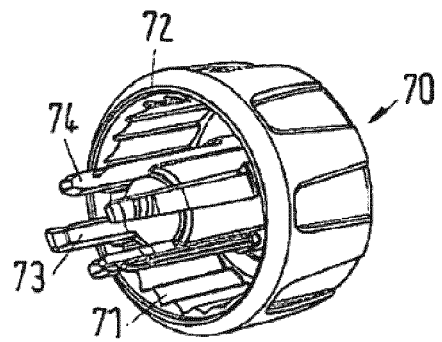
FIG. 16 shows the button of the drug delivery device of FIG. 1.

The button 70 which is shown in FIG. 16 serves as a dose dial grip and is retained by the clutch 90 to transfer the actions of the user to the clutch. It also carries ratchet teeth 71 that engage the ratchet arm 68 on the dial sleeve 62, which serves as the dispensing clicker giving audible feedback (ratchet clicks), and an end face 72 which serves as the dose completion stop face with the outer body 10. This end face 72 thus serves to define the end position during dispense when it contacts the outer body 10 to provide a very positive stop improving dose accuracy.

A central sleeve-like portion of button 70 is provided with four arms 73 having hook-like snap features 74 at their respective distal ends. The arms 73 form splined surfaces engaging with the clutch 90 to transfer torque from the button 70 through the clutch to the dial sleeve 62 and proximal drive sleeve 42. The snap features 74 engage apertures in the clutch 90 and are designed with angled undercut faces to maintain engagement when an axial load is applied to pull the button 70 out of the pen body 10. The space between arms 73 defines pockets giving clearance for the flexible arms 48 of proximal drive sleeve 42 to slide freely relative to the button 70 and clutch 90 when the button 70 is depressed and released during dose dispense.

The cartridge holder 80 attaches to the inner body 20 with a bayonet connection 82 and houses the glass ampoule or cartridge 81 containing the medication to be dispensed. The cartridge holder 80 includes an aperture 83 in the rear face (as seen in FIG. 6) which if gripped by the user prevents the ampoule from falling out when the cartridge holder is removed from the inner body 20. The front face is printed with a dose number scale. The threaded distal end 84 is used to attach disposable pen needles.

A tubular clutch 90 is provided between the display mechanism or member 60 and the button 70. The clutch is fixed relative to and retains the button 70 and together they travel axially relative to the proximal drive sleeve 42 when the button 70 is depressed during dispense, disengaging the clutch teeth from the dial sleeve 62. It also transfers torque from the button to the proximal drive sleeve 42, and the dialing and 0U/80U stop loads from the button via the clutch teeth to the dial sleeve and number sleeve.

Drive sleeve splines 91 provided on an inner surface of the clutch engage with the proximal drive sleeve 42. At the distal end face, clutch biasing teeth 92 are provided which mate with similar teeth on the proximal clicker part 102 to ensure that in the button out position (dialed dose) the clutch is locked in rotation to the proximal clicker part 102 under the biasing action of the clutch spring 103. The teeth 92 are shallow in height to prevent the proximal clicker part 102 from engaging with splines on the proximal drive sleeve 42 during dialing. Four snap apertures 93 serve to retain the snap features 74 of button 70. Near its proximal end, the clutch has splines 94 which at the end of dispense with the button 70 depressed lock to the inner body 20 to prevent the user from rotating the button 70 below the 0U position.

Clutch teeth 95 engage with clutch teeth 65 of the dial sleeve to rotationally couple the button 70 via the clutch to the number sleeve 61. During dispense the clutch is moved axially so as to disengage these clutch teeth 95 releasing the dial sleeve 62 to rotate back into the device whilst the clutch 90 and hence driver 40 move axially to dispense the dose.

The clicker 100 comprises a distal clicker part 101, a proximal clicker part 102 and a spring 103. The clutch spring 103 serves to bias the button 70 out so that at the end of a dose the button 70 pops out, re-engaging the clutch 90 with the dial sleeve 62 ready for dialing. Further, it provides the spring force for the clicker components to act as clickers and also as detent positions for the number sleeve 61. In addition, it holds the two halves of the drive sleeves 41, 42 in rotational engagement during dialing and dispense, whilst allowing them to disengage during device reset.

The distal clicker part 101 is permanently splined to the proximal drive sleeve 42 and engages with the proximal clicker part 102 which in turn is splined to the inner body 20. During dialing when the drive sleeve is rotated relative to the inner body, the two clickers 101, 102, rotate relative to each other under the compression force of the clutch spring 103. This force combined with the clicker teeth formed on the end face of each clicker provides the clicks and also the detent dialing positions.

During dispense the two clickers 101, 102 are pressed together under the dispense load and therefore prevent relative rotation between the proximal drive sleeve 42 and inner body 20, driving the piston rod forwards to deliver the dose. The splines 104 on the inner bore rotationally couple the distal clicker part 101 to the proximal drive sleeve 42 at all times, but allow free axial movement when the button 70 is depressed during dispense and when the two clickers ride over each other during dialing. The profile of the clicker teeth 105, 106 on both distal clicker part 101 and proximal clicker part 102 are identical and ride over each other under the compressive load from the spring 103 during dialing.

The proximal clicker part 102 is permanently splined to the inner body 20 by external splines 107 which prevent relative rotation with the inner body during both dialing and dispense, providing clicks during dialing and locking the proximal drive sleeve 42 in rotation during dispense. Additional cylindrically shaped splines 108 also couple the proximal clicker part 102 rotationally to the proximal drive sleeve 42 when the button 70 is depressed, this preventing the user from dialing past 80 units with the button depressed. Proximal clicker part 102, in addition to the primary clicker teeth 106, has clutch biasing teeth 109 on the opposite end face. These teeth mate with similar teeth 92 on the clutch to ensure that in the button out position (dialed dose) the clutch is locked in rotation to the proximal clicker part 102 under the biasing action of clutch spring 103.

The cartridge bias spring 110 is assembled as two components one after the other, the lower first and the upper second. The spring combination serves to apply an end load to the cartridge 81 at extremes of tolerance so as to bias it forwards onto the end face of the ferrule in the cartridge holder 80. This ensures that when the user removes and attaches a needle, the friction between the needle cannula and septum of the cartridge does not move the cartridge 81 axially relative to the cartridge holder 80. The bias spring 110 also acts to provide a force against which the user has to connect the cartridge holder 80 and this may add to the tactile feedback of this bayonet joint. The spring 100 also serves to eject the cartridge holder 80 if the cartridge holder is not rotated into a secure position, highlighting this error to the user. The bias spring (system) serves as a cartridge bias system in the device 1.

The cap 120 serves to protect the cartridge holder 80 from damage and the cartridge 81 itself from dust dirt ingress on to the area around the septum. The cap is designed to accommodate a standard pen injector needle.

The window insert 230 may include a lens to magnify the dose numbers e.g. by approximately 25% from their printed size. The window insert 230 may be back printed to protect the printed surface from abrasion and also to maximize the light entering through the window aperture, giving uniform illumination of the dose numbers and white area around these numbers. Arrows may be printed adjacent to the window aperture that indicate the dose dialed.

In the following, the function of the drug delivery device and its components will be explained in more detail with reference to FIGS. 17 to 19.

To use the device, a user has to select a dose. In the start (at rest) condition as shown in FIG. 17 the display mechanism or member 60 indicates the number of doses dialed to the user. The number of dialed units can be viewed through the dose window 230 in the outer body 10. Due to the threaded engagement between the display mechanism or member 60 and the inner body 20 rotation of the button 70 in a clockwise fashion causes the display member or mechanism 60 to wind out of the device and incrementally count the number of units to be delivered. FIG. 18 shows an intermediate stage of dialing (e.g. 7 of 80 units).

During dose setting button 70, driver 40 and display mechanism or member 60 are rotationally locked together via clutch 90. Further, button 70, driver 40 and display mechanism or member 60 are axially coupled. Thus, these three components wind out of the outer housing 10 during dose setting. Clockwise rotation of the button 70 causes the driver 40 to rotate and in doing so it advances along the piston rod 30 which remains fixed throughout dialing. The clicker arrangement 100 provides tactile and audible feedback to the user when dialing doses. At the maximum settable dose of 80 units, the stop features 12 and 67 engage to prevent further dialing.

The last dose nut 50 provides the function of counting the number of dispensed units. The nut 50 locks the device at the end of cartridge life and as such no more drug can be dialed by the user. The last dose nut 50 and the driver 40 are connected via a threaded interface as explained above. Further, the last dose nut 50 is assembled into splines 22 such that the nut 50 and the inner body 20 are rotationally locked together (at all times). Rotation of the driver 40 during dialing causes the nut 50 to advance along the thread 44. The nut 50 is free to slide axially within the inner body 20 at all times which allows advancement of the nut. The change in pitch of thread 44 shown in FIG. 9 towards the final doses axially accelerates the advancement of the nut 50 towards the end of cartridge life lockout condition. At the end of life condition, the stop features 51 of the last dose nut 50 contact the corresponding features 45 on the driver 40. The splined contact with inner body 20 reacts any torque transmitted by these stop features 45.

With the desired dose dialed, the device 1 is ready for dose dispensing. This basically requires pushing button 70 which will result in a disengagement of the clutch 90 from dial sleeve 62 thus allowing relative rotation between the display mechanism or member 60 and the button 70. In all conditions the driver 40 and the button 70 are rotationally locked together by engagement of arms 73 and fingers 48 and by splines 91 engaging corresponding splines on proximal drive sleeve 42. Thus, with the clutch 90 disengaged (button 70 pushed in) button 70 and driver 40 are rotationally locked together with the button 70, the driver 40 and the display mechanism or member 60 still being axially coupled.

When dispensing a dose, the button 70 and clutch 90 are moved axially relative to the mechanism compressing the clutch spring 103. Because the proximal clicker part 102 is splined to the inner body 20 and the axial load passing through the clicker teeth 105, 106 locks the distal clicker part 101 in rotation to the proximal clicker part 102, the mechanism is forced to move axially whilst the dial sleeve 62 and number sleeve 61 are free to spin back into the outer housing 10. The interaction of mating threads between the piston rod 30, driver 40 and inner body 20 delivers a mechanical advantage of 2:1. In other words, axially advancing driver 40 causes the piston rod 30 to rotate which due to the threaded engagement of piston rod 30 with the inner body 20 advances the piston rod. During dose dispensing dispense clicker 68, 71 is active which involves button 70 and display mechanism or member 60. The dispense clicker provides primarily audible feedback to the user that drug is being dispensed.

The end of this step is shown in FIG. 19. At this point the dose is complete and when the user removes the force from the end of the dose button 70, the clutch spring 103 pushes this dose button 70 rearwards, re-engaging the teeth 65 and 95 between the clutch and the dial sleeve.

Resetting the device starts with removal of the cartridge holder 80 and replacing an empty cartridge with a full cartridge 81. As the cartridge holder is re-attached, the bung of the new cartridge contacts bearing 31, thus pushing piston rod 30 back into the housing. Initially, the piston rod 30 screws into the inner body 20, thereby axially disengaging the coupler 43 from the proximal drive sleeve 42 against the biasing force of spring 103. Once disengaged the coupler 43 is free to start rotating together with distal drive sleeve 41 and continues to do so as the cartridge holder 80 is moved axially into engagement with the inner body 20. Thus, the distal drive sleeve 41 rotates with respect to the proximal drive sleeve 42 which is still rotationally constrained in inner body 20 as clicker parts 101 and 102 are pressed together by compressed spring 103. As the distal drive sleeve 41 rotates, last dose nut 50 is reset to its (distal) start position. Coupling the cartridge holder 80 to inner body 20 backs off the mechanism due to the bayonet structure 23 allowing re-engagement of the proximal drive sleeve 42 with coupler 43 and thus the distal drive sleeve 41.

The drug delivery device 1 which has been described above has proven to have a reliable functionality and is also well regarded by users. Furthermore, development and providing the production capabilities is costly, for example on account of the molding tools required for manufacturing the moldable plastic products or the assembling tools or devices required to (semi-)automatically assemble the devices. Moreover, the regulatory processes for approval of a general device architecture may already have been performed and it might be useful to re-use the general architecture of the device, including the dose setting and drive mechanism, to an extent which is as great as possible. Thus, it is desirable to provide a modified drug delivery device, which reuses as many parts as possible from an existing device, for example the one described above, and adjust the dose setting and drive mechanism to a different drug or drug formulation in the cartridge, to cartridges of different filling levels or volumes and/or to different cartridge geometries. When doing so, especially for reusable or resettable drug delivery devices, it should be taken into account that additional security measures are necessary. For example, it should be avoided that the drug for which one of the devices has been designed can be used in conjunction with the other device, as the driving functionality may require an adjustment in the axial displacement of the piston rod for a given dose setting movement between different devices. Thus, for two drug delivery devices with different drugs or drug formulations, the axial displacement of the piston rod relative to the housing may be different. Moreover, the dimensions of the cartridges of the devices may be different as may the filling level or volume and/or the drug or the concentration of drug in the cartridges, even if the same drug is used.

Hereinabove and below, some concepts are disclosed, which facilitate adjusting or modifying one drug delivery device such that different drugs or drug formulations and/or drugs from cartridges having different dimension or volumes may be dispensed by drug delivery devices having similar architectures and/or the same outer appearances with only selected parts being modified in the devices.

A length difference between the two cartridges may be greater than or equal to one of the following values: 1 mm, 2 mm, 3 mm, 4 mm, 5 mm, 6 mm. A difference in diameter, e.g. the outer diameter or inner diameter, between the two cartridges may be greater than or equal to one of the following values: 1 mm, 1.5 mm, 2 mm, 2.5 mm. The relevant diameter may be the maximum outer or inner diameter. The diameter may be the radial dimension of the proximal opening of the cartridge. The difference in length between the cartridges may be less than or equal to one of the following values: 10 mm, 9 mm, 8 mm, 7 mm. The difference in diameter may be less than or equal to one of the following values: 5 mm, 4 mm, 3 mm. The volume of the cartridge with the greater volume, e.g. the filling volume in an initial state of the cartridge, when the entire liquid is still containing the cartridge, maybe greater than or equal to the volume of the lower volume cartridge multiplied by one of the following factors: 1.2, 1.3, 1.4, 1.5, 1.6, 1.7, 1.8, 1.9, 2.0. The cartridge with the lower dimension, e.g. length, diameter and/or volume, preferably has a higher concentration of drug than the one with the greater dimension, e.g. two times or more such as three times the concentration of the drug in the lower dimension cartridge.

In the following text, the concepts are disclosed merely as an example for two drug delivery devices, where one uses a 3.0 mL cartridge and the other one uses a 1.5 mL cartridge. The 1.5 mL cartridge has a higher drug concentration than the 3.0 mL cartridge. For example, the concentration in the 1.5 mL cartridge may be more than twice, e.g. three times the one in the 3.0 mL cartridge. Standard 3.0 mL cartridges may have an outer diameter of 11.4 mm, an inner diameter of 9.6 mm, and a length of 64 mm. Standard 1.5 mL cartridges may have an outer diameter of 8.65 mm, an inner diameter of 6.85, and a length of about 58 mm. It should, however, be appreciated that other dimensions can be applied as well.

The concepts discussed herein of course do also work with other configurations, where different drugs or drug concentrations and/or cartridges of different filling levels or volumes and/or different dimensions are used and similar device architectures should be used, than the ones which are discussed below. The cartridges in the different devices even may have the same dimensions, e.g. length, inner diameter, outer diameter, filling level, and/or volume, but may be provided with different drugs or drug formulations. Although the concepts are described in conjunction with the injection pen discussed earlier, which is a reusable drug delivery device where the dose dispensing force is entirely provided by the user, it should be appreciated that this disclosure also covers semi-automatic drug delivery devices, auto-injectors, and/or disposable devices as well. If the drug delivery device is a disposable device, either the cartridge holder of the cartridge unit is permanently connected to the housing or the cartridge is arranged in the cartridge retaining section of a unitary housing, which houses the dose setting and drive mechanism and the cartridge.

In the following, embodiments of cartridge units are discussed, which are particularly suitable for a set or arrangement of drug delivery devices of the same device architecture, e.g. with respect to the general principles of operation of the dose setting and drive mechanism and/or the outer dimensions and/or shape of the devices. In conjunction with the FIGS. 20A through 21B, embodiments of cartridge assemblies as cartridge units are disclosed. In each case, fixing features are integrated into the cartridge holder of the unit. Before the specifics of the respective embodiments are disclosed, features which may apply to all embodiments are discussed. FIGS. 20A through 20F, as well as 21A and 21B each illustrate one embodiment of a cartridge assembly. The figure denoted with "A", in each case shows a schematic perspective view of the cartridge assembly, where in the figure denoted with "B" only the distal region, i.e. the part of the assembly close to its distal end, is shown.

The cartridge assembly 300 comprises a cartridge 301 and a cartridge holder 302. The cartridge holder 302 may correspond to cartridge holder 80 discussed further above and the cartridge 301 to the cartridge 81. The cartridge 301 is arranged within a cartridge holding or retaining section 303 of the cartridge holder. The cartridge retaining section is expediently delimited by an inner wall 304 of the cartridge holder 302, preferably circumferentially. The cartridge holder 302 has an opening 305. The opening 305 is expediently a proximal opening. The proximal opening may provide access to the interior of the cartridge holder from the proximal end of the holder. Via the opening 305, the cartridge 301 can be inserted into the cartridge holder. A dispensing end 306 of the cartridge may be inserted or introduced into the cartridge through the opening 305. The opposite end of the cartridge holder is the distal end of the cartridge holder 302, which may be that end which is arranged closest to the dispensing end 306 of the cartridge 301. The distal end of the cartridge holder is preferably designed to retain the cartridge in the holder, e.g. by abutment, such that the cartridge may only leave the cartridge holder through the opening 305. The axial extension of the cartridge holder is expediently chosen so as to cover at least 50%, preferably more than 60% or more than 70% such as more than 80% or more than 90% of the total length of the cartridge. The entire cartridge may be covered by the cartridge holder 302 as depicted in the embodiments.

The end of the cartridge opposite to the dispensing end 306, i.e. the proximal end, is not illustrated explicitly in the figures. This end may be closed by a movable bung or stopper, which is likewise not explicitly illustrated. The bung or stopper may sealingly close a proximal opening of the cartridge. A drug 307 or medicament is contained in that region of the cartridge which is arranged between the dispensing end and the bung. Drug or medicament may be dispensed through the dispensing end 306 from the cartridge, if fluid communication between the interior of the cartridge and the exterior is provided and the bung is moved towards the dispensing end. The amount of drug 307 or medicament in the cartridge is preferably sufficient for a plurality of doses, where the size of the dose may be set by the user or may be fixed, e.g. by the design of the drive mechanism used to deliver the drug from the drug delivery device which comprises the cartridge.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

On the side of the dispensing end 306, the interior of the cartridge which holds the drug or medicament 307 is sealingly closed by a septum 308. The septum 308 may be retained at or fixed relative to a cartridge body 340 of the cartridge by means of a septum retainer 309. The septum 308 is expediently pierceable, e.g. via a needle, which may provide fluid communication between the interior of the cartridge and the exterior. The septum retainer 309 may be formed by a cap, e.g. a metal cap, such as an aluminum cap. The metal cap may be connected via clamping or crimping to the cartridge body 340. The body of the cartridge may be formed of glass. The body 340 may define the outer contour of the cartridge. In the region of the dispensing end 306, where the needle should penetrate the septum, an opening is provided in the septum retainer 308 to allow the needle to pass through the region of the septum retainer. The cartridge 301 comprises a head portion 310 and a main body portion 311. The head portion 310 is arranged on the side of the dispensing end 306. The main body portion 311 may be arranged closer to the proximal end of the cartridge than the head portion 310. Between the head portion 310 and the main body portion 311 a neck portion 312 may be arranged. The main body portion 311 may be that region, where the bung or stopper may travel. The main body portion has a tubular configuration. The neck portion 312 may have a reduced diameter, outer and/or inner diameter, as compared to the main body portion 311. The head portion 310 has a reduced diameter, outer and/or inner diameter, as compared to the main body portion 311. The neck portion 312 has a reduced diameter as compared to the main body portion and also with respect to the head portion 310. The diameter may be the extension of the cartridge in a direction perpendicular to the main longitudinal axis of the cartridge or the cartridge assembly which extends between the proximal end and the distal end. The neck portion may extend circumferentially. The entire cartridge 301 may be rotationally symmetric relative to the main longitudinal axis. The transition between the head portion 310 and the neck portion 312 may be formed via a comparatively steep surface, which is preferably less inclined relative to the radial direction than the surface which is provided between the neck portion 312 and the main body portion 311. Accordingly, the transition between the neck portion 312 and the main body portion 311 may be less steep than the one between the head portion 310 and the neck portion 312. Specifically, a cartridge surface 313, which may delimit the head portion 310 proximally, may have an inclination relative to the radial direction which is less than the inclination of a shoulder surface 314 which delimits the main body portion distally. The cartridge surface may be formed by the septum retainer 309 or, alternatively by the cartridge body 340. The septum retainer 309 may clamp the septum to the cartridge body. Thus, the septum retainer may extend from the distal end along the cartridge to a surface of the neck portion of the cartridge body facing away from the distal end of the cartridge and extending in the radial direction to clamp the septum 308 to the cartridge body. The cartridge may comprise or consist of the cartridge body 340, the septum 308, the septum retainer 309, the drug or medicament 307, and/or the bung (not explicitly illustrated).

The cartridge holder 302 comprises on that end opposite of the opening 305 and/or closest to the dispensing end 306 of the cartridge, i.e. its distal end, a distal end wall 315. The distal end wall may extend circumferentially in a ring-like fashion. A proximal surface of the distal end wall 315 is arranged to abut the distal end face of the cartridge 301. In this way, the cartridge 301 can be retained in the cartridge holder without moving distally relative to the cartridge holder 302. The distal end wall 315 may define an opening 316 in the cartridge holder. The end wall may extend around the opening such that the opening is a central opening in the end wall. The opening may extend axially through the end wall 315. The opening 316 may be provided such that a needle can be guided through the opening towards the cartridge, in particular towards the septum 308.

The cartridge holder 302 may comprise a distal region 317 and a main body region 318. The distal region 317 is arranged closest to the dispensing end of the cartridge and/or to the distal end wall 315 of the cartridge holder. The main body region 318 is arranged further away from the distal end or the distal end wall 315 and/or closer to the opening 305 than the distal region. As compared to the main body region the distal region may have a reduced outer diameter. The reduction may be determined by the reduced diameter of the head portion as compared to the diameter of the main body portion of the cartridge. The main body region 318 and the distal region may be connected by an inwardly directed shoulder region 331. In the distal region a needle connector 319, for example a thread may be arranged. Via the needle connector, a needle unit, for example a hub of a needle unit may be secured to the cartridge holder 302. A needle retained in the needle hub may be guided through the opening 316, pierce the septum 308 and provide fluid communication to the interior of the cartridge to dispense drug or medicament 307 from the cartridge 301. The distal region 317 may be designed to receive the head portion 310 of the cartridge 301 in its interior. The main body region 318 may be designed to receive the main body portion 311 of the cartridge. On the side of the proximal end the cartridge holder may have a connection or interface region 320. In that region, connection or interface features may be provided, which are configured to cooperate with corresponding features on a housing 10 to connect the cartridge assembly 300 to the housing to form a drug delivery device 1. The connection features may be designed for a threaded or a bayonet connection between cartridge holder and housing. This has already been described above in conjunction with FIGS. 1 through 19 and will be discussed in more detail below. Preferably, the connection or interface features are coded to a housing which houses a drive mechanism designed for the drug contained in the cartridge of the cartridge assembly. The coding ensures that only a correct cartridge assembly can be assembled to the housing to form a drug delivery device. In this way, it can be guaranteed that the drug in the cartridge assembly is dispensed using a drive mechanism which is specifically designed to dispense the content of the cartridge. The drive mechanism may comprise a piston rod, which is arranged to drive the bung or stopper distally relative to the cartridge, if drug or medicament should be dispensed from the cartridge. An embodiment of a potential coding, which could be applied for the cartridge holder is discussed in more detail further below.

Between the proximal end and the distal end of the cartridge holder 302, preferably closer to the proximal end than to the distal end, a radially outwardly protruding step 321 or flange, may be provided. The step or flange 321 may extend over the entire circumference of the cartridge holder 302. A proximal surface of the step 321 may be arranged to contact a distal surface of the housing when the cartridge assembly is connected to the housing. The connection region 320 may be covered by the housing, when the assembly has been connected to the housing. The main body region 318 and the distal region 317 may, however, protrude from the housing.

Furthermore, the cartridge holder 301 comprises at least one fixing feature 322. As seen along the axial direction, the fixing feature 322 is provided between two interior regions of the cartridge holder, where one is adapted to receive and retain the head portion 310 and another one is adapted to receive and retain the main body portion 311 of the cartridge. The fixing feature 322 may extend in the region of the neck portion of the cartridge 301. The fixing feature 322 protrudes radially from an inner wall of the cartridge holder 301. Preferably, the fixing feature 322 reduces the inner diameter the cartridge holder such that in that region, the inner diameter is less than the outer diameter of the head portion of the cartridge.

Therefore, if the head portion of the cartridge should be guided axially past the fixing feature from the proximal opening, the fixing feature has to be deflected radially outwardly, e.g. displaced only radially. If the fixing feature is deflected, the head portion can pass the fixing feature. Preferably, the fixing feature is deflected by means of the head portion cooperating with a proximal surface of the fixing feature which may be oblique, i.e. neither perpendicular nor parallel, with respect to the main axis of the cartridge holder. After the head portion has passed the fixing feature, the fixing feature may move radially inward again, e.g. resiliently. The interior region of the cartridge holder which is designed to receive the head portion 310 may have a reduced diameter as compared to that region which receives the main body portion 311.

The fixing feature 322 is formed integrally, e.g. by injection molding, with a section of the cartridge holder which defines an exterior surface or at least the outer contour of the cartridge holder. That is to say, if applicable the cartridge holder may be provided with a coating on the exterior surface whereas the outer contour may still be defined by the section of the cartridge holder the fixing feature is integrated into. In FIGS. 20A and 21A, an injection gate mark 323 is shown, which indicates the position where the fluid plastic compound is injected into a mold cavity which defines the shape of the cartridge holder. The injection gate mark 323 is positioned in the region of the distal end wall 315 of the cartridge holder, particularly on a distal face of the distal end wall.

The fixing feature 322 comprises a fixing surface 324. The fixing surface 324 may be a distal surface of the fixing feature. Preferably, the fixing surface is radially oriented, i.e. it extends in the radial direction, and/or plane. The fixing surface 324 is arranged to abut or abuts a proximally facing surface of the cartridge, such as the cartridge surface 313. Thus, the cartridge surface 313 and the fixing surface 324 are arranged to prevent that the cartridge is removed proximally from the cartridge holder through the opening 305 by mechanical cooperation with one another. Accordingly, removal of the cartridge from the holder through the opening 305 is prevented by means of the fixing feature 322. The fixing feature 322 may be formed as a snap and/or clip feature. The angular extension of the fixing feature or the fixing surface may be less than or equal to one of the following values: 20°, 15°, 10°.

Furthermore, an outer wall of the cartridge holder is provided at the axial position of the fixing feature. Thus, the cartridge holder is closed at least in the region of the fixing feature. Accordingly, the fixing surface and/or the fixing feature cannot be accessed from the outside. This reduces the chances that the cartridge assembly can be tampered with.

In the following, some embodiments of cartridge holders with fixing features integrated into the cartridge holder are discussed in more detail. The embodiment depicted in FIGS. 20A through 20F, has one fixing feature 322, in particular just one. Of course, a plurality of fixing features could be provided as well. Such an embodiment is shown in FIGS. 21A and 21B and is very similar to the one of FIGS. 20A through 20F.

The fixing feature 322 protrudes radially from the inner wall 304 of the cartridge holder 302. The fixing feature 322 is arranged in the interior of the distal region 317 of the cartridge holder 302 and, particularly, in the interior region of the cartridge holder where the needle connector 319 is provided on the exterior. As is apparent from FIG. 20A and also from FIG. 20B, the distal end wall 315 which has a generally ring-like configuration, has an opening 325. The opening 325 is radially oriented and interrupts the ring defined by the distal end wall 315. The opening 325 extends radially outwardly from the opening 316. The angular and radial position of the opening 325 may correspond to the one of the fixing feature 322 or the fixing surface 324, where the opening is axially offset from the fixing feature, e.g. in the distal direction. Particularly, as seen from the distal end along the axis, the fixing surface may be visible from the distal end. The fixing surface may be framed radially and angularly by sidewalls which delimit the opening 325. In the figures, the head portion 310 of the cartridge 301 is arranged between the opening 325 and the fixing surface 324. The angular dimension and/or the radial dimension of the opening 325 may define, may correspond to or may be greater than the angular dimension and/or the radial dimension of the fixing surface and/or the fixing feature. Providing an opening in the region of the distal end facilitates molding of the cartridge holder with the integrated fixing feature with only minor modifications to the mold or molding tool as compared to a cartridge holder without fixing features. In a cartridge holder without a fixing feature, two core pins of different diameters may be used for producing the cartridge holder by injection molding, where one core pin defines the interior of the distal region and one core pin defines the interior of the main body region 318 of the cartridge holder. A short core pin may define the interior in the distal region and a long core pin may define the region of the interior in the main body region. The fixing feature 322 may be integrated right at the intersection or the boundary of the two different core pins of the injection molding tool. The opening 325 may be formed during the molding process and facilitates the molding of a cartridge holder with the fixing features 322 integrated into it. The opening 325 may be defined by a protrusion, e.g. of metal, on the short core pin.

In the region where the fixing feature is provided, e.g. the distal region 317, the cartridge holder may be radially deformable. Thus, the inner diameter may be increased when the cartridge holder is exposed to a radially outwardly directed force. The capability of the cartridge holder to be radially deformed when exposed to a radially directed force may be increased in that angular section of the distal region 317 which overlaps angularly with the opening 325. The fixing feature 322 is arranged in this region as it overlaps angularly with the opening. The fixing feature is expediently non-flexible and/or rigid, e.g. more rigid than the distal region 317 or the inner wall of the first region where the head portion of the cartridge is to be arranged. Thus, when an axial and/or radial force acts on the fixing feature, e.g. while the head portion is guided along and in contact with the fixing feature, the cartridge holder is widened on account of the rigidity of the fixing feature 322. The fixing feature itself is not deformed or flexed. After the head portion 310 has passed the fixing feature 322, the fixing feature is displaced inwardly again and the cartridge surface 313 and the fixing surface 324 are arranged as depicted in FIG. 20B. The fixing feature is preferably not deformed during this process and, in particular, not axially deflected or pivoted.

As shown in FIG. 20B, distally offset from the fixing surface 324, a sloped surface 326 which rises radially along its extension in the distal direction, is arranged. By means of this surface, which is preferably arranged at the opposite side of the fixing surface or at least angularly offset from the fixing surface, a radial movement of the head portion 310 of the cartridge 301 may be achieved to a region overlapping radially with the fixing surface 324. Thus, the sloped surface acts as a cartridge guiding feature during the assembling process of the cartridge assembly 300. References to the sloped surface 326 may therefore be regarded as references to the cartridge guiding feature and vice versa. The radial overlap of the fixing surface 324 and the surface 313 of the cartridge 301 when the cartridge has reached its final position may be increased in this way. The sloped surface 326 may strengthen the stability of the securing of the cartridge in the cartridge holder, e.g. in case only one fixing feature is provided.

The distal offset (highlighted with "B" in FIG. 20B) of the cartridge guiding feature 326 from the fixing feature, from the fixing surface 324 and/or from a radial free end of the fixing feature 322 may be greater than the thickness (highlighted with "A" in FIG. 20B) of the septum 308 of the cartridge. This ensures that the septum retainer 309 is backed by the more rigid cartridge body 340 and preferably not by the septum, when the cartridge interacts with the fixing feature 322 to radially displace the feature outwardly in order to temporarily widen the interior of the cartridge holder. Thus, the force required to displace the feature 322 is not transferred to the septum. If the force were transferred to the septum, the risk that the septum retainer 309, which may be a thin metal component, is deformed or the septum is damaged is considerably increased. This can be avoided by the distal offset between cartridge guiding feature 326 and the fixing surface 324 by more than the thickness of the septum 308. The distal offset B is expediently less than the axial extension of the head portion 310 of the cartridge. In this way, the cartridge guiding feature may properly guide the cartridge 301 radially inwardly by cooperating with the head portion 310.

In the region of the interior of the cartridge holder 302 between the cartridge guiding feature 326 and the fixing surface 324, the inner diameter of the interior of the cartridge holder may be greater than in the region of the cartridge guiding feature and/or in a region distally offset from the cartridge guiding feature, if such a region is present which it may be or may not be. In the region of the interior of the cartridge holder between the cartridge guiding feature and the fixing surface the inner diameter may be greater than the inner diameter in the fixing feature region. In the region of the cartridge guiding feature 326 and/or distally with respect to the cartridge guiding feature, the inner diameter of the cartridge holder may be greater than the inner diameter in the fixing feature region, e.g. greater than or equal to the outer diameter of the head portion 310.

In other words, the septum retainer or metal sleeve 309 has a distal section which surrounds the soft septum 308, and a proximal section that surrounds the neck of the cartridge body or glass ampoule 340. It is advantageous if the distal section of the septum retainer has moved past the fixing surface 324 before the distal section makes contact with the cartridge guiding feature or sloped surface 326. In this way the radial overlapping of the metal sleeve 309 and the fixing surface is minimal during the period of assembly where the fixing surface could damage the metal sleeve 309, and this overlapping is only increased when the fixing surface has moved past the distal section of the metal sleeve 309 and is applying radial pressure to the proximal section. As the proximal section is supported by a harder, e.g. glass like, material than the distal section it will not be damaged or indented. The final overlapping between the fixing surface and the cartridge surface at the end of assembling process is still high. The final overlap may be defined by the smaller inner diameter of the cartridge holder in the region of the sloped surface which marks the end of the sloped surface 326.

When a cartridge holder 302 with an integrated fixing feature 322 was tested, it has been discovered, that the distal section of the septum retainer 309 dents badly unless the diameter prior to sloped surface 326 is sufficiently larger than the diameter after slope 326 so that the cartridge 301 can move away from the fixing feature with minimal, if any, interference in the distal section of the septum retainer and that this interference only increases after the fixing feature is pressing in the region of the septum retainer 309 where the head portion of the cartridge body, e.g. of glass, backs up/supports the septum retainer, which may be a thin and easily deformable metal component.

When the cartridge 301 has been assembled into the cartridge holder 302, the fixing feature 322 may block proximal movement of the cartridge 301 relative to the holder 302. The fixing feature, however, expediently does not exert a securing force, e.g. a distally or radially directed force, onto the cartridge regularly but only prevents removal of the cartridge from the cartridge holder. In this way, the force load onto the cartridge may be advantageously low.

Figure 20C:
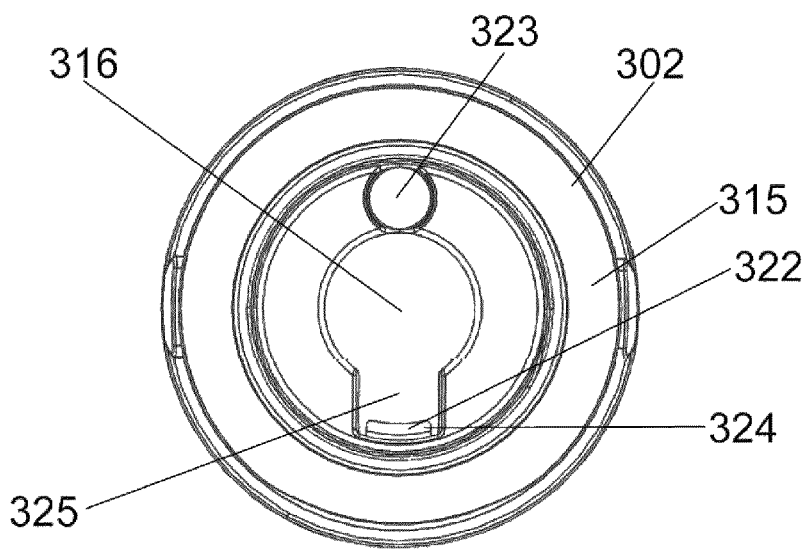
Figure 20D:
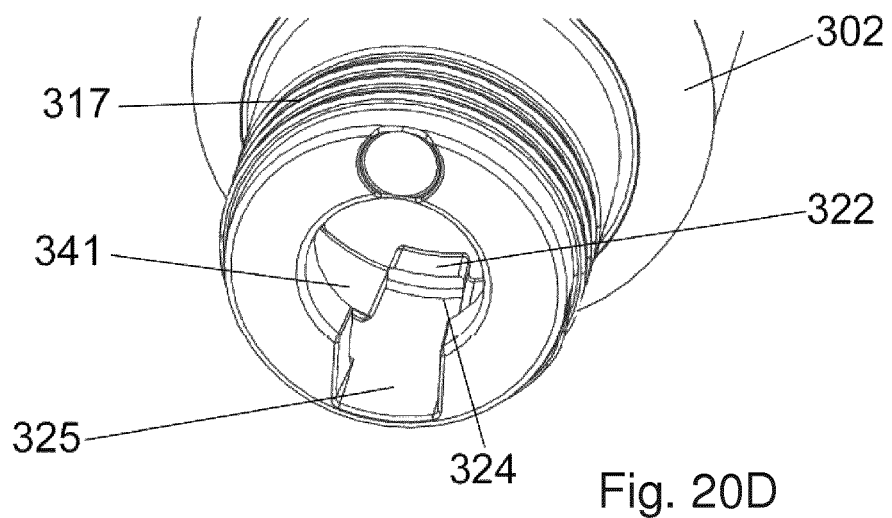
Figure 20E:
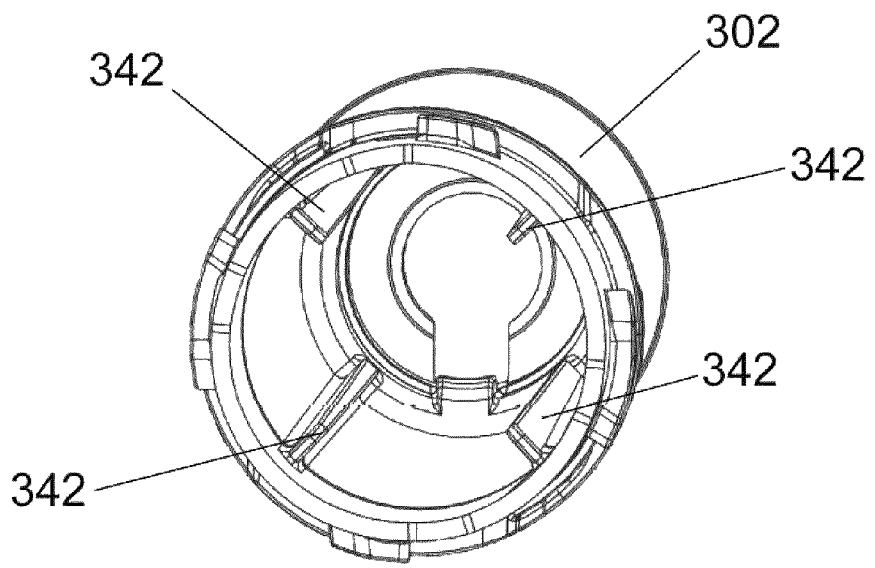

FIGS. 20C through 20F show additional views of the cartridge holder 302. FIG. 20C shows a view from the distal end. As is immediately apparent, the angular dimension of the fixing feature 322 is less than the one of the opening 325. The radial dimension of the fixing feature 322 or the fixing surface is less than the one of the opening 325 as well. From FIG. 20D, which shows the distal end as well but in a perspective view, it can be gathered that the cartridge holder, in particular the distal region 317, is reinforced, i.e. has a higher wall strength or thickness, in a region which is angularly adjacent to the fixing feature 322. A reinforcement section 341 extends circumferentially in the interior of the cartridge holder. The reinforcement section may axially overlap with the fixing feature. The reinforcement section 341 may be arranged distally offset from the fixing feature 322 alternatively or additionally. In the region of the interior of the cartridge holder which angulary overlaps with the fixing feature the reinforcement section is preferably interrupted to promote radial deformability of the cartridge holder when the head portion displaces the fixing feature 322 radially.

Figure 20F:
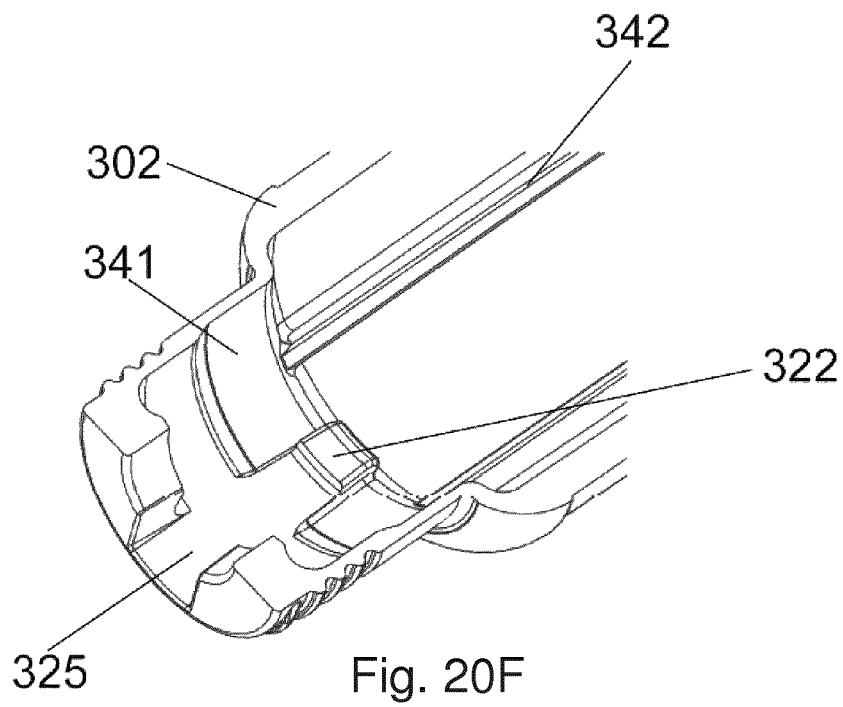

As seen from the opening 325 axially towards the fixing surface 324, the wall thickness of the holder 302 may be less than the wall thickness in the reinforcement section 341. The wall thickness of the cartridge holder 301 in the region of the fixing feature 322 and defined by the fixing feature may be greater than the one in the reinforcement section 341. The fixing feature 322 may radially protrude over the reinforcement section 341. The reinforcement section 341 is also depicted in FIG. 20F which shows a perspective sectional view of the cartridge holder 302. In this figure as well as in FIG. 20E, which shows a view from the proximal end of the cartridge holder 302, it is shown that the interior of the cartridge holder comprises a plurality of circumferentially disposed, preferably equally spaced, spacer features or cartridge support features 342, e.g. ribs. The features 342 are axially oriented. The features 342 may be provided to radially support the cartridge, e.g. the main body portion 311 thereof, if the cartridge is retained in the cartridge holder. These features may be the only difference between a cartridge holder which receives cartridges with a smaller diameter and one which receives a cartridge with greater diameter, if applicable aside from coding structures as discussed further below. The cartridge holder for the larger diameter cartridge may, expediently, not have the cartridge support features 342. Thus, the exterior dimensions of the cartridge holder may be the same although the exterior diameters of the cartridges retained in the cartridge holders are different.

As is apparent from the figures, e.g. from FIG. 20B, the needle connector 319, e.g. a thread, is distally offset from the fixing feature 322. Specifically, the region between the fixing feature and the cartridge guiding feature or sloped surface 326 may be free of the needle connector 319. The needle connector may axially overlap with the cartridge guiding feature 326 or be provided distally offset from this feature 326. Thus, the axial extension of the needle connector 319 may be less than in other cartridge holder designs.

For example, the needle connector 319 may be restricted to a distal section of the distal region 317 of the cartridge holder, where between the needle connector 319 and the main body region a connector-free region is arranged. The axial extension of the connector-free region may be greater than 50% of the axial extension of the distal section with the needle connector. The axial extension of the distal section with the needle connector may be greater than the one of the connector-free region. As the cartridge holder in the region between the fixing feature 322 and the guiding feature 326 has a reduced wall thickness to increase the inner diameter of the cartridge holder 302, e.g. in order to maintain a given outer contour or dimension of the cartridge holder 302, providing an additional radial indentation on the exterior in this region, which would be required for the connector 319, would increase the risk of damaging the cartridge holder in this region or even render it unmoldable. Thus, the shortened needle connector is advantageous.

Although the depicted embodiment shows only one fixing feature, a sloped surface may also be provided in case a plurality of fixing features is used. In the following embodiment, the sloped surface is not shown, however.

In FIGS. 21A and 21B a cartridge holder 302 with two integrated fixing features 322 is shown. The fixing features 322 are oppositely disposed where each fixing feature has a fixing surface 324 which is arranged to abut the cartridge surface 313, which may be formed flange-like. Two openings 325 are provided in the distal end wall 315 of the cartridge holder which interrupt the ring-like shape of the cartridge holder at positions which angularly and/or radially correspond to the position of the fixing surface 324 of the respective fixing feature. The respective opening 325 may be connected to the central opening 316. As explained previously, this assists in integrating the fixing feature into the cartridge holder by injection molding which is particularly easy and a low-cost process, suitable for high volumes. The disclosure above regarding the opening therefore also applies for this embodiment. Still further, more than two fixing features could be provided as well. In FIG. 21B, the needle connector overlaps axially with the fixing feature(s) 322.

As the fixing feature 322 interacts with the head portion in the depicted embodiments, cartridges with differently shaped main body portions may be secured in the cartridge holder easily, e.g. cartridges of different volumes, such as 1.5 mL and 3 mL, different diameters and/or lengths. The head portions of the cartridges may be formed alike.

It should be appreciated that the present disclosure is particularly advantageous for cartridge assemblies with cartridges which are permanently secured therein as cartridge units. However, also cartridge holders with removable cartridges where the cartridge can be replaced in the cartridge holder can be used as cartridge units in the presently disclosed concepts.

Cartridges of different volumes may have different lengths and/or different inner and/or outer diameters. The cartridge assembly may be a disposable item, which is e.g. sold in the pharmacy. Different cartridges of the same or of different volumes may contain different drugs or drug formulations. Cartridges of a smaller volume may have a higher concentration of a drug. If the drug is insulin or an insulin derivative, for example, the cartridge of a smaller volume may have a concentration which is more than 2 times, e.g. 3 times, the concentration of drug or medicament in the larger volume cartridge. The drug in the larger volume cartridge may be formed by the same active pharmaceutical ingredient. Differences in the content between the cartridges may be, preferably only, in the concentrations of the drug within the liquid, i.e. in the specific formulation of the drug. For example, a 3 mL cartridge may comprise 300 IU (IU: International Unit), e.g. of insulin, whereas the 1.5 mL cartridge may comprise 450 IU, which, taking into account the lower volume, corresponds to three times the concentration of drug in the 3 mL cartridge.

As discussed previously, the drug delivery devices may have cartridges of different dimensions. As the device discussed in conjunction with FIGS. 1 through 19 has a cartridge bias system and the outer appearance of the device expediently should stay the same for devices with differently dimensioned cartridges, the cartridge bias system should be modified for the device with a cartridge of smaller length and/or diameter. In the following, embodiments for a modified cartridge bias system are discussed. All of these embodiments use a rigid force transfer body which is applied to take account of the length and diameter variation between the cartridges of the two devices. The device with the larger cartridge, expediently, does not have the rigid force transfer body. Adjusting the cartridge bias system is particularly suitable, if the devices having the cartridges of different dimensions should have the same exterior dimension and/or the portion of the cartridge holder which protrudes from the housing 10 should have the same length in a variety of devices regardless of the dimension of the cartridge employed in the respective device.

Figure 22:
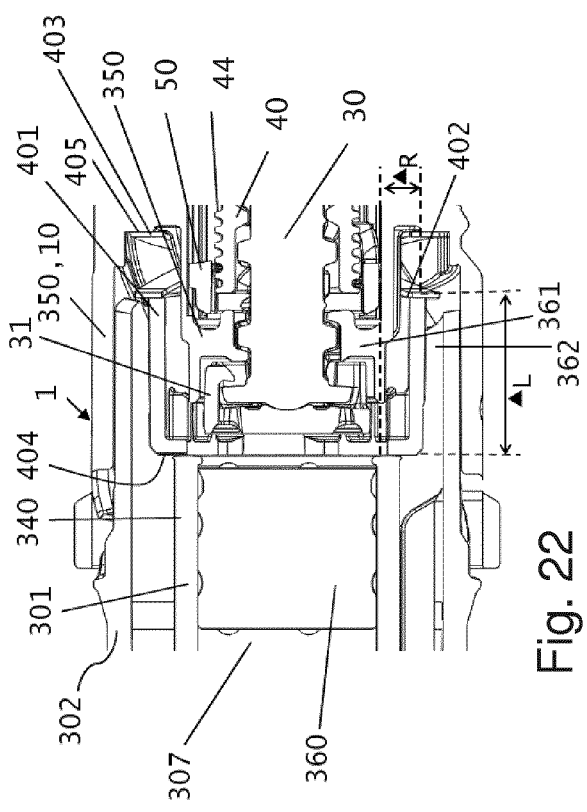
FIG. 22 shows a schematic sectional view of a section or region of a drug delivery device.

In the following, in conjunction with FIGS. 22 through 28B, an embodiment of a cartridge bias system or arrangement is described. As is apparent from the region of the drug delivery device 1 which is shown in FIG. 22, the drug delivery device 1 comprises the cartridge 301, the cartridge holder 302, and a housing part 350. The device may be the device discussed further above or a different device. The cartridge 301 is retained and arranged in the cartridge holder 302. The entire cartridge 301 may be arranged within the cartridge holder 302. The length of the interior of the cartridge holder may be greater than the length of the cartridge. The cartridge 301 may be permanently secured to the cartridge holder 302 such that the cartridge assembly (see the description further above) which comprises cartridge 301 and cartridge holder 302 may form a consumable item. The consumable item may be sold in a pharmacy. The cartridge holder 302 is, preferably releasably, connected to the housing part 350, for example via a threaded or bayonet-type connection. The housing part 350 may be an outer housing of the drug delivery device or an additional part which is, preferably axially and rotationally, locked to a housing 10 of the drug delivery device, preferably the outer housing. The housing part 350 may be the inner body 20 as discussed previously or another housing part. The housing 10 retains components of a dose setting and/or drive mechanism of the drug delivery device 1 as discussed previously. The cartridge 301 holds a drug or medicament 307, preferably a liquid drug formulation. At the proximal end, that is to say that end of the cartridge 301 opposite of the distal end via which the drug 307 can be dispensed from the cartridge, the interior of the cartridge 301 is closed by a movable bung or stopper 360. The bung expediently seals the cartridge proximally. Provided that fluid communication between the interior of the cartridge and the exterior is provided, e.g. by a needle piercing a septum of the cartridge at the distal end (not illustrated), movement of the bung 360 in the distal direction relative to a cartridge body 340 to dispense drug 307 from the cartridge. The drug delivery device 1 is preferably a variable dose device, where the dose of drug which is to be dispensed from the device can be set by the user and is not predefined by the design of the device such as is the case in a fixed dose device. The proximal direction is the direction to the right in FIG. 22 and the distal direction is the one to the left.

The dose setting and/or drive mechanism which is retained in the housing 10 or the housing part 350 comprises the piston rod 30, for example a lead screw. Other types of piston rods could be used as well, e.g. a toothed rod, or the like. The piston rod 30 may be arranged to drive the bung 360 distally relative to the cartridge body 340. The piston rod 30 may rotate relative to the housing during drug delivery. Consequently, as its interface with the bung 360, the piston rod 30 may be provided with a bearing 31, where the piston rod 30 is rotatable relative to the bearing 31 which, may be axially connected or locked to the piston rod 30. Thus, when the bearing 31 contacts the bung 360, rotational movement of the piston rod 30 relative to the bung 360 may still be possible without having to account for the friction between piston rod 30 and bung 360. Of course, alternatively, a piston rod of a different design may also be provided. For example, the piston rod may be only moved axially during dose delivery.

The drive mechanism may furthermore comprise a mechanism which transfers a user exerted force from a button or actuator of the device (not illustrated), which forms the user interface, to the piston rod 30. The drive mechanism may furthermore comprise a drive member or drive sleeve 40. The drive member 40 may be rotatable and/or axially displaceable relative to the piston rod 30 in the proximal direction during dose setting and/or transfer the force to the piston rod which is required to generate a distal movement of the piston rod during dose delivery. The drive member 40 may be coupled to a (last) dose nut 50. An outer surface of the drive member 40 may be provided with a thread 44, which may be engaged to the dose nut 50. The dose nut may act as a follower or tracking member to track how much drug has already been dispensed from the device and, when a final position is reached relative to the drive member, prevent that a dose is set which exceeds the quantity of drug 305 still remaining in the cartridge 301. Thus, the dose nut 50 may be displaced relative to the drive member 40 during dose setting but stay in position relative to the drive member during dose delivery. This results in a displacement of the last dose nut towards an end position relative to the drive member while the cartridge is emptied. In the end position, increasing the dose may be blocked. This indicates that the cartridge is empty. Thus, when the available drug has been dispensed, the cartridge holder may be detached from the housing and a new cartridge assembly or cartridge may be connected to the housing.

The piston rod 30 is, e.g. threadedly, engaged with or guided by a piston rod guide section 361 of the housing part 350 or the housing 10. The piston rod 30 may be threadedly engaged with the housing 10, 350 via one or more thread features provided on an interior surface of the piston rod guide section 361. Accordingly, relative rotation between the piston rod and the housing results in an axial displacement of the piston rod. Thus, the drive member may transfer a force to the piston rod, which causes the piston rod to rotate relative to the housing during dose delivery.

Between the piston rod guide section 361 and an inner surface of the housing or housing part 350, a hollow or space 362 may be formed. The hollow 362 may provide a region, where components of a cartridge bias system can be arranged without interfering significantly with the drive mechanism. The piston rod guide section 361 may have a cylindrical exterior surface.

An embodiment of the cartridge bias system 400 is described in the following. The cartridge bias system 400 comprises a rigid force transfer body 401, e.g. from a plastic material. The cartridge bias system 400 further comprises at least one, expediently separate, resilient member 402 in addition to the rigid force transfer body. The resilient member 402 may be a spring member such as a metal spring member. For example the resilient member 402 is a spring washer. The resilient member may correspond to the spring 110 discussed further above in connection with FIGS. 1 through 19. The rigid force transfer body 401 may be arranged between the at least one resilient member and the cartridge. In the embodiment discussed in conjunction with FIGS. 22 through 28B, the cartridge bias system 400 comprises a second separate resilient member 403. The second resilient member may be a spring member such as a metal spring member, e.g. a spring washer. The spring washers 402, 403 may be arranged such that concavely shaped portions of the washer-like surfaces of the spring washers face one another to maximize axial deformability and/or the force transferable by the cartridge bias system.

Figure 23:
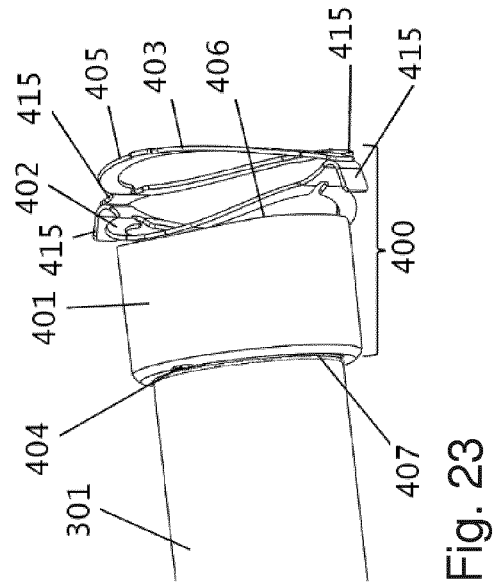
FIG. 23 shows on the basis of a schematic perspective view an embodiment of a cartridge bias system employed in the device.

In the embodiment depicted in FIGS. 22 and 23, the first and the second resilient member 402, 403 are arranged proximally with respect to the rigid force transfer body 401. The force transfer body 401 is, therefore, arranged between the first resilient member and the cartridge and also between the second resilient member and the cartridge. By means of the axially rigid force transfer body, an axially directed force can be transferred from the resilient members to the cartridge in order to bias the cartridge 301 into the distal direction in a defined position relative to the cartridge holder. This enables to maintain the cartridge in the defined relative position and increases dose accuracy.

The cartridge bias system 400 has a cartridge contact area 404. The cartridge contact area is formed by a distal surface area that is to say a surface facing in the distal direction of the cartridge bias system. The cartridge bias system 400 furthermore has a housing contact area 405, where the cartridge bias system contacts the housing. The housing contact area 405 may be formed by a proximally facing surface of the cartridge bias system. The contact areas 404, 405 enable that the cartridge bias system may be mechanically contacted by the cartridge, e.g. by a proximal rim of the cartridge body, and the resilient member or the resilient members may be elastically biased by axially displacing the cartridge relative to the housing during attachment of the cartridge such as by attaching the cartridge holder 302 to the housing part 350 or the housing 10. In the depicted embodiment in FIGS. 22 and 23, the cartridge contact area 404 is formed by the rigid force transfer body 401 and the housing contact area 405 is formed by one of the resilient members 402, 403, e.g. the more proximal one if two resilient members are present or by the resilient member, if only one is present, which is also possible. The rigid force transfer body 400 may be, entirely or only partly, received in the cartridge holder 302. Accordingly, the outer diameter of the rigid force transfer body may be less than the inner diameter of the cartridge holder 302. The opening of the resilient members may have equal inner diameters. The opening of the respective resilient member may have a diameter greater than the outer diameter of the cartridge at the proximal end.

The rigid force transfer body is axially movable relative to the housing, where the resilient member(s) is(are) elastically deformed when it is moved proximally and may relax, when the body moves distally, e.g. when the cartridge is changed. The axial movement of the rigid force transfer body relative to the housing may be constrained, especially in the distal direction and/or in the proximal direction. In the distal direction, this may be done by a stop surface provided on the housing or housing part which prevents the rigid force transfer body from falling out of the housing or housing part when the cartridge holder 302 is disconnected.

The first resilient member 402 may mechanically contact the rigid force transfer body 401, the second resilient member 403 may mechanically contact the first resilient member and be arranged to contact the housing in the housing contact area 405. A force created by deformation of the resilient members when the cartridge pushes the force transfer body proximally, where the force acts in the distal direction, is transmitted to the cartridge via the rigid force transfer body and to the housing by means of one of the resilient members. This keeps the resilient member(s) biased when the cartridge is connected to the housing, where the resilient force is reacted by the housing and the cartridge.

The piston rod 30 may extend through and be guided through the resilient member(s) and the rigid force transfer body 401. Thus, the force transfer body and/or the resilient members can be arranged radially outwardly offset from the piston rod. The force transfer body and/or the resilient member(s) are also preferably arranged radial outwardly with respect to the piston rod guide section 361 of the housing part 350. Expediently, they can be arranged in the hollow 362 defined between the piston rod guide section and an inner surface of the housing. In this way, although the rigid force transfer body 401 is provided, no significant additional packaging space may be required.

The rigid force transfer body is preferably not or not significantly compressible under the regular axially directed force which occur when the cartridge is connected to the housing by the cartridge retainer or holder 302.

The cartridge contact area 404 and the housing contact area 405 may be axially and radially offset. The radial offset may correspond to the difference in radius or diameter between a 3.0 mL cartridge and a 1.5 mL cartridge.

A standard 3.0 mL cartridge has an outer diameter of 11.4 mm and a length of 64 mm and a standard 1.5 mL cartridge has an outer diameter of 8.65 mm and a length of 57.8 or about 58 mm. Accordingly, the radial offset between the cartridge contact area 404 and the housing contact area 405 may be equal to about 1.375 mm.

In case of doubt, the centers of the respective contact area as seen in sectional view perpendicular to the main axis of the device may be taken as origin to determine the distance.

Alternatively, a radial inward end of the housing contact area and a radial outward end of the cartridge contact area may be used to determine the distance.

The rigid force transfer body may form a spacer which is used to adjust an existing mechanism for a drug delivery device to a cartridge having a reduced length and/or diameter such as a mechanism which is designed for a 3.0 mL cartridge to be used in conjunction with a 1.5 mL cartridge. The cartridges may contain the same drugs or drug formulations or different drugs or drug formulations. For example, the 1.5 mL cartridge may contain the same drug but in a different concentration, e.g. insulin in a higher concentration than the 3.0 mL drug. Thus, in the depicted embodiment, the cartridge may be a 1.5 mL cartridge. If a 3.0 mL cartridge is employed, the rigid body may be dispensed with or a shorter body may be employed.

By means of the dimensions of the rigid force transfer body 401, the difference between the length and the diameter of the 1.5 mL cartridge and 3.0 mL cartridges can be compensated. In FIG. 22, the difference in radius (which is half the diameter) is illustrated by $\Delta_R$ and the difference in length is illustrated by $\Delta_L$. The length of the force transfer body may be determined by the length difference between the 3.0 mL cartridge and the 1.5 mL cartridge or be greater. However, the axial separation between load transfer or interface surfaces of the body, where the body interfaces with another element, e.g. a resilient member on the proximal side and with the cartridge on the distal side, is expediently equal to the length difference even if the body itself has a greater length.

Consequently, apart from the force transfer body, the cartridge bias system can stay the same, especially the springs need not to be re-dimensioned. The inner diameter of the opening in the resilient member(s) may correspond to the one of a 3.0 mL cartridge, such that the respective member could be used to abut a proximal end of the cartridge body of the 3.0 mL cartridge. Thus, components which have proven their function in a 3.0 mL cartridge device can be reused in conjunction with a 1.5 mL cartridge device. The outer appearance of the devices may stay the same regardless of the cartridge retained therein. The inner diameter of the opening in the resilient member(s) may correspond to the one of a 3.0 mL cartridge, such that the respective member could be used to abut proximal end of the 3.0 mL cartridge.

The requirement to provide sufficient biasing force for a range of deformation values, e.g. resulting from variations in manufacturing tolerances, means that a minimum quantity of energy must be stored within the resilient elements of the biasing arrangement or system. This energy storage requirement will be more easily met with large diameter springs rather than small diameter springs due to the larger volume of metal that may be included. The additional diameter available also potentially reduces the axial space requirements of the biasing arrangement. In a typical pen injector, packaging space will be at a premium close to the axis of the device due to the presence of the dispensing or drive mechanism (e.g. bearing, piston rod, piston rod guide section, drive member and/or last dose nut). The use of a spacer or rigid force transfer body to 'step out' to a larger diameter allows the use of metal bias springs which are of larger diameter than the aforementioned components. This allows the cartridge biasing arrangement to wrap around the aforementioned components rather than requiring that an axial gap be introduced between them. This advantage is independent of whether the device is adjusted to a differently shaped or dimensioned cartridge or not.

Figure 25:
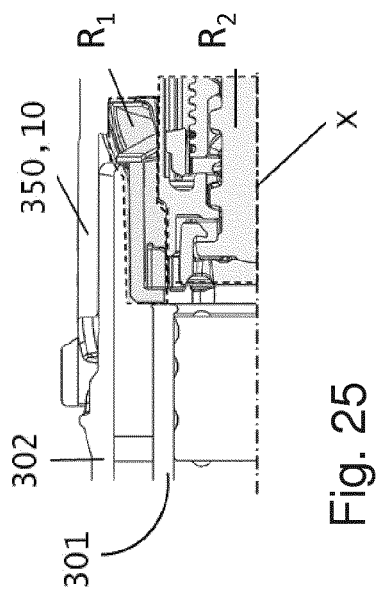
FIG. 25 shows a part of a section of FIG. 22 with highlighted areas.

FIG. 25 illustrates that the cartridge bias system can be constrained to a region outside of the one where elements of the drive mechanism or guiding elements associated with elements of the drive mechanisms are arranged. Specifically, the shaded region "$R_1$" is the one where the bias system is arranged and the region "$R_2$" is the one where the drive mechanism is arranged. For simplicity, only the upper half of the device 1 is shown in FIG. 25, where the device may be symmetric with respect to the main longitudinal axis X of the device.

Figure 24:
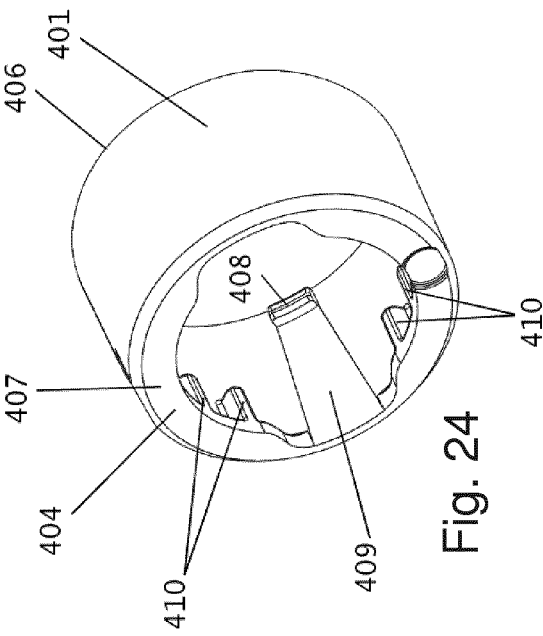
FIG. 24 shows a component of the cartridge bias system, a rigid force transfer body, on the basis of a perspective view.

To compensate for the length difference between different cartridges, the axial distance between load transfer surfaces of the rigid force transfer body should be determined by or equal to the length difference. In the embodiment shown in FIG. 24, the distal load transfer surface 407 of the force transfer body 401 is formed in the area of the cartridge contact area 404. However, as will be shown below, the force transfer body need not immediately abut the cartridge such that the cartridge contact area and the distal load transfer surface do not have to coincide. The proximal load transfer surface 406 may be formed by the proximal end of the force transfer body, which may be that end, which is mechanically abutted by the first resilient member 402. As depicted in FIG. 24, the force transfer body 401 has a sleeve-like shape. A flange at the distal end, which is inwardly directed, may provide the load transfer surface 407 and/or the cartridge bearing area 404.

As already discussed previously, the force transfer body 401 is expediently assembled to the housing or the housing part 350. For this purpose, one or more connection features 408 are provided. In FIG. 24 only one connection feature 408 is shown, although a plurality are preferably provided. For example, at the diametrical opposite position for the depicted connection feature, another connection feature 408 may be provided. Also, more than two connection features 408 may be provided, which are preferably uniformly distributed in the angular or azimuthal direction.

The respective connection feature 408 may be a snap or clip feature. In order to provide for flexibility, in the radial direction, the flange may have a reduced radial extension in an area angularly overlapping with the connection feature 408, but axially separated therefrom. alternatively or additionally the wall thickness of a sidewall of the body 401 may be reduced in an which is angularly aligned with the connection feature in order to increase flexibility. Thus, a recess 409 may extend axially away from the connection feature in the proximal and/or distal direction. In FIG. 24, only a distally extending recess 409 is shown.

The connection feature may extend radially inwardly from the force transfer body into the opening of the body through which the piston rod may extend. The force transfer body furthermore comprises guide or stabilization features 410, e.g. ribs extending in the axial direction. A radially inwardly facing surface of the respective guiding or stabilization feature may bear against the radially outwardly facing surface of the housing part 350, e.g. an outward surface of the piston rod guide section 361 in order to radially stabilize the positon of the force transfer body 401 when assembled. Accordingly, the guide features 410 expediently abut the housing when the cartridge holder with the cartridge has been disconnected from the housing and/or when the cartridge holder has been connected to the housing. Specifically the guide features may cooperate with the housing in any axial position of the force transfer body relative to the housing when the body has been assembled to the housing. By means of the connection feature 408 or a plurality of connection features, the rigid force transfer body 401 may be mounted to the housing e.g. axially constrained and/or rotationally locked.

Figure 28A:
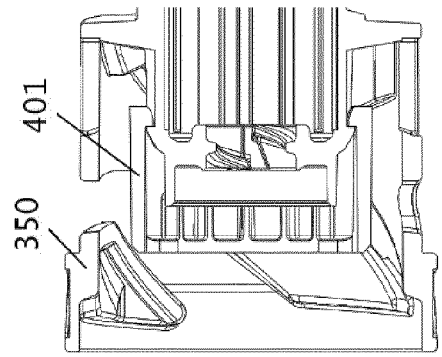
FIGS. 28A and 28B illustrate an assembling process, where a rigid force transfer body is assembled to a housing part or housing, where
Figure 28B:
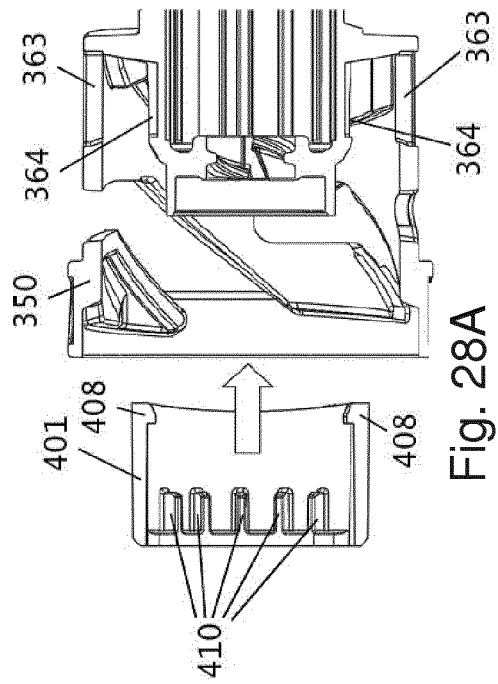
Figure 26:
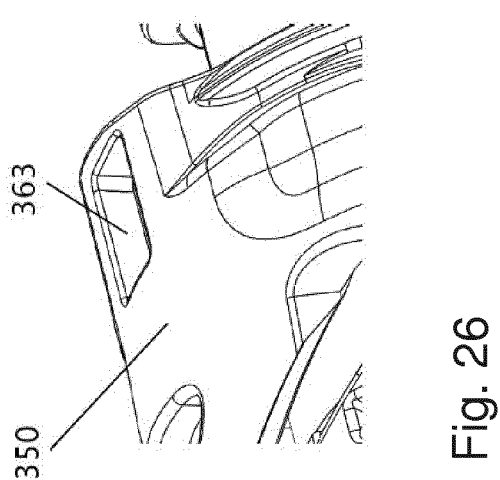
FIG. 26 illustrates a perspective view of a housing part or housing of the device.
Figure 27:
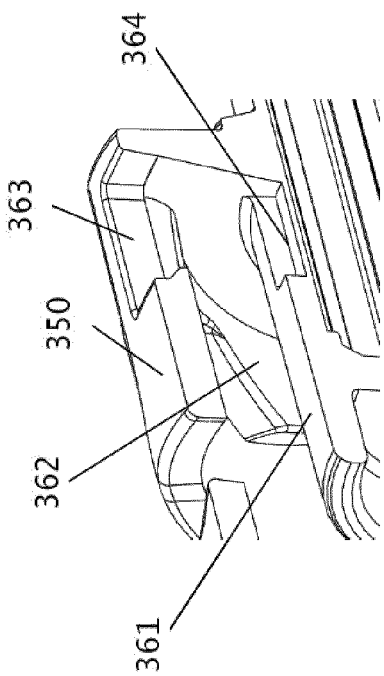
FIG. 27 illustrates a sectional view of the housing or housing part.
Figure 31:
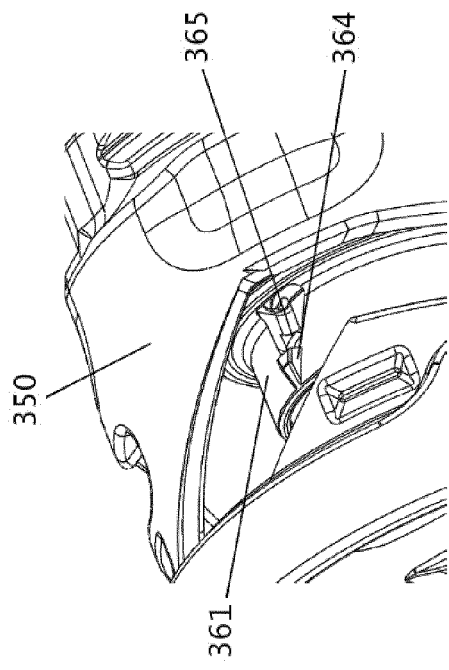
FIGS. 31 and 32 show different perspective views of the housing part of FIG. 29.
Figure 32:
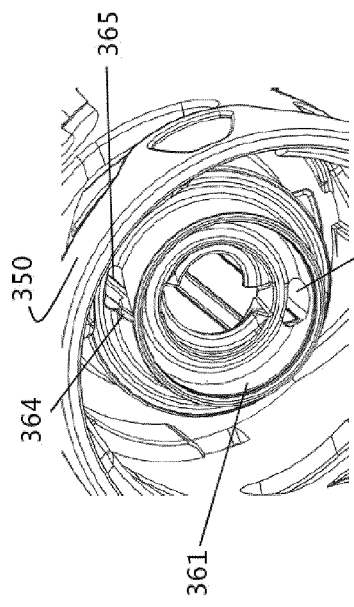
Figure 29:
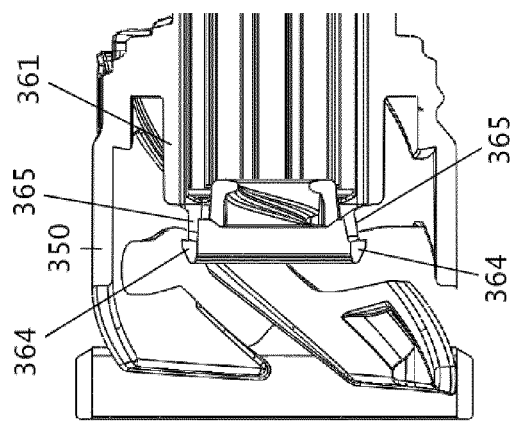
FIG. 29 shows a schematic sectional view through an embodiment of a housing part.
Figure 30:
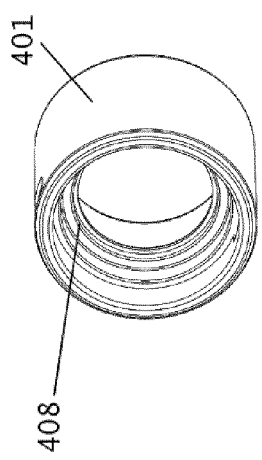
FIG. 30 shows a perspective view of an embodiment of the rigid force transfer body.

FIG. 26 shows the housing part 350 where FIG. 27 shows a sectional view through the housing part 350 of FIG. 26. with the piston rod guide section 361 and the hollow 362. As is apparent, the housing part 350 has an opening 363 which extends radially from an outer surface of the housing part towards the interior, e.g. into the hollow 362. The opening 363 may interact with connection or guide features 415 of one or both resilient members 402 and 403. For example, these guide features 415 may be arranged or retained in the opening to axially and/or rotationally constrain the respective resilient member to the housing. As is also apparent from FIG. 27, the housing part 350 is provided with a connection feature 364 or a plurality of connection features 364. The arrangement of the connection features 364 preferably matches the one of the connection features 408 of the force transfer body. In an exemplary embodiment depicted in FIG. 27, the respective connection feature 364 may be a groove. A proximally directed surface which delimits the groove distally may form a distal stop for movement of the force transfer body 401 relative to the housing part 350. As a plurality of separate connection features 364 is provided which are separate from each other, a rotational alignment of the force transfer body 401 relative to the housing part 350 has to be performed such that the angular position of the connection features 408 and 364 match before the force transfer body and the housing part are assembled utilizing relative axial movement. This is depicted in FIG. 28A which shows a situation right before the force transfer body 401 is assembled to the housing part 350 where the arrow denotes the axial movement. FIG. 28B shows the body 401 in a state where it has been assembled. Further components, e.g. the resilient member(s), are not shown for illustration purposes. During the assembling, the connection feature 408 may flex radially outwardly, which is permitted and, once the connection feature 364 has been reached, flex again radially inwardly such that a distally facing surface of the connection feature 408 can abut a proximally facing surface of the housing part 350 which delimits the groove as connection feature 364 distally. Snap features or clip features for the connection between the body 401 and the housing part 350 can be integrated into the body by way of injection molding, preferably by low-cost injection molding such as open-shot injection molding without the use of sophisticated molds, e.g. molds involving shutters or sliders which increase the costs of the molds significantly.

The connection feature 364 may overlap axially and/or azimuthally or angularly with the opening 363. The connection feature 364 may be radially offset with respect to the opening 363. Due to this overlap, a connection feature 364 can be formed by means of a slide of an injection mold used for the housing part 350. As the housing part is sophisticatedly designed anyway and the tooling involves considerable cost already, an additional slide is not so significant cost-wise. The connection features could also be configured in a different way. Such a modification of the embodiment discussed previously is discussed below in conjunction with FIGS. 29 through 33B.

As the force transfer body is, in this embodiment arranged distally relative to all resilient members of the bias system, these members are invisible for the user and/or cannot be tampered with when the cartridge has been removed.

Figure 33A:
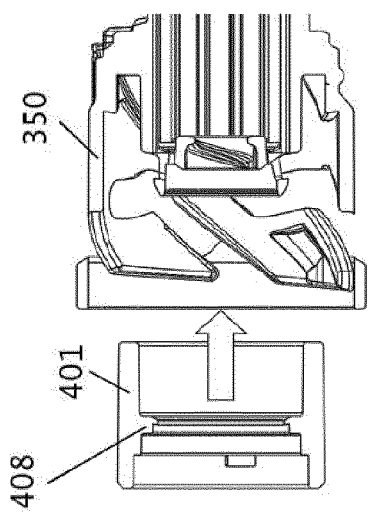
FIG. 33A illustrates the force transfer body before it is mounted to the housing part and FIG. 33B illustrates the situation after the body has been mounted.
Figure 33B:
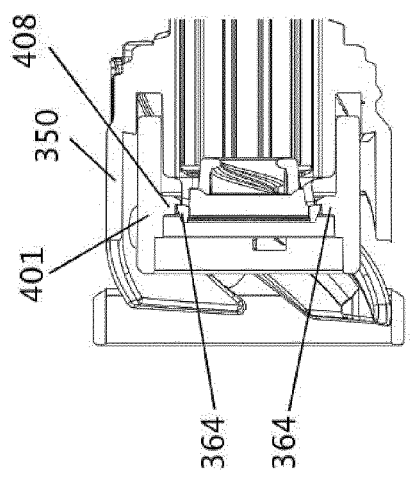

The rigid force transfer body can also be connected differently to the housing. One option is illustrated in conjunction with FIGS. 29 through 33B, where only the differences over the previous embodiment are discussed. Here, the connection features 364 on the housing part 350 are formed by one or more snap features and not by grooves. A proximal surface of the respective connection feature 364 delimits an opening 365 which protrudes radially through an outer wall of the piston rod guide section 361 in the distal direction. Connection features 364 of this kind can be formed by upstands on a core pin of the molding tool used for defining the interior of the piston rod guide section 361. The upstands may radially protrude from the core pin. The force transfer body 401, in this case, has a circumferentially extending flange as connection feature 408. Thus, when assembling the body 401 to the housing part 350, proper rotational alignment of the body 401 an the housing part is irrelevant as compared to the previously described embodiment. Clearly, a distally facing surface of the connection feature 408 is arranged to abut a proximally facing surface of the (respective) connection feature 364 after the assembly has been completed as shown in FIG. 33B. The flexibility required for the attachment may be provided at least partly by the reduced axial thickness of the snap nose of the connection feature 408 which may flex axially during the assembling process. The required force may be exerted via an oblique proximally facing surface of the connection feature 408, which contacts the housing part during the assembling process. Two springs or resilient members can be arranged at the proximal side of the rigid force transfer body or only one spring or resilient member can be used. Generally, features disclosed in conjunction with different embodiments may be combined with one another or substituted with each other as the case may be.

Figure 34:
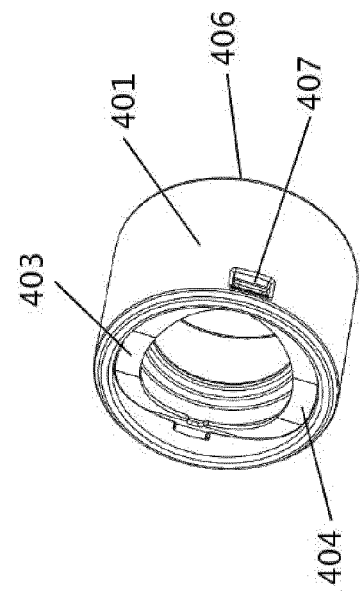
FIG. 34 shows a perspective view of a force transfer body to which one resilient member is assembled.
Figure 35:
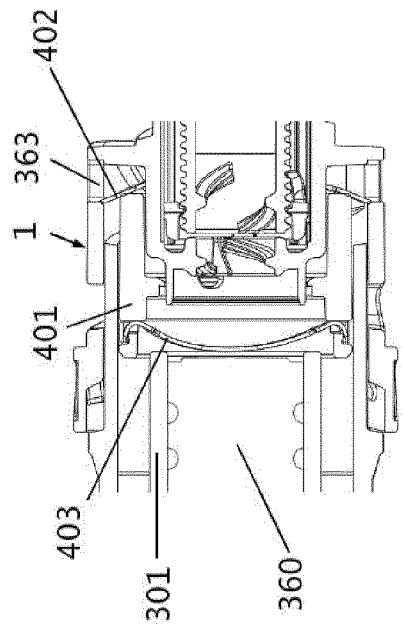
FIG. 35 shows a schematic sectional view of a section or region of an embodiment of a drug delivery device.

Another embodiment of a cartridge bias system is illustrated in FIGS. 34 and 35. In the following, only the differences with respect to the previously disclosed embodiments are discussed. FIG. 34 shows a perspective view of the force transfer body 401. FIG. 35 shows a sectional view through a drug delivery device 1 which corresponds largely to the one discussed in conjunction with FIG. 22. As is apparent from FIG. 34, the cartridge bias system comprises a sub-assembly which comprises or consists of the force transfer body 401 and a spring member as second resilient member 403 which assembled to the body. The diameter of the resilient member 403 may be adjusted to the diameter of the cartridge such that the spring may abut the cartridge at the proximal side as depicted in FIG. 35. The distal load transfer surface 407 of the force transfer body may, in this case, be formed by the distal surface of a mounting feature by which the resilient member 403 is mounted to the force transfer body 401. Thus, a spring member, e.g. a spring washer, can be used to bias the cartridge distally. The resilient member 403 may be clipped into the fore transfer body such that the resilient member 403 may be located in an interior of the force transfer body. Thus, the cartridge contact area 404 may be formed by a distal surface of the resilient member 403 as depicted. The remaining functionality may be as disclosed previously in conjunction with the other embodiments.

Locating one of the resilient members on the distal end or distal side of the force transfer body means that the axial travel required for the force transfer body will be reduced. The force transfer body must only travel far enough to create the deformation required for one of the resilient members rather than the sum of the axial deformations required for both resilient members as is the case if both members were arranged on the proximal side as in the FIG. 22 embodiment. This may provide advantages in the design of the connection of the force transfer body to the housing part 350.

Alternatively, as will be discussed in conjunction with the following embodiment, the force transfer body may be integrated into a single unitary body structure together with one resilient member. This embodiment is discussed below in conjunction with FIGS. 36A through 37, where again only differences over the previous embodiments are addressed. Here a unitary body structure 411, e.g. of plastic, incorporates the rigid force transfer body 401 and also the resilient member 403. The resilient member 403 is arranged at the distal end of the rigid force transfer body 401. Thus, the distal load transfer surface 407 may be formed by the transition region of the body structure 411 between the resilient member 403 and the body 401. The diameter of the resilient member 403 may correspond to the diameter of the cartridge body at the proximal end. The inner diameter of the force transfer body 401 may be greater than the outer diameter of the second resilient member 403. The resilient member may be connected to the force transfer body but have an interspace with respect to the force transfer body to provide resiliency. The resilient member 403 may be formed ring-like with two different web-like connections 412 to the force transfer body 401. At the distal side of the resilient member 403 one or more rigid cartridge contact features 413 may be provided. They may protrude axially from the ring structure of the resilient member 403 and, when the cartridge holder 302 is connected to the housing part 350 abut the proximal end or rim of the cartridge 301.

Figure 37:
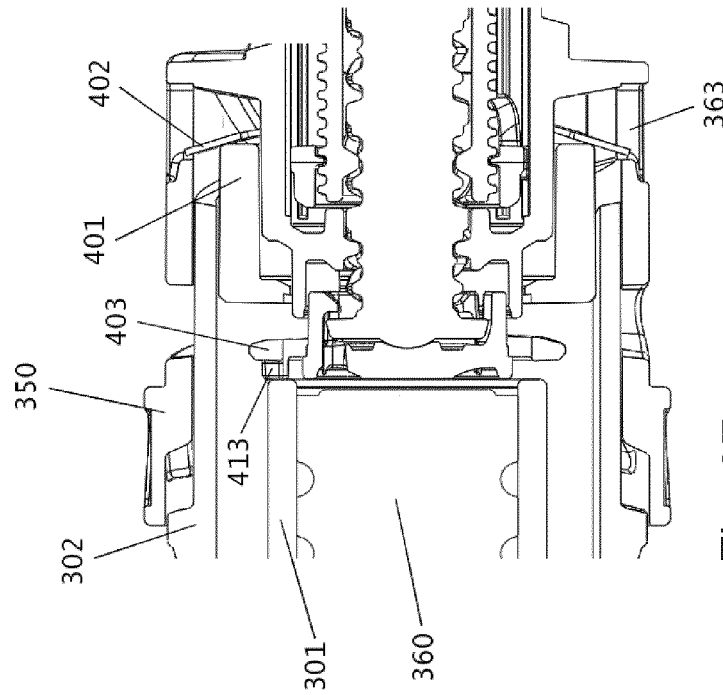
FIG. 37 shows a schematic sectional view through an embodiment of a drug delivery device.
Figure 36A:
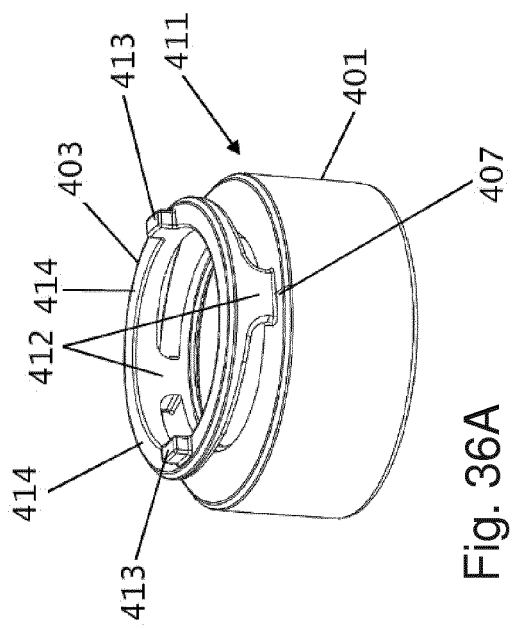
FIGS. 36A and 36B show a body structure on the basis of a perspective view, in a deformed state in FIG. 36B and an undeformed state in FIG. 36A.
Figure 36B:
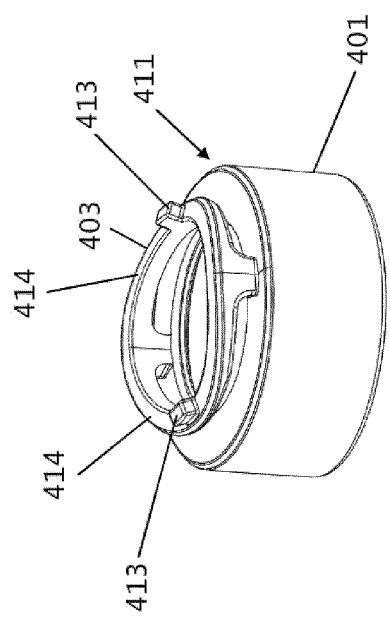

As depicted in FIG. 37, the resilient member 402, e.g. a metal spring member such as a washer is present as discussed previously. The integration of one of the resilient members into a body structure together with the rigid force transfer body reduces the number of components required and may also simplify the assembly process for assembling the cartridge bias system. In the angular region(s) between the connections 412 one or more flexible regions 414, e.g. arc-like regions, of the resilient member 403 may be formed. The flexible regions may be also designated as flexible arms 414. FIG. 36A shows the flexible arms 414 in a non-flexed state and FIG. 36B shows them in a flexed state, where, for example the proximally facing surface of the flexible arms may contact a distal surface of the force transfer body. When the cartridge holder has been connected to the housing the flexible arms may have been deformed as depicted in FIG. 36B as may have the resilient member 402.

As already discussed above, although it is desirable to reuse as many components or parts as possible, some components of a drug delivery device may need to be adjusted to take account of the change in cartridge dimension or filling level, drug, drug concentration, and/or drug formulation. The parts which are customized for the modified device are expediently non-interchangeable parts. That is to say, these part cannot be used in both devices, the original device and the modified device. The remaining parts which do not require modification may be interchangeable parts.

For example, as discussed above, the rigid force transfer body may not be an interchangeable member of the drug delivery devices. Rather, this body takes account for the reduced cartridge dimensions in one of the devices. To take account of different drugs concentrations and/or of different cartridge volumes, the mechanical advantage which is provided by the device may need to be adjusted. The mechanical advantage may be the ratio between the axial travel of the drive member 40, the number sleeve 61, the dial sleeve 62, and/or the button 70 during the delivery operation and the axial travel of the piston rod during the dose delivery operation. As stated above, the mechanical advantage in the device disclosed in conjunction with FIGS. 1 to 19 is 2:1. That is to say, the piston rod travels less during dose delivery than the drive member, dose indication member, and/or user interface member. This mechanical advantage is optimized for the larger volume cartridge which may contain 300 units of drug, for example. The components of the drug delivery device which may need adjustment, if the device is adjusted to cartridge of different dimensions and/or drugs, drug concentrations or drug formulations are: the inner body 20 or housing part 350, as this part may provide couplings to one or more members of the dose setting and drive mechanism such as piston rod (e.g. threaded coupling) and/or dose indication member (e.g. threaded coupling); the piston rod 30; as its axial displacement during delivery relative to the housing may define the quantity of liquid which is dispensed; the bung interface member or bearing 31, as the cartridges may have different inner diameters; the tracking member path, i.e. thread 44, which in the present embodiment is provided on the drive member 40, particularly on the distal part 41 thereof, but could be provided on another member as well, because the number of units in the modified device may be different; the dose nut or tracking member 50, as this member engages the tracking member path. Of these members, the bearing 31, the piston rod 30, the dose nut 50 and the distal part 41 of the drive member 40 belong to the dose setting and drive mechanism. The remaining parts of the dose setting and drive mechanism depicted in FIGS. 1 through 19 which move during the setting and/or dose delivery may be reused advantageously for the modified drug delivery device. Clearly, the interchangeable parts of the dose setting and drive mechanism exceed the non-interchangeable ones considerably. Also the housing 10 may be an interchangeable part as may be all parts of the device which are not expressly described as being modified.

Below, the adjustment to the respective parts are discussed in more detail with references to figures.

FIG. 38A shows a detailed representation of the piston rod 30 of FIG. 3 and FIG. 38B shows a modified piston rod 30. FIG. 38C shows an enlarged region of the piston rod of FIG. 38B. As can be seen in FIG. 38A, the threads 33 and 32 are oppositely handed and/or helical threads. The threads 33 and 32 may be intertwined or overlap axially. That is to say, they may cross one another. As explained above, one of these threads, i.e. thread 32, engages the inner body 20 or housing part 350 and thus governs the distal displacement of the piston rod during dose delivery when the piston rod rotates relative to the housing and the other thread, i.e. thread 32, is engaged with the drive member 40, in particular the distal part 41 thereof. The threads 32 and 33 in FIG. 38A have the same pitches and/or the same leads.

In order to adjust the mechanical advantage, the threads 32 and 33 may be tuned, e.g. with respect to the relation of the pitches and/or lead with respect to one another. Specifically, the threads 32 and 33 in FIG. 38B have different pitches and/or leads, where the lead and/or pitch of thread 32 is less than the one of thread 33. The ratio between the leads and/or pitches of these threads may be indicative for or determine the mechanical advantage. The thread 32 has the same or at least a very similar lead and/or pitch as the thread 21 on the inner body 20 or housing part, which governs the axial displacement of the dose indication member or number sleeve during dose setting and dose delivery. As can be seen in FIG. 38B, the modified piston rod 30 may have a greater axial extension than the non-modified one. This takes account of the potentially reduced axial displacement of the piston rod when the last maximum settable dose (e.g. 80U) is dispensed. The threads 32 and 33 in FIG. 38B still are oppositely handed.

The overall piston rod travel to fully dispense a full cartridge is similar between the modified and non-modified devices as is the axial dial out distance when the maximum settable dose, e.g. an 80U dose, is dialed or set. Hence the point at which the bearing end of the piston rod and distal end of drive sleeve or drive member are furthest apart (that defines the minimum length of the piston rod) is when the last maximum settable dose has been dialed but not dispensed. This distance is greater for the modified and consequently longer piston rod because its axial displacement for the last maximum settable dose is less.

For purposes of using molding to produce the piston rod with oppositely handed threads 32 and 33, it is advantageous that the two threads along their extension always cross on crossing points which are arranged on one straight line, e.g. a split line of the molding tool. This line is indicated by reference 37 in FIG. 38C. Therefore, it is advantageous that the mechanical advantage which is governed by the ratio of the leads or pitches of the oppositely handed threads to be an integer ratio, such as, 3:1, for example. Particularly, the mechanical advantage in the modified device will be greater than 2:1.

An inner diameter of the 3.0 mL or larger volume cartridge may be 9.6 mm, the one of the 1.5 mL or smaller volume cartridge may be 6.85 mm. As already discussed above, the smaller volume cartridge may contain 450 units of drug, e.g. insulin, whereas the larger volume cartridge may contain 300 units of drug, e.g. insulin. In order to deliver one unit from the lower volume cartridge, the piston rod 30 needs to travel 0.0904 mm per unit (IU). For the maximum settable dose, e.g. 80 unit, the displacement may be 7.232 mm. For a mechanical advantage of 3:1 this implies a pitch and/or lead for the threads 33 (coupling between drive member and piston rod) and 21 (coupling between number sleeve 61 and housing), which may have equal pitches and/or lead in the device shown in FIGS. 1 through 19, of 6.512 mm. In the 300 IU device, the lead may be 6.632 mm.

The ratio of the smaller cartridge cross-sectional area to the one of the larger cartridge is $0.509=(9.6/6.85)^2$ which is derived from the inner diameters specified above. Accordingly, the smaller cartridge has slightly more than half of the cross-sectional area of the larger volume cartridge. As the drug in the lower volume cartridge is three times stronger per unit volume, the piston rod or bearing travel per unit which is required for the modified device as compared to the non-modified one is $0.333/0.509=0.654$, which is slightly less than $2/3$. Thus, if the threaded coupling of the display mechanism 60/number sleeve 61 to the housing/inner body should be maintained, the mechanical advantage would have to be changed from 2:1 to 3.06:1. This would avoid re-tooling or re-designing an additional part, e.g. number sleeve 61. However, as explained above, integer ratios for the mechanical advantage are advantageous from the molding perspective. Moreover, it is envisaged to reuse as many components as possible.

Therefore, the number sleeve thread, i.e. thread 21 on inner body 2 and, of course, its counterpart on the number sleeve 61, may be maintained with respect to pitch and/or lead. The threads on the piston rod may be modified to provide the 3:1 mechanical advantage. As the thread 21 is not quite correct for the relevant mechanical advantage, a small gap will open up between the piston rod or bearing and the bung during setting of a dose. This gap is approximately 0.1 mm for 80 units (i.e. the maximum settable dose). Thus, when the dispensing operation is commenced, the proximal offset of the piston rod relative to the bung during dose setting will, due to the mechanical advantage, require about 0.3 mm of button travel during the dispensing operation to close the gap to the bung before drug is actually dispensed. The small travel will probably not be noticed by users because there is already a significantly greater, e.g. 1.6 mm, non-dispensing button 70 travel required to disengage the clutch for the dispensing of the dose. Thus, the additional travel of 0.3 mm will not be noticed by the user as he has to move the button 70 anyway significantly, before the liquid is ejected from the cartridge.

As explained above, the piston rod will slightly travel proximally during dose setting. The proximal movement will be discussed in more detail below. In particular, it is a result of the fact that the bore of the 1.5 mL cartridge (6.85 mm) is not exactly half the cross sectional area of the bore of the 3 mL cartridge (9.6 mm)—$6.85^2/9.6^2=0.509$ not 0.5. If it was exactly 50% or 0.5 then, as the drug in the 1.5 mL cartridge is 450IU (triple strength or concentration) the effective doses per unit travel of the piston rod in the 1.5 ml cartridge would be $3*0.5=1.5$, instead it is $3*0.509=1.527$. Because the travel of the piston rod is defined as $F/(G/F+1)$ per revolution of the drive member or drive sleeve (the drive sleeve rotates one turn per 24U dialed) where G is the pitch of the thread interface with the drive sleeve and F the one of the thread interface with the inner body, then $F/(G/F+1)$ for the modified (450IU, 1.5 mL cartridge) device has to be $1/1.527$ times $F/(G/F+1)$ for the non-modified (300IU, 3 mL cartridge) device. As both thread pitches are formed on the same part, i.e. the piston rod, then F/G has to be a fixed ratio of 1:1 in the case of the non-modified device (300IU, 3 mL) and 2:1 in the case of the modified device (450IU, 1.5 ml) otherwise the cross over points for the two thread forms would not follow an ordered pattern and the piston rod would be impossible to mold using an open and shut mold tool as has been discussed previously. Hence to achieve the 1/1.527 ratio the value of G has to be slightly different in both devices. This value of G in the non-modified (300IU, 3 mL) device is exactly matched to the number sleeve thread pitch so that when one dials out, the drive sleeve just winds up the thread form on the piston rod as it is clutched to and follows the helical path of the number sleeve. If we are not changing the number sleeve thread pitch in the modified (300IU, 1.5 mL) device then the pitch G will be slightly different resulting in the back winding (proximal movement) of the piston rod when a dose is dialed or set. In the non-modified device, there will not be proximal movement at all of the piston rod during dose setting or less movement than in the modified device when an equivalent dose set in both devices, the modified one and the non-modified one.

A distal movement of the piston rod when dialing should be avoided as this would dispense drug. Having a proximal movement of the piston rod or backing off the piston rod during dose setting may have some advantages as it pulls the piston rod and/or bearing away from the bung in the cartridge and reduces the risk of the device 'weeping', i.e. dispensing a small amount of drug from the cartridge unintentionally, at the needle or dispensing end as the user dials a dose. In a device where the number sleeve thread pitch is on bottom tolerance and the piston rod thread pitch(es) is(are) on top tolerance there is a risk of the 'weeping' at the needle when dialing. This may be negated or avoided by other means in (pen-type) devices (e.g. by backing off the number sleeve at the end of dose), but backing off the piston rod during dialing also helps to prevent the failure mode of 'weeping'. As already discussed, the only down side of the piston rod moving proximally during dose setting is that you get a little 'lost motion' or low dispense force when dispensing a large dose (equivalent to 0.3 mm button travel for the maximum settable dose of, e.g., 80U) where there is minimal dispense force until the piston rod has taken up the proximal travel generated during dialing and made contact with the bung again.

If the inner bore diameter of the cartridge or cartridge body 340 is reduced, the diameter of the bearing 31 may have to be reduced as well. Particularly, if the bearing of the original non-modified device is of a diameter which is greater than the inner diameter of the cartridge of the modified device, a modification may be required. The bearings of the two devices are shown in FIGS. 39A and 39B. FIG. 39A shows the bearing 31 of the device described above and FIG. 39B shows the bearing 31 of the device which has been modified to suit a cartridge of reduced inner diameter. As can be easily seen, the diameter of the bearing 31 in FIG. 39A is greater than the one of the bearing 31 in FIG. 39B. The bearing 31 in FIG. 39A may have a laterally outwardly flange-like portion 34 which extends circumferentially around the bearing 31.

As can be seen from FIG. 39B, such a portion may have a reduced radial width or not be present at all in the modified bearing. Both bearings comprise fixing features 35, e.g. snap features, which are configured to engage a fixing portion 36 (see FIGS. 38A and 38B) on the respective piston rod 30. The fixing features, for example three, may be uniformly disposed in the circumferential direction. For example the diameter of the bearing in FIG. 39A may be greater than 7 mm, e.g. 9.2 mm. The one in FIG. 39B may be less than 7 mm, e.g. 6.5 mm.

Figure 40A:
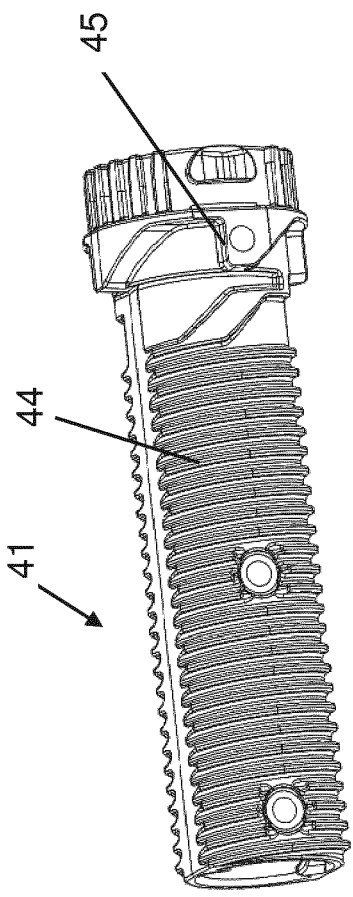
FIGS. 40A and 40B illustrate modifications to a drive member part.
Figure 40B:
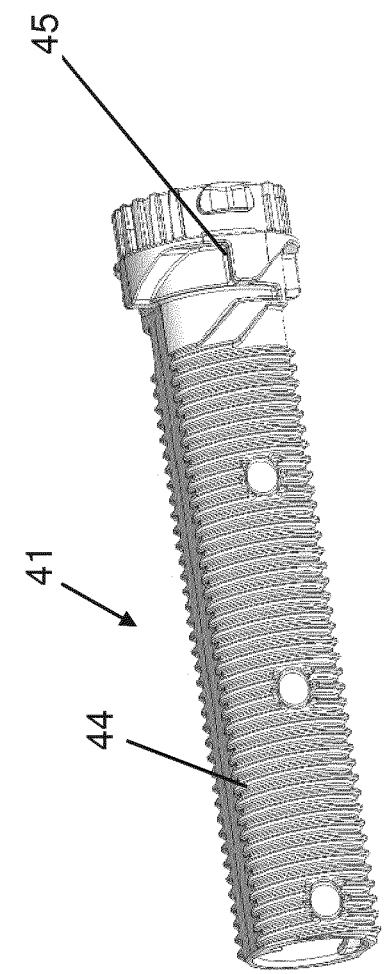

FIGS. 40A and 40B illustrate the changes in the drive member 40. Advantageously only the distal part 41 of the drive member 40 is modified. FIG. 40A shows the part 41 of FIG. 9 and FIG. 40B the modified one. The modified part is longer than the original one to provide room for a longer thread 44 to take account of the increase in units in the modified device from 300 to 450 IU. Also, the thread pitch or lead is smaller in the modified part, e.g. 1.170 mm, than in the non-modified one, e.g. 1.250 mm. The length of the part 41 may be increased easily without increasing the overall length of the modified device over the original device, as the cartridge length is smaller in the modified device. Moreover, the inner body or housing part may have to be modified anyway, such that there is room for the force transfer body 401 as explained previously, which may shift the point of threaded engagement between housing/inner body/housing part and piston rod distally in the modified device. Thus, the drive member 40 or the distal part 41 thereof which is arranged in the inner body or housing part 350 may be lengthened. The area of the stop face(s) 45 may be maintained in the modified part, such that the last dose dial stop torque should be largely unaffected by the modification.

Figure 12:
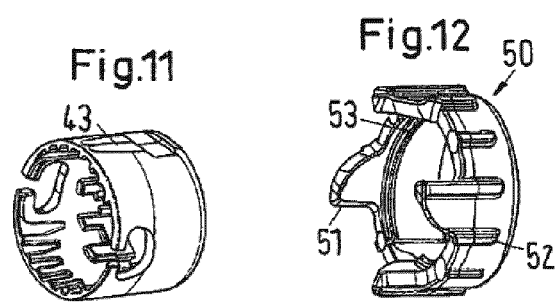
FIG. 12 shows the last dose nut of the drug delivery device of FIG. 1.
Figure 13:
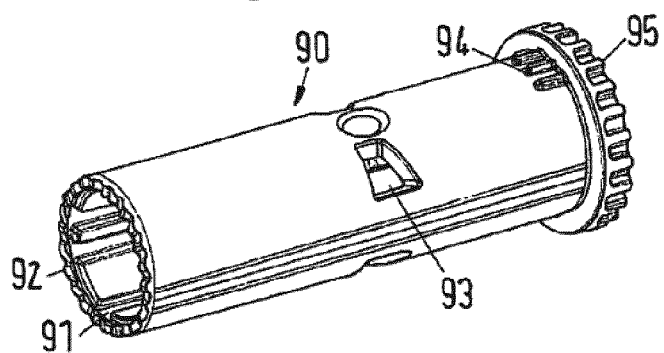
FIG. 13 shows a clutch component of the drug delivery device of FIG. 1.
Figure 14:
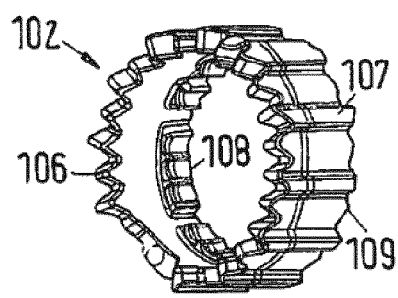
FIG. 14 shows a first clicker component of the drug delivery device of FIG. 1.
Figure 15:
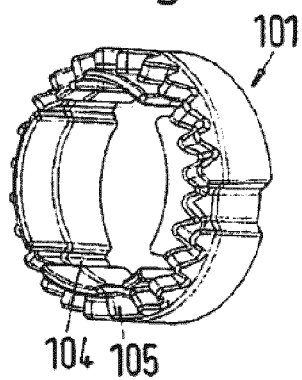
FIG. 15 shows a second clicker component of the drug delivery device of FIG. 1.
Figure 41B:
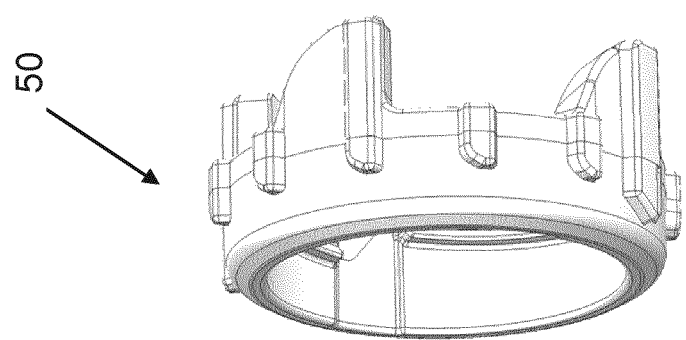
FIGS. 41A and 41B illustrate modifications to a tracking member.
Figure 41A:
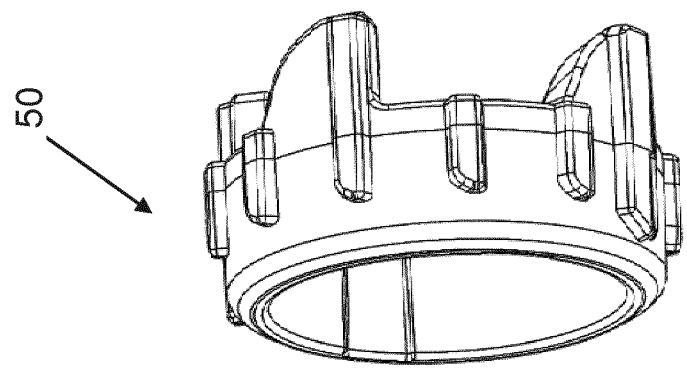

FIGS. 41A and 41B illustrate the modifications in nut 50, where FIG. 41A shows the nut 50 of FIG. 12 and FIG. 41B shows the modified nut 50. The modified nut 50 is shorter than the nut 50 in FIG. 41A, e.g. by more than 0.3 mm, e.g. about 0.5 mm. Of course the thread pitch or lead for the threaded engagement has been adjusted to the pitch or lead of the thread 44 of the modified drive sleeve part 41 which the modified nut 50 engages.

FIGS. 42A and 42B illustrate the modifications in the housing part 350 or inner body 20. FIG. 42B shows a section of the modified housing part or inner body. FIG. 42A illustrates the modifications which are made in a merged representation which shows features realized in both housing parts, the modified one and the non-modified one. As can be seen in FIG. 42B, the modified housing part 350 has the hollow 362 between the piston rod guide section 361 and an inner wall of the housing part 350. The piston rod guide section 361, e.g. the section where the thread 366 which engages thread 32 of the piston rod is arranged, may be arranged in the wider section of the inner body 20 or housing part 350. As is apparent from FIG. 42A, the thread 366 has been offset distally relative to the thread 366' in the non-modified housing part.

In the non-modified housing part, the piston rod guide section 361 within the wider section of the housing part 350 may not be present at all. As is apparent from comparing threads 366 and 366', the lead and/or pitch of the thread 366 has been adjusted to the one of the modified piston rod 30. That is to say, the thread 366 has a smaller pitch and/or lead than the thread 366'. Moreover, in the region of the hollow 362, the rigid force transfer body 401 of the cartridge bias system which has been discussed previously in connection with FIGS. 22 through 37 may be arranged. The wider section 367 of the housing part 350 may be arranged distally offset from a more narrow section 368 of the housing part 350. The wider section 367 of the housing part 350 may receive a part of the cartridge unit cartridge or holder when attaching the cartridge unit to the housing. In the modified device, as opposed to the non-modified one, the thread 366 is arranged in the wider section of the housing part.

Moreover, the housing part 350, preferably within the wider region 367, provides room for additional features, which may, for example, be provided in regions 369 on an inner wall of housing part 350, e.g. proximally offset from the thread 366. In regions 369 the (radial) material strength of the housing part 350 or inner body 20 may be varied, for example to provide protrusions or ramps for a coding system which prevents that cartridge assemblies or units which are intended to be used in the non-modified device can also be connected to the housing of the modified device and vice versa. If a non-matching cartridge unit is attempted to be assembled to a housing unit the attachment to the housing or housing part may be prevented by abutment of non-matching coding features. If the coding features match, however, the cartridge unit can be attached to the housing or housing part. The coding functionality is discussed in more detail further below.

Turning again to FIGS. 42A and 42B, it is apparent that features in the housing part 350 and/or the rigid force transfer body 401 of the cartridge bias system retained in the hollow 362 may be used to prevent attachment of a larger dimension cartridge, e.g. a cartridge having a greater inner/outer diameter, to the housing comprising the modified housing part shown in FIG. 42B. As the piston rod guide section 361 is arranged within a section of the housing part 350 which is empty in the non-modified device and/or is distally offset with respect to the corresponding section in the non-modified device, abutment with a non-matching cartridge, e.g. the bung or the proximal rim thereof, may prevent attachment of a cartridge unit to the housing or housing part 350. The same holds for the rigid force transfer body 402. Moreover, as the diameters of the bearings 31 in the modified device and in the non-modified device may be different, the greater diameter bearing will abut the proximal rim of the smaller diameter cartridge, if, for some reason, the smaller diameter cartridge could be connected to the wrong dose setting and drive mechanism.

Figure 43:
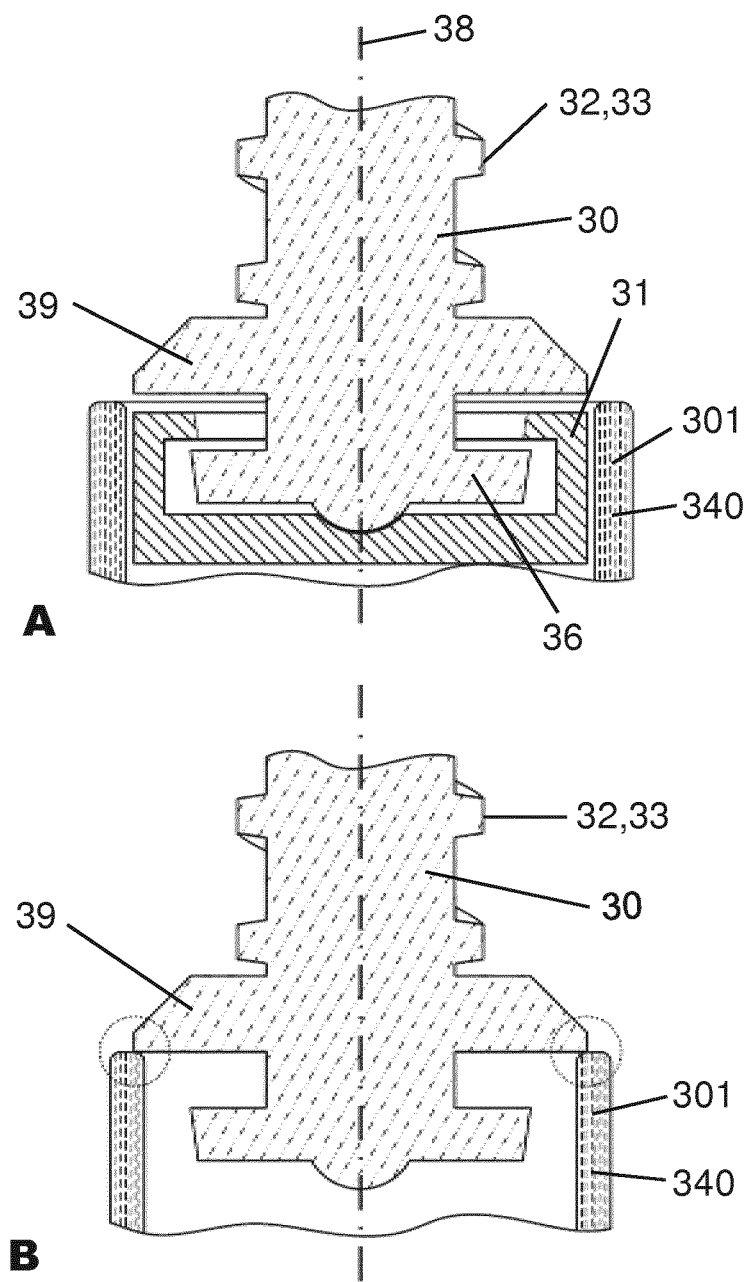
FIG. 43 illustrates an embodiment of a piston rod on the basis of different sectional representations.

During a cartridge replacement/resetting operation the bearing 31 may be accessible for the user. Thus, it could be disconnected from the piston rod 30. When disconnecting the bearing 31, the fixing portion 36 may be destroyed as well such that only a portion of the piston rod remains which has a small-diameter, e.g. potentially smaller than the inner diameter of the cartridge, e.g the smaller dimension cartridge and/or the larger dimension cartridge. Alternatively, the fixing portion 36 may have a smaller diameter on its own such as a spherical shape for a snap fit connection, for example (not shown). Therefore, after the bearing has been disconnected from the piston rod, the piston rod could be used potentially in conjunction with a cartridge the inner diameter of which is less than the outer diameter of the bearing which has been disconnected, as the remaining piston rod structure may have an outer diameter which is less than the one of the bearing. In order to prevent this potential misuse, the piston rod 30 may be provided with one or more blocking features 39. This is depicted, for example in FIG. 43 which shows a sectional schematic view of a piston rod 30 in two situations, A (in the upper region) and B (in the lower region). The piston rods 30 in both representations, A and B, are aligned along the axis indicated by line 38. In situation A, the bearing 31 is attached and the piston rod 30 can move distally with respect to the cartridge 301 which has a greater inner diameter than the cartridge 301 in situation B.

In situation B, the bearing, which has an outer diameter greater than the inner diameter of the cartridge in situation B, is detached and the piston rod could, theoretically, move distally relative to the cartridge with the smaller inner diameter. However, this movement is blocked by the blocking feature 39 which abuts the cartridge, in particular a proximal end face of the cartridge body 340. The radial dimension, e.g. the diameter of the piston rod defined by the blocking features 39, may be greater than the inner diameter and/or the outer diameter of the cartridge with the smaller inner diameter and/or less than or equal to the inner diameter of the cartridge with the larger inner diameter. Thus, the blocking feature may block distal movement of the piston rod of the wrong dose setting and drive mechanism relative to the smaller dimension cartridge, even if the bearing has been disconnected. The diameter of the piston rod in the region of the blocking feature 39 may be less than or equal to the diameter of the bearing 31 which is connected to the piston rod 30 in the region of the fixing portion 36. The blocking feature 39 may be distally offset from the threaded portion of the piston rod 30, e.g. where threads 32 and 33 are provided. The blocking feature 39 is expediently proximally offset from the fixing portion 36.

In the following, some concepts relating to mechanical coding between cartridge units and housings are described, which could be employed in the present disclosure for preventing that cartridge units which are designed for one dose setting and drive mechanism are operatively connected to the wrong dose setting and drive mechanism, where the mechanisms may be based on the same device architectures with interchangeable parts and non-interchangeable parts and/or may be designed or adjusted for cartridges having different dimensions, drug or drug formulations as discussed further above.

In reusable drug delivery devices, where the same dose setting and drive mechanism can be used in conjunction with several cartridges, it is extremely advantageous to ensure that only cartridges with a specific drug or drug formulation can be operatively connected to the drive mechanism, e.g. connected to a housing within which the drive mechanism or elements thereof are retained. This is, sometimes, achieved by so-called coding or dedication systems or mechanisms. These systems or mechanisms may comprise features which are adjusted such that in a set of two drug delivery devices, each comprising a housing with a dose setting and/or drive mechanism and a cartridge unit releasably connected to the housing, where the two cartridge units have different drugs, drug formulations and/or dimensions, the respective cartridge unit can only be connected to the housing of one device and not to the housing of the other device.

In the following text, embodiments of systems are described, which are suitable for uniquely coding cartridge units or assemblies with specific drugs, drug formulations and/or cartridge dimensions or volumes to housings or the dose setting and/or drive mechanisms retained therein. This avoids that the wrong mechanism can be used in conjunction with a particular cartridge unit, e.g. one of the assemblies discussed further above. The disclosed embodiments are particularly suitable for being used for drug delivery devices which employ a bayonet or bayonet-type connection between the cartridge unit and the housing, which involves an initial at least axial movement (first stage) and a subsequent at least angular or rotational movement (second stage) when attaching the cartridge unit to the housing. Additionally the disclosed concepts may but need not be designed to achieve an axial movement of the cartridge unit away from the housing after the first stage and before the end position of the cartridge unit with respect to the housing has been reached.

Figure 44:
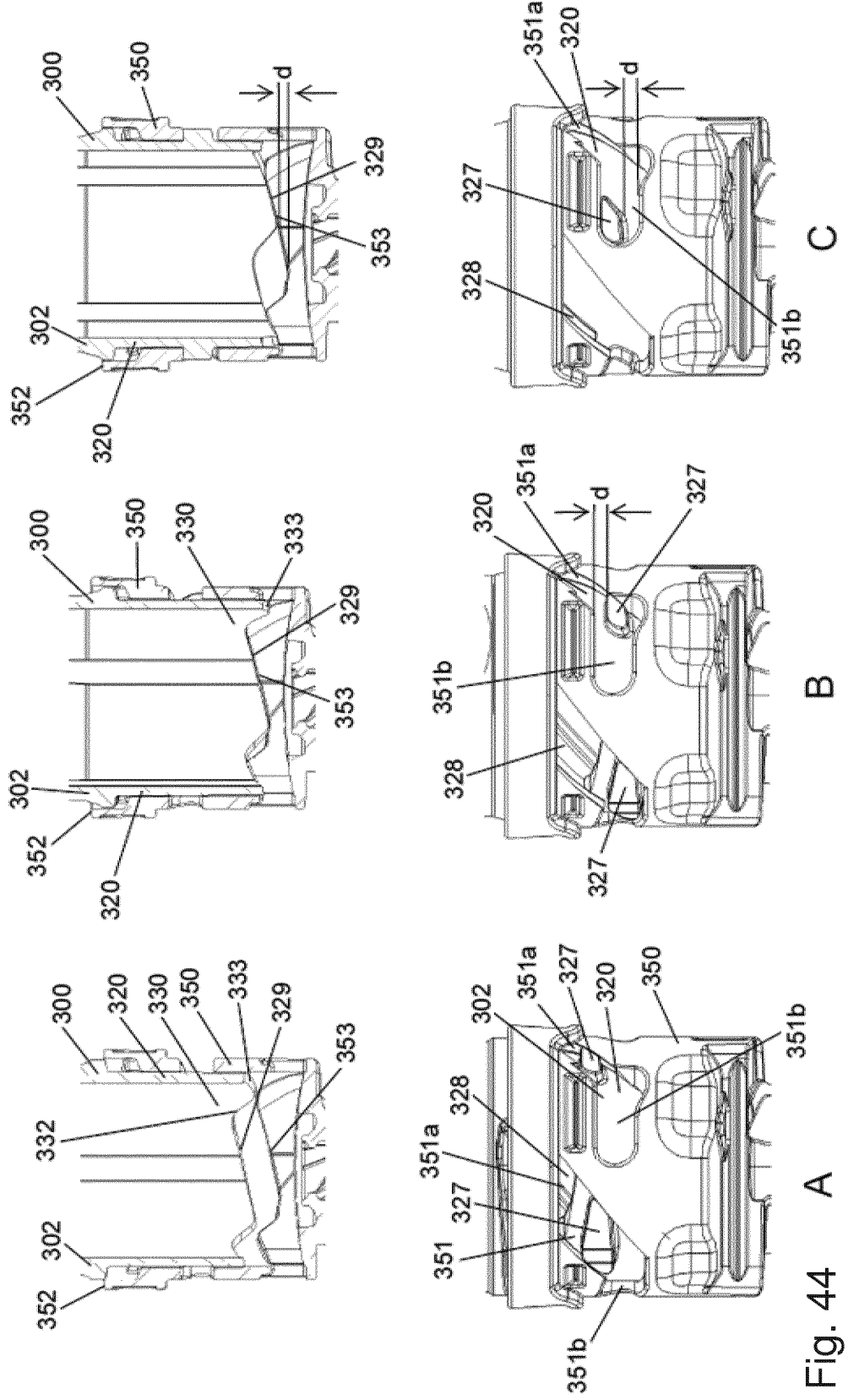
FIGS. 44 through 50 illustrate embodiments of coding systems or structures.

One embodiment is discussed below in conjunction with FIG. 44. FIG. 44 schematically illustrates different situations (A through C) during the connection of a cartridge unit 300 to a housing or housing part 350 for a drug delivery device. Situation A is shortly after the connection or attachment has begun, i.e. during the first stage of movement, situation B is after the first stage of movement has been completed and before the second stage of movement begins, and situation C is when the end position of the cartridge unit 300 relative to the housing has been reached after the second stage of movement has been completed. The lower portion of the figure shows side views in the situations A through C and the upper portion shows sectional views in the associated situation.

The cartridge unit 300 is represented by a cartridge holder 302, e.g. one of the holders described previously. Of course, although not depicted, the cartridge may be present in the cartridge holder. In FIG. 44, the connection region or interface region 320 of the cartridge holder is shown. In this region, one or more features are arranged which are adjusted to interact with features in a housing when connecting the cartridge holder 302 or the cartridge unit or assembly 300 to the housing to form a drug delivery device. In particular, in the connection or interface region 320, one guide feature 327 or a plurality of guide features 327 is arranged. Different guide features 327 may be axially aligned and angularly separated from one another. The guide features may have different angular or azimuthal widths as depicted or the same angular or azimuthal widths. The guide features 327 are provided to guide movement of the cartridge holder 302 relative to the housing during assembling or attaching of the cartridge holder 302 to the housing. The cartridge holder 302 may, in particular in the connection or interface region 320, comprise a securing or detent feature 328. A plurality of securing features 328, where only one of them is shown, may be provided which are preferably uniformly disposed in the angular direction, e.g. diametrically opposite with respect to one another. The respective guide feature 327 may be realized as a lug protruding from the cartridge holder 302. The securing feature 328 may have a helical shape or extension. The securing feature 328 may be designed to releasably secure the cartridge holder in the end position against rotation relative to the housing in the direction required for detaching the cartridge holder 302 from the housing. This avoids accidental disconnection of the cartridge holder from the housing.

The housing part 350 may be integrally formed with an (outer) housing 10 of a drug delivery device as explained later on or as an additional component mounted in or at the housing. The housing part 350 comprises at least one, preferably a plurality of housing guide features 351. The housing guide feature 351 may be a track or channel. The housing guide feature 351 comprises two different sections, a first section 351a and a second section 351b. The first section 351a extends at least predominantly axially, such as only axially or helically. In the depicted embodiment it extends helically. The helix angle of the helix along which the first section 351a extends may be the same as the one defined by the helical extension of the securing feature 328. The axial distance between two opposite ends of the section 351a may be greater than the angular extension of the first section. For example the midpoints of the respective end can be taken as reference points for measuring the distances separating the ends.

The housing part 350 has a distal end 352. Before the cartridge holder 302 is assembled to the housing part 350, the distal end 352 may face the cartridge unit 300. The housing part 350 may be hollow, e.g. formed sleeve-like, in order to enable components of the drive mechanism and/or of the cartridge assembly to be received within an opening of the sleeve member or to travel through the opening. The section 351a is expediently arranged closer to the distal end of the device or the housing than the second section 351b of the housing guide feature 351. The second section 351b of the guide feature 351 may extend at least predominantly angularly, such as only angularly or helically. Particularly, the axial distance between opposite ends of the second section may be less than the angular extension of the second section. The axial distance the cartridge holder is moved in the first section may be greater than the axial distance it is moved in the second section. Alternatively or additionally, the angular distance the cartridge holder is moved in the first section may be less than the angular distance it is moved in the second section. The axial distance the cartridge holder is moved in the second section or during the second stage may be less than or equal to 1 mm, e.g. less than or equal to 0.5 mm. The guiding interface may be a bayonet-type interface. The rotational directions in the first stage and in the second stage may be equal.

In the depicted embodiment, the first section 351a extends helically or is configured to define a helical interface. The second section 351b may extend only angularly or helically and/or be configured to allow a, preferably limited, axial movement. Thus, there may be some axial play in the second section. This preferably holds, if the second section extends only angularly (see section 351b in FIG. 44C). The play may allow a movement of the cartridge holder 302 away from the housing 350 during the second stage as will be explained below. If the second section extends helically (see the leftmost section labelled with 351b in FIG. 44A) an axial play may not be present. Particularly, as is shown in the figures, different housing guide features 351 may have differently configured second sections 351b, e.g. the second section of one housing guide feature may extend helically and the second section of another one may extend only angularly. The first sections of different housing guide features may be formed alike. The first section 351a of the housing guide feature 351 may guide the movement during the first stage, e.g. axially and/or angularly, whereas the second section 351b of the guide feature may guide, preferably only, angular or rotational movement of the cartridge holder relative to the housing. Nevertheless, during the second stage of movement, there may still be an axial component of the movement of the cartridge unit away from the housing. For this purpose, a further interface is established which will be explained in more detail below. Thus, as axial and angular or rotational movements are involved when the cartridge unit guide feature 327 interacts with the second section 351b of the housing guide feature 351, the movement may still be helical in this section. The helix angle of the helix associated with the movement during the second stage or the second section may be less than the one associated with the first section or the first stage. Alternatively or additionally the helixes which define the helical extension of the respective sections 351a and 351b or the helical movement during the two stages may be oriented in opposite directions, e.g. they may be oppositely handed. In this way, while the guide feature 327 is in the second section, the cartridge holder may travel in the distal direction relative to the housing, i.e. opposite to the axial direction it travels in when the movement is guided in the first section. Thus, when the guide feature 327 interacts with or travels in the first and second sections of the guide feature 351 different stages of movement occur. A mechanism which has an initial proximal movement of the cartridge holder towards the housing which is followed by a distal movement away from the housing is disclosed in WO 2012/130704 A1, the entire disclosure content of which is herewith incorporated by reference into the present application. However, the proposed concepts are applicable to other, preferably reusable, drug delivery devices as well, e.g. to injection devices such as pen-type injectors.

As mentioned above already, the axial movement away from the housing during the second stage of movement may be generated by a further interface, i.e. by an interface different from the guiding interface established by the cooperating guide features 327 and 351. This interface may be a ramp interface. For this purpose, the cartridge holder, e.g. at its proximal end, comprises at least one ramp surface 329 or a plurality of ramp surfaces. The housing comprises at least one corresponding ramp surface 353 or a plurality thereof. The ramp surfaces 353 and 329 do not interact during the first stage of movement (situation A), are brought into cooperation with one another at the end of the first stage (situation B), i.e. after the cartridge holder has been moved by a first stage axial distance towards the housing, and interact with one another during the second stage (situation C). The slope of the ramp surfaces 353 and 329 may be equal.

However, it should be readily appreciated that one ramp surface is sufficient and the feature sliding along the ramp surface may have a different, i.e. not necessarily ramp-like, geometry. The slope of the ramp surface is preferably constant. The slope of the ramp surface may be chosen such that during the rotational movement during the second stage the ramp surface causes the axial movement by the distance d away from the housing (which takes place from situation B to situation C). As can be seen, in situation B, the axial clearance between the guide feature 327 and the wall delimiting the guide feature section 351b distally may be equal to the distance d. At the end of the attachment process in situation C a distally facing surface of the guide feature 327 and a proximally facing surface of the housing may abut. In situation C, the distance between a proximally facing surface of the guide feature 327 and of a distally facing surface of the housing may be greater than or equal to d. In situation C, when the cartridge holder has been attached to the housing, the securing feature 328 has engaged a complementary securing feature in the housing (not illustrated). The rotation angle during the second stage may be greater than 10° and/or less than 90°, such as less than 45°, e.g. about 20°.

The angular extension of the ramp surface 253 and/or 329 may be greater than the rotation angle during the second stage. This enables that a section of the ramp surface, e.g. of the ramp surface 253, can be used to abut a coding feature, e.g. of the cartridge holder, if a cartridge holder with a non-matching coding structure is attempted to be attached to the housing. This will be explained later below.

The cartridge holder 302 comprises one or a plurality of coding features 330. The coding feature may be oriented axially. The coding feature may be integrated with the ramp surface in a common ramp structure. The coding feature comprises a surface 332 which delimits the coding feature in the angular direction, e.g. that angular direction opposite to the direction of rotation during the first stage and/or during the second stage. Rotation of the cartridge holder 302 relative to the housing part 350 during the first stage and the second stage is clockwise as seen from the distal end towards the proximal end in FIG. 44. The surface 332 may extend axially and/or, as seen in the axial direction, overlap with the ramp surface 329. The surface 332 may have an axial extension, which is greater than d, greater than the axial distance during the first stage and/or during the second stage and/or greater than the axial extension of the ramp surface 329 and/or 353. The angular extension of the surface 332, if any, is expediently less than the one of the ramp surface 329 or 353. By choosing the axial extension greater than the axial distance covered during the first stage and/or during the second stage, a proximally facing surface 333 of the coding feature 330, which adjoins the surface 332 angularly, e.g. in the rotational direction during the first stage and/or the second stage, may be used to abut the ramp surface 353 or another distally facing surface in the housing, which is provided by a housing coding feature, in case the cartridge holder is attempted to be attached to a non-matching housing. This abutment prevents further axial movement of the cartridge holder towards the housing and, accordingly, the second stage cannot be performed and the cartridge holder cannot be attached to the housing. The coding therefore acts during the first stage of movement, i.e. as early as possible, to alert a user if he or she attempts to attach an incorrect cartridge unit to the housing. When the length of the surface 332 is significantly greater than the axial distance during the second stage or dimension 'd', e.g. at least twice the axial distance, it can be ensured that the coding feature 330 can block the attachment of the cartridge holder early during the first stage, if the cartridge holder and the housing do not match. Alternatively or additionally, it may be beneficial, if the length of the surface 332 is greater than the axial distance during the first stage.

Using ramp structures in the housing or on the cartridge holder enables a robust and easy to implement coding structure with a variety of differently formed and/or arranged coding features, which form unique coding structures together with ramp surfaces or ramp features into a common ramp structure. In other words, the coding features and the ramp surfaces may be axially aligned and angularly separated. Such structures can be easily incorporated in existing holders without extensive changes to the expensive molding tools.

The ramp structures used in the present disclosure may be formed rotationally symmetrical with respect to a rotation by 180°. In this way, the cartridge holder may be connected to the housing in two different rotational orientations. Likewise, the guide features may be arranged rotationally symmetrical, particularly with respect to a rotation by 180°.

The ramp surfaces of the ramp structures used in the present disclosure may be separated by coding features arranged between them. The transition between the coding feature and the subsequent ramp surface may be formed by a steep axially oriented surface or by a sloped surface. The (angular) slope in the transition region between two ramp surfaces may be greater than the slope of the ramp surface.

Figure 45:
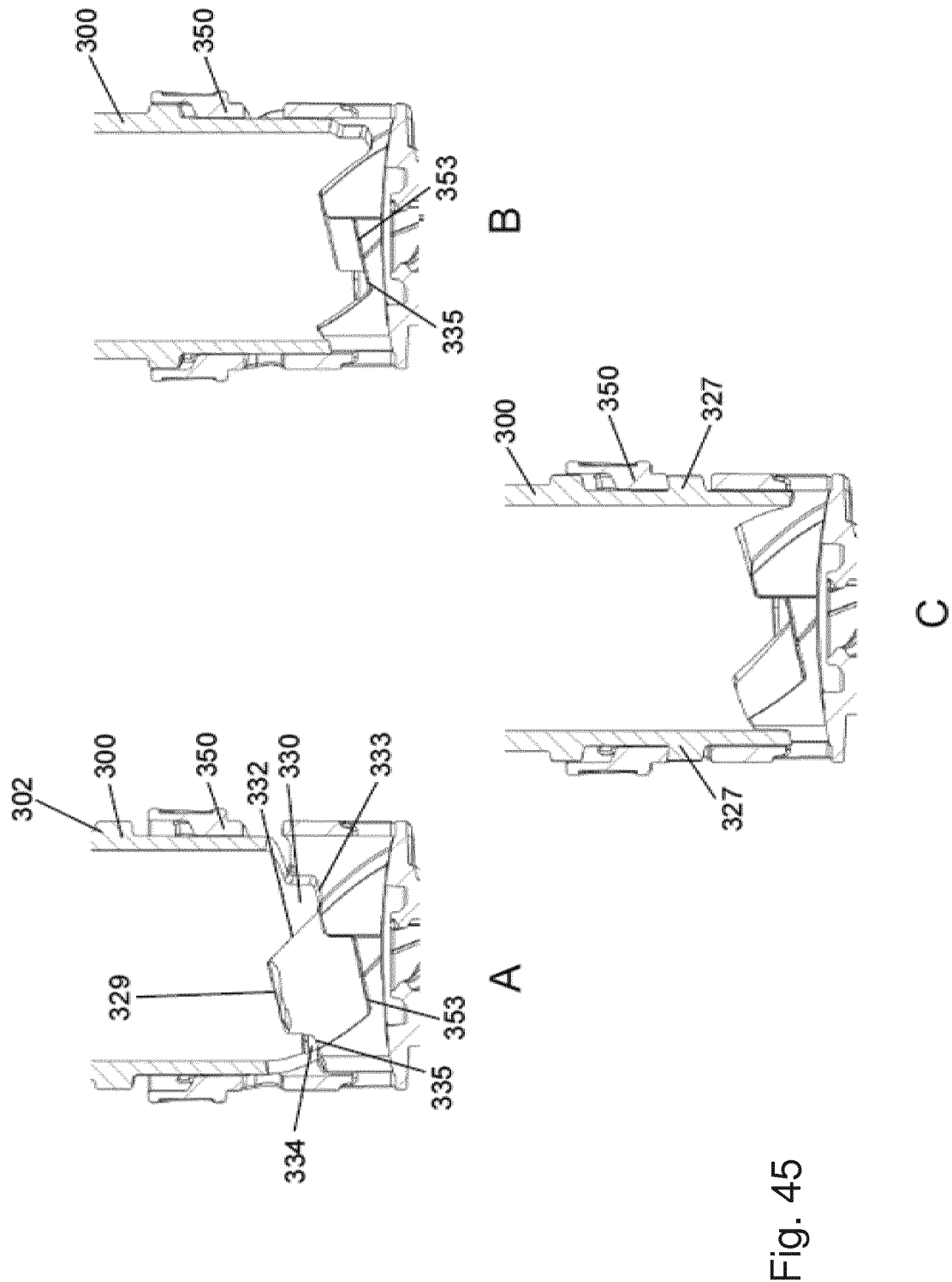

FIG. 45 shows an embodiment of a cartridge unit and a housing with matching ramp or coding structures which utilizes a different ramp or coding structure than the previous embodiment. Again the cartridge unit 300 and the housing are shown in different situations A through C, but only in sectional views as the guiding functionality may be the same. In the following, only the differences to the previously described embodiment are discussed.

A key difference is that the cartridge holder 302 does not comprises a ramp surface or at least not one of significant angular extension which interacts with the ramp surface of the housing during the second stage of movement. Rather, for interaction with the ramp surface 353 in the housing the cartridge holder comprises a ramp interaction feature 334. A proximally facing surface 335 of this feature 334 contacts the ramp surface 353, expediently before the second stage, e.g. at the end of the first stage (situation B). The feature 334 may slide along the ramp surface 353 during the second stage (situation C). At the end of the attachment procedure a surface which delimits the feature 334 in the angular direction, expediently the direction of rotation during the second stage, may angularly abut a feature which delimits the ramp surface 353 in the angular direction. This may provide a robust rotational end stop, in addition or as an alternative to an end stop provided by the guiding interface formed by the guide features 327, 351. The angular extension of the ramp surface 353 may be greater than or, as depicted, equal to the sum of the angular extension of the surface 335 and the angular extension defined by the rotation angle during the second stage along the ramp surface. It should be appreciated that the interaction feature could as well be positioned on the housing and the ramp surface on the cartridge holder. The slopes of the ramp surfaces in the FIG. 45 and FIG. 44 embodiments are equal such that they can generate the second stage axial movement by the distance d. As is immediately apparent the ramp structure in the housing is adjusted to the cartridge holder to provide a matching pair of cartridge unit and housing. The cartridge holder 302 may nevertheless comprise a ramp surface 329, which may abut a feature of the housing during the second stage. Ramp surfaces 329 and 353 may have the same slope as is depicted. If applicable the ramp surface 329 may be sufficient and the ramp surface 353 can be dispensed with.

Therefore, with the same guiding interface but different coding and/or ramp structures it can be prevented that non-matching cartridge holders are attached to a housing, where the ramp surfaces of the ramp structures may effect or generate the axial movement during the second stage.

Figure 46:
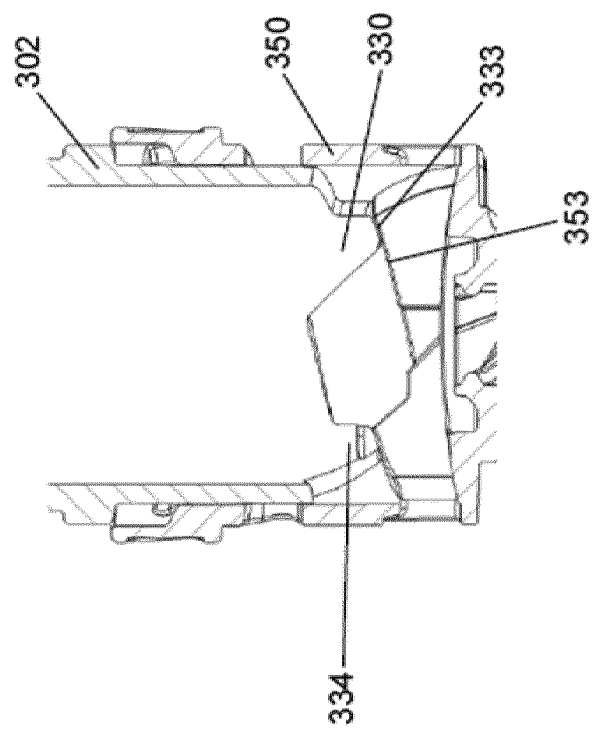

FIG. 46 illustrates that the cartridge holder of FIG. 45 cannot be attached to the housing of FIG. 44. While still in the first stage of movement, the surface 333 of the coding feature 330 abuts the ramp surface 353, e.g. an end section thereof, such as seen in the angular direction of rotation during the first stage. Therefore, further axial and/or rotational movement is prevented and the cartridge holder cannot be attached to the housing. Thus, on account of the different ramp structures which comprise ramp surfaces of equal slopes and the different designs and arrangements of the coding feature(s) attachment of the cartridge holder to the housing is prevented, preferably still during the first stage of movement. This holds although the same guide features 327 and 351 for the bayonet-type connection movement are present in the FIG. 44 and the FIG. 45 embodiments.

Figure 47:
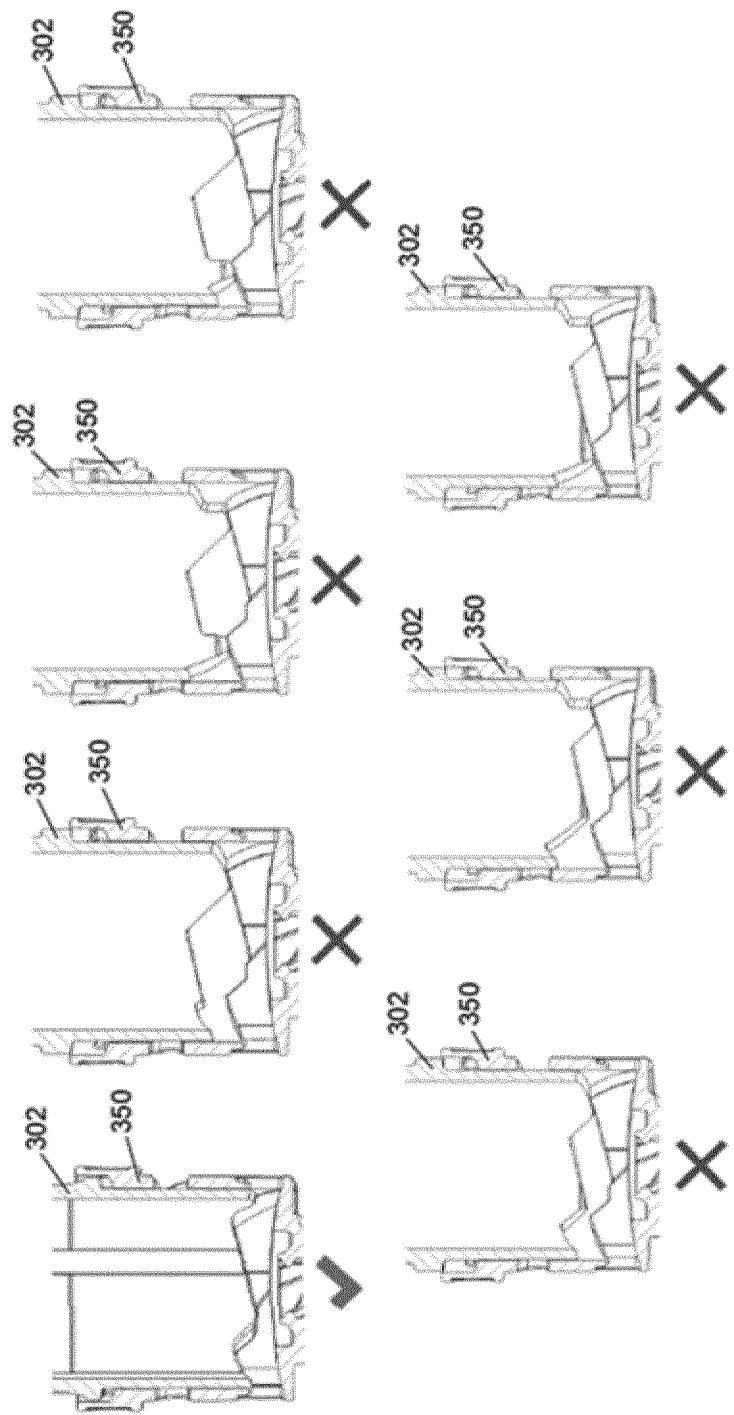

FIG. 47 shows a range of seven different cartridge holders, all of which have ramp or ramp structure geometries. These are all shown in conjunction with the housing or housing part 350 of FIG. 44, i.e. the ramp structure in the housing is always the same. It can be seen that only one of the holders (the same embodiment shown in FIG. 44 and indicated by the hook (tick mark) below the representation of the cartridge holder and the housing) is coded to be compatible with the housing, meaning that only one can be attached to this housing. In the other representation—i.e. the ones highlighted with an "X"—the coding features of the cartridge holder come into contact with the coding features of the housing, e.g. with the ramp surface 353—before the first stage of, e.g. helical, movement is completed. For each of the six non-compatible cartridge holders, a compatible housing component can be created which is in turn not compatible with all of the other cartridge holders. In this way a set of, e.g. up to seven or up to ten, a plurality of coded cartridge holders can be provided; each one being only compatible with a particular housing or drive mechanism. All of the shown systems do have ramp surfaces of the same slope.

Figure 48:
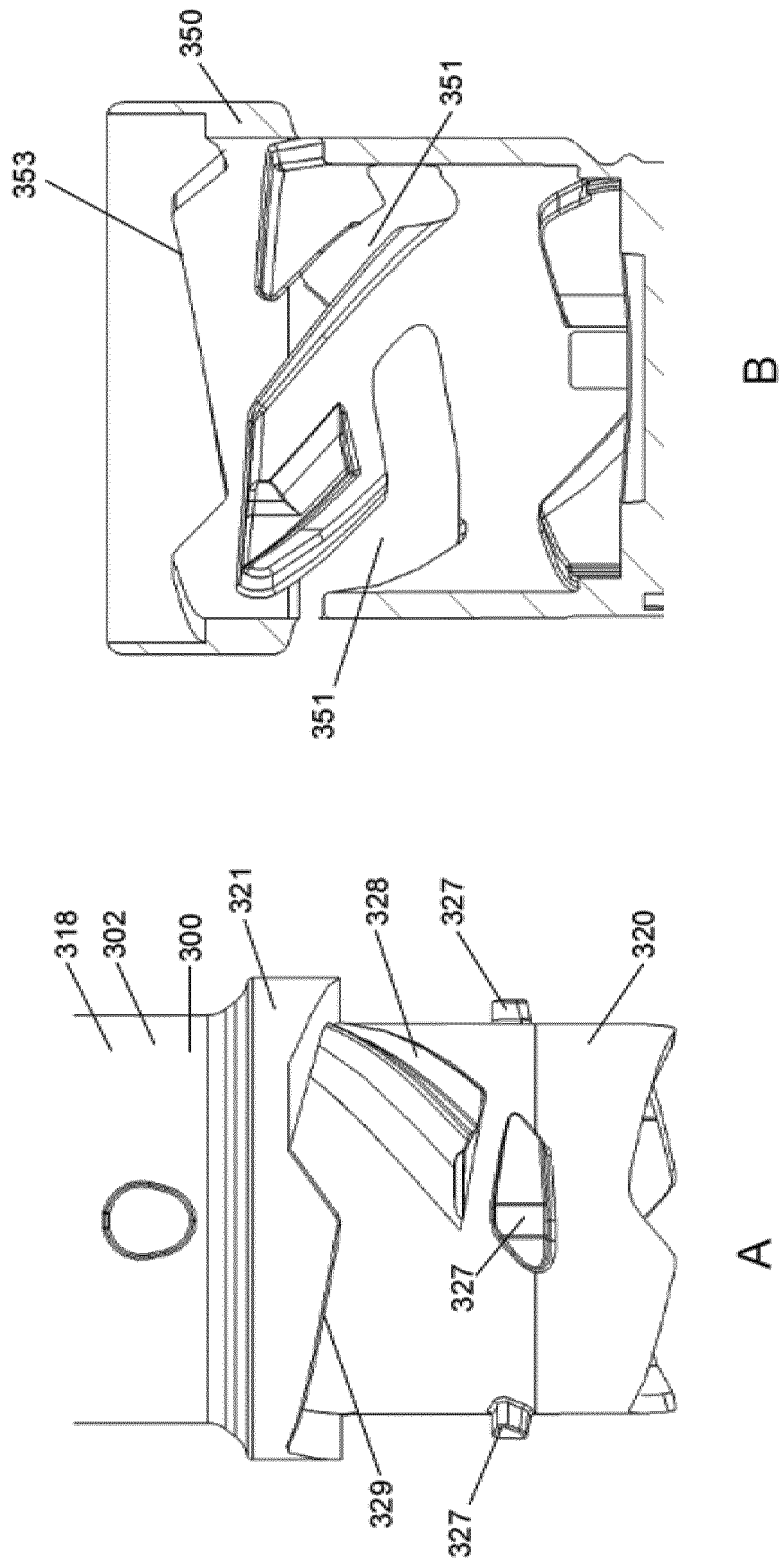

FIG. 48 illustrates another embodiment of a cartridge unit 300 (labelled A) and a housing or housing part (labelled B). The housing or housing part 350 is shown in a sectional view and the cartridge unit is shown in top view. As opposed to the previous embodiments, the ramp structure which provides coding functionality and/or the movement by the second stage axial distance, is not arranged at the proximal end or rim of the cartridge holder. Rather, it is provided on or in the proximally facing surface of the step 321. The step is arranged between the main body region 318 of the cartridge holder 302 and the interface region 320, where the guide features 327 and the securing feature 328 is arranged. Thus, as opposed to the previous embodiment where it was proximally offset, particularly integrated into the proximal rim or edge of the cartridge holder, the ramp structure may be distally offset from guide features 327 and/or the securing feature 328. Further, the corresponding ramp structure in the housing is provided distally offset from the guide features 351. The remaining functionality is the same. As the step may be provided in an already existing device, the ramp structure can be easily implemented on the proximal surface of the step 321.

Figure 49:
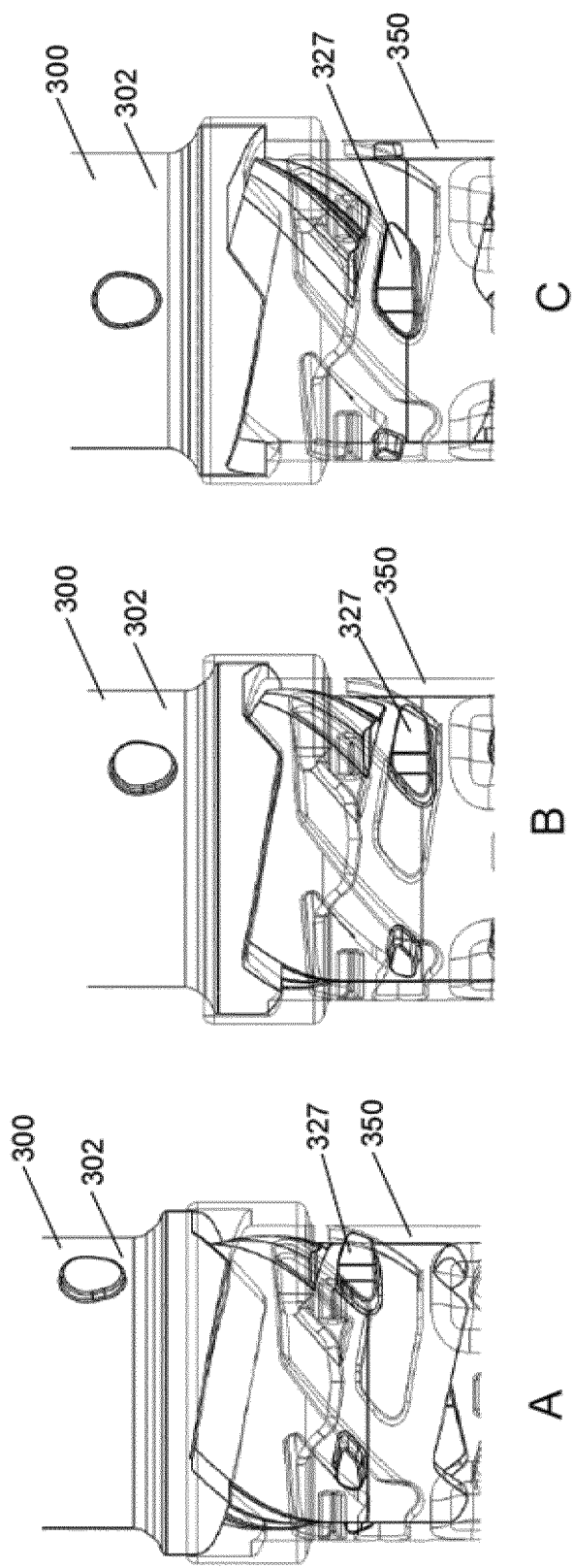

FIG. 49 illustrates the attachment sequence of the cartridge holder 302 and the housing or housing part 350 of FIG. 48 in three different situations (labelled A through C), which correspond to the ones discussed further above. As the ramp structures match one another, the cartridge holder can be attached to the housing. The ramp features or surfaces of the shoulder or step 321 function in the same way as the ones discussed previously. By adjusting the geometry of the ramps of the cartridge holder in the same or in a similar way to that discussed above with reference to FIGS. 44 to 47, a set of coded cartridge holders and housings can be created.

Figure 50:
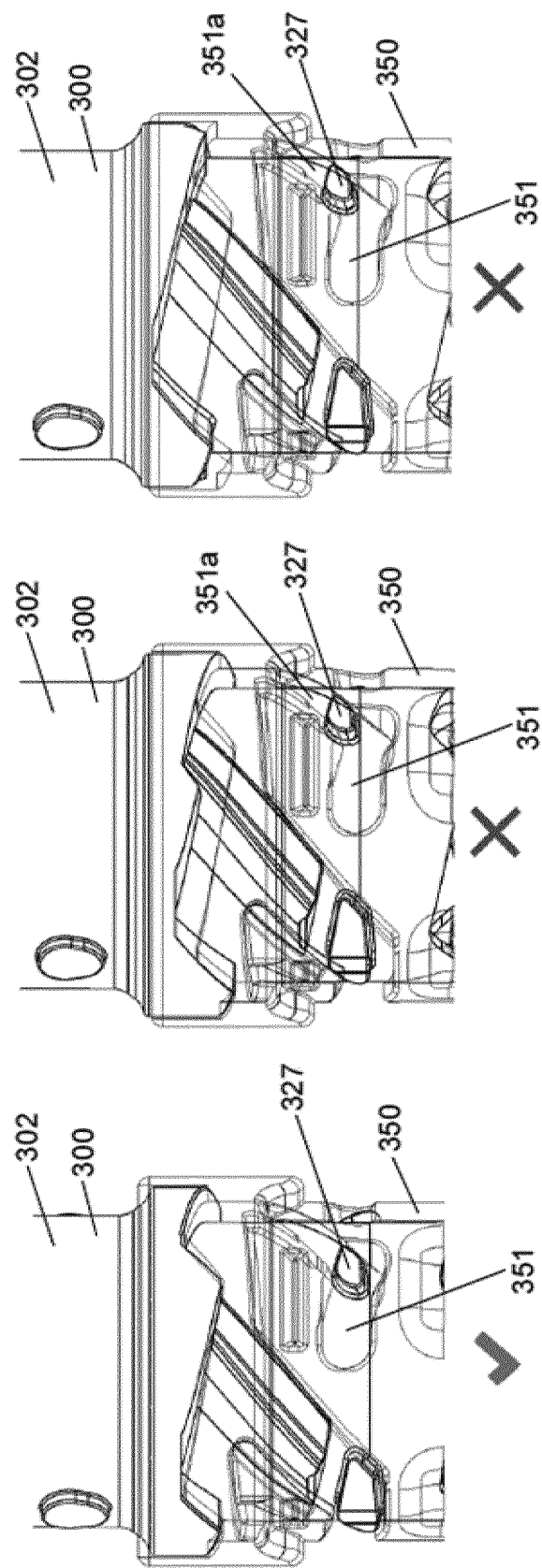

FIG. 50 illustrates three pairs of housings or housing parts 350 and cartridge holders 302, where the housing always has the same ramp structure and the ramp structures of the cartridge holders vary. The pair on the left has matching ramp structures (indicated by the hook or tick mark) and the other ones have not (indicated by the "X"). As is apparent form the two pairs on the right, the axial movement towards the housing is stopped due to the non-matching ramp structures before the second stage of movement can occur, i.e. the guide feature is still in the first section 351a when the further movement is blocked.

By using the coding systems discussed above, it can be ensured that only that type of cartridge unit 300 including the specific drug or medicament, drug formulation, cartridge dimension and/or filling volume, for which the drive mechanism in the housing 10 is designed can be connected to the housing 10.

It should be noted that the coding systems described above utilize the surface profile of a proximally directed surface, e.g. the proximal rim of the cartridge holder, for coding purposes. In mechanisms which do not require that the cartridge holder is moved away from the housing at the end of the connection procedure, a ramp surface with the appropriate dimensioning to achieve this movement does not have to be provided. However, the coding structure may nevertheless comprise ramp structures—but does not have to comprise them—which connect protruding coding features where the angular extension, the axial extension and/or the angular position of the coding features can be varied in order to achieve the appropriate coding functionality.

The coding systems disclosed in conjunction with FIGS. 44 through 50 can be used alternatively or additionally to the coding which may be provided by the bearing 31, piston rod guide section 361 and/or the rigid force transfer body 401 which has been discussed above. Moreover, coding systems, which do rely on the guide features which can be configured differently with respect to angular width and/or positions can be employed instead of having the same arrangements and configuration of guide features for all cartridge units as in the devices as shown in FIGS. 44 through 50.

Aside from the parts or members which are described herein as being adjusted, the remaining parts of the device disclosed in FIGS. 1 through 19 can be interchangeable parts. Thus, the molding tools and also the assembling tools can be re-used.

It should be noted that, although the exemplary embodiments deal with the adjustment or modification of one specific device architecture, the principles disclosed herein can also be applied for other device architectures as well. For example, there are drug delivery devices, where the number sleeve 61 and the dial sleeve 62 do move independently and/or relative to one another during dose setting and/or dose delivery. Moreover, the present disclosure should not be regarded as being restricted to reusable drug delivery devices, although in such devices, the presently disclosed concepts are particularly useful. However, using interchangeable parts and non-interchangeable parts in drug delivery devices may also be advantageous for disposable drug delivery devices.

The disclosed concepts do also provide a system or arrangement of drug delivery devices with cartridges of different dimensions, drugs and/or or drug formulations where the devices may have the same or equivalent outer dimensions, even though the cartridges may have different dimensions such as different length, outer and/or inner diameters.

It should be appreciated that at least most of the disclosed concepts if not all of them do also apply to drug delivery devices which have cartridges of the same dimensions or volumes but with different liquids.

If the cartridges have the same dimension and/or filling level but liquids with different drugs or drug concentrations, e.g. one has three times the drug as the other one, the following elements of the dose setting and drive mechanism may have to be modified:
  the piston rod 30, e.g. one or more of the threads;
  the drive member 40, e.g. the distal part thereof which interacts with the tracking member;
  the tracking member 50;
  the number sleeve 61, in particular with respect to the size, distribution and/or arrangement of the dose numbers.

A modification in the cartridge bias system is, of course, not necessary as the dimensions may be the same for the modified and the non-modified devices.

The changes which are suitable for the respective member will become apparent from the description given further above for the adaptions to the different cartridge dimensions.

Alternatively or additionally, the concepts discussed above—aside from the coding concepts—may also apply for devices, in particular disposable ones which are disposed of after the maximum amount of liquid has been dispensed from the cartridge, with a unitary housing wherein the cartridge is retained or with a cartridge holder which is permanently secured to the housing.

The scope of protection is not limited to the examples given herein above. Any invention disclosed herein is embodied in each novel characteristic and each combination of characteristics, which particularly includes every combination of any features which are stated in the claims, even if this feature or this combination of features is not explicitly stated in the claims or in the examples.

REFERENCE NUMERALS 1 drug delivery device
10 outer housing part
11 distal part
12 rotational hard stop/stop features/second rotational stop
13 aperture
20 inner body/housing
21 external thread
22 splines
23 bayonet features
24 window retention nose/retaining means
25 stop faces/first rotational stop
30 piston rod
31 bearing
32 external thread/first outer thread
33 external thread/second outer thread
34 portion
35 fixing feature
36 fixing portion
37 line
38 line
39 blocking feature
40 driver
41 distal driver part/distal portion/first component
42 proximal driver part/proximal portion/second component
43 coupler
44 external thread/helical groove
45 stop faces
46 splines
47 teeth features
48 fingers/flexible arms
49 bearing surface
50 dose nut
51 stop faces
52 external ribs
53 internal thread
60 display member
61 number sleeve/first component
62 dial sleeve/other component
63 stop face
64 helical drive face/protruding thread
65 clutch features/teeth
66 bearing face/flange/contact features
67 opposite faces
68 ratchet arm/dispense clicker/clicker feature
70 button
71 ratchet teeth/dispense clicker/clicker teeth
72 end face
73 arms/fingers
74 snap features
80 cartridge holder
81 cartridge
82 bayonet connection
83 aperture
84 distal end
90 clutch
91 drive sleeve splines
92 clutch biasing teeth
93 snap apertures/snap features
94 splines
95 clutch teeth
100 clicker
101 distal clicker part/second toothed element
102 proximal clicker part/first toothed element
103 spring
104 splines
105 clicker teeth
106 clicker teeth
107 external splines
108 shaped splines
109 clutch biasing teeth
110 spring
120 cap
230 window
300 cartridge assembly
301 cartridge
302 cartridge holder
303 cartridge retaining section
304 inner wall
305 opening
306 dispensing end
307 drug
308 septum
309 septum retainer
310 head portion
311 main body portion
312 neck portion
313 cartridge surface
314 shoulder surface
315 distal end wall
316 opening
317 distal region
318 main body region
319 needle connector
320 connection region
321 step
322 fixing feature
323 injection gate mark
324 fixing surface
325 opening
326 surface/cartridge guiding feature
327 guide feature
328 securing feature
329 ramp surface
330 coding feature
331 shoulder region
332 surface
333 surface
334 ramp interaction feature
335 surface
340 cartridge body
341 reinforcement section
342 cartridge support feature
350 housing part
351 guide feature
351a,b section
352 distal end
353 ramp surface
360 bung
361 piston rod guide section
362 hollow 363 opening
364 connection feature
365 opening
366 thread
366' thread
367 section
368 section
369 region
400 cartridge bias system
401 rigid force transfer body
402 first resilient member
403 second resilient member
404 cartridge contact area
405 housing contact area
406 load transfer surface
407 load transfer surface
408 connection feature
409 recess
410 guide feature
411 body structure
412 connection
413 cartridge contact feature
414 flexible arm
415 connection feature/guide feature
A thickness
B distance
R$_1$ region
R$_2$ region
X axis

The invention claimed is:

1. An arrangement of drug delivery devices, the arrangement comprising a first drug delivery device and a second drug delivery device,
wherein the first drug delivery device comprises:
a first housing having a proximal end and a distal end;
a first cartridge unit releasably or permanently connected to the first housing or retained in the first housing;
the first cartridge unit comprising or provided to retain a first cartridge containing a first liquid, wherein the first cartridge comprises a first bung and a first cartridge body, the first bung being movable in the distal direction relative to the first cartridge body to dispense the first liquid from the first cartridge; and
a first dose setting and drive mechanism which is at least partly arranged in the first housing, the first dose setting and drive mechanism comprising a plurality of first mechanism members which are movable relative to the first housing and/or relative to one another during a dose setting operation and/or a dose delivery operation,
wherein the second drug delivery device comprises:
a second housing having a proximal end and a distal end;
a second cartridge unit releasably or permanently connected to the second housing or retained in the second housing;
the second cartridge unit comprising a second cartridge containing a second liquid, wherein the second cartridge comprises a second bung and a second cartridge body, the second bung being movable in the distal direction relative to the second cartridge body to dispense the second liquid from the second cartridge; and
a second dose setting and drive mechanism which is at least partly arranged in the second housing, the second dose setting and drive mechanism comprising a plurality of second mechanism members which are movable relative to the second housing and/or relative to one another during a dose setting operation and/or a dose delivery operation,
wherein the first liquid and the second liquid are different, and wherein
the first mechanism members and the second mechanism members each comprise at least one interchangeable mechanism member configured to assemble both the first dose setting and drive mechanism and the second dose setting and drive mechanism,
the first mechanism members and the second mechanism members each comprise at least one non-interchangeable mechanism member, and
the first cartridge and the second cartridge have different dimensions.

2. The arrangement of claim 1, wherein the first mechanism members and the second mechanism members comprise a plurality of interchangeable mechanism members and a plurality of non-interchangeable mechanism members, wherein the number of interchangeable mechanism members is greater than the number of non-interchangeable mechanism members.

3. The arrangement of claim 1, wherein the first mechanism members comprise two or more of the following members or types of members:
a first piston rod arranged to drive movement of the first bung during the dose delivery operation;
a first bung interface member coupled to the first piston rod and configured to abut the first bung;
a first drive member operatively coupled to the first piston rod to transfer a driving force to the first piston rod;
a first dose setting member which is movable relative to the first housing to set the size of a dose of first liquid to be delivered from the first cartridge;
a first user interface member which is operable by the user for performing the dose setting operation and/or the dose delivery operation;
a first tracking member coupleable or coupled to a first tracking member path, wherein the position of the first tracking member along the first tracking member path is indicative for the volume of the first liquid remaining in the first cartridge and/or having been dispensed from the first cartridge;
a first dose indication member configured to indicate the size of the set dose;
a first dosing clutch member configured to couple two first mechanism members during only one of the dose setting operation and the dose delivery operation;
a first reset clutch member configured to couple two first mechanism members during the dose setting operation and the dose delivery operation; or
a first clicker member provided to generate an audible and/or tactile feedback during the dose setting operation and/or the dose delivery operation, and
wherein the second mechanism members comprise two or more of the following members or types of members:
a second piston rod arranged to drive movement of the second bung during the dose delivery operation;
a second bung interface member coupled to the second piston rod and configured to abut the second bung;
a second drive member operatively coupled to the second piston rod to transfer a driving force to the second piston rod;
a second dose setting member which is movable relative to the second housing to set the size of a dose of second liquid to be delivered from the second cartridge;

a second user interface member which is operable by the user for performing the dose setting operation and/or the dose delivery operation;
a second tracking member coupleable or coupled to a second tracking member path, wherein the position of the second tracking member along the second tracking member path is indicative for the volume of the second liquid remaining in the second cartridge and/or having been dispensed from the second cartridge;
a second dose indication member configured to indicate the size of the set dose;
a second dosing clutch member configured to couple two second mechanism members during only one of the dose setting operation and the dose delivery operation;
a second reset clutch member configured to couple two second mechanism members during the dose setting operation and the dose delivery operation; or
a second clicker member provided to generate an audible and/or tactile feedback during the dose setting operation and/or the dose delivery operation.

4. The arrangement of claim 3, wherein the first dose setting and drive mechanism and the second dose setting and drive mechanism consist of first mechanism members and second mechanism members of mutually corresponding types of members.

5. The arrangement of claim 3,
wherein the following members are non-interchangeable mechanism members:
the first and second piston rod; and
the first and second drive member.

6. The arrangement of claim 3, wherein the second piston rod has one or more blocking features which are arranged to block movement of the second piston rod in the distal direction relative to the first cartridge body.

7. The arrangement of claim 3, wherein the following members are interchangeable mechanism members:
the first and second user interface member; and
the first and second dose indication member.

8. The arrangement of claim 1, wherein the first drug delivery device and the second drug delivery device have equivalent outer dimensions and/or outer shape.

9. The arrangement of claim 1, wherein the first cartridge body is shorter than the second cartridge body and has a smaller diameter than the second cartridge body, and wherein the first liquid and the second liquid comprise different drugs or different drug formulations.

10. The arrangement of claim 1,
wherein the first housing comprises a plurality of first housing parts which are assembled to one another and wherein the second housing comprises a plurality of second housing parts which are assembled to one another, and
wherein one of the second housing parts and one of the first housing parts are interchangeable parts and another one of the second housing parts and another one of the first housing parts are non-interchangeable parts.

11. The arrangement of claim 1,
wherein the first drug delivery device comprises a first cartridge bias system which comprises at least one first resilient member, wherein the first cartridge bias system is configured to exert a force on the first cartridge to maintain the first cartridge in a defined position, wherein the force is provided by the at least one first resilient member, and
wherein the second drug delivery device comprises a second cartridge bias system which comprises at least one second resilient member, wherein the second cartridge bias system is configured to exert a force on the second cartridge to maintain the second cartridge in a defined position, wherein the force is provided by the at least one second resilient member, and
wherein the first cartridge bias system comprises a rigid body as spacer to compensate the difference in dimension between the first cartridge and the second cartridge.

12. The arrangement of claim 11,
wherein the at least one first resilient member and the at least one second resilient member are interchangeable parts and/or wherein the rigid body is a non-interchangeable part.

13. The arrangement of claim 11, wherein the second cartridge unit and the first housing are adjusted such that the second cartridge abuts the first housing and/or the rigid body of the first cartridge bias system to prevent connection of the second cartridge unit to the first housing.

14. The arrangement of claim 1,
wherein the first cartridge unit comprises a first cartridge holder, wherein the first cartridge is permanently secured within the first cartridge holder and wherein the first cartridge holder is releasably secured to the first housing, and
wherein the second cartridge unit comprises a second cartridge holder, wherein the second cartridge is permanently secured within the second cartridge holder and wherein the second cartridge holder is releasably secured to the second housing.

15. The arrangement of claim 1, wherein a first mechanism unit comprises the first housing and the first dose setting and drive mechanism and a second mechanism unit comprises the second housing and the second dose setting and drive mechanism, wherein the first mechanism unit, the first cartridge unit, the second mechanism unit, and the second cartridge unit are adjusted to one another such that the first cartridge unit cannot be connected to the second mechanism unit and/or the second cartridge unit cannot be connected to the first mechanism unit,
wherein the first housing and the second cartridge unit have matching guide features which could form a guiding interface to guide movement of the second cartridge unit relative to the first housing to a relative position, where the first housing and the second cartridge unit are connected, and
wherein the second housing and the first cartridge unit have matching guide features which could form a guiding interface to guide movement of the first cartridge unit relative to the second housing to a relative position, where the second housing and the first cartridge unit are connected.

16. The arrangement of claim 15, wherein the first cartridge holder has a first cartridge coding structure and the second mechanism unit has a second mechanism coding structure, wherein the coding structures are adjusted to prevent relative movement of the first cartridge holder towards the second housing before the first cartridge unit is connected to the second housing.

17. The arrangement of claim 14, wherein, when the first cartridge holder is connected to the first housing, a first portion of the first cartridge holder protrudes from the first housing, and wherein, when the second cartridge holder is connected to the second housing, a second portion of the second cartridge holder protrudes from the second housing, wherein the length of the first portion of the first cartridge holder which protrudes from the first housing and the length of the second portion of the second cartridge holder which protrudes from the second housing are identical or substantially identical.

18. The arrangement of claim 1, wherein the first mechanism members comprise all of the following members or types of members:
a first piston rod arranged to drive movement of the first bung during the dose delivery operation;
a first bung interface member coupled to the first piston rod and configured to abut the first bung;
a first drive member operatively coupled to the first piston rod to transfer a driving force to the first piston rod;
a first dose setting member which is movable relative to the first housing to set the size of a dose of first liquid to be delivered from the first cartridge;
a first user interface member which is operable by the user for performing the dose setting operation and/or the dose delivery operation;
a first tracking member coupleable or coupled to a first tracking member path, wherein the position of the first tracking member along the first tracking member path is indicative for the volume of first liquid remaining in the first cartridge and/or having been dispensed from the first cartridge;
a first dose indication member configured to indicate the size of the set dose;
a first dosing clutch member configured to couple two first mechanism members during only one of the dose setting operation and the dose delivery operation;
a first reset clutch member configured to couple two first mechanism members during the dose setting operation and the dose delivery operation; or
a first clicker member provided to generate an audible and/or tactile feedback during the dose setting operation and/or the dose delivery operation, and
wherein the second mechanism members comprise all of the following members or types of members:
a second piston rod arranged to drive movement of the second bung during the dose delivery operation;
a second bung interface member coupled to the second piston rod and configured to abut the second bung;
a second drive member operatively coupled to the second piston rod to transfer a driving force to the second piston rod;
a second dose setting member which is movable relative to the second housing to set the size of a dose of second liquid to be delivered from the second cartridge;
a second user interface member which is operable by the user for performing the dose setting operation and/or the dose delivery operation;
a second tracking member coupleable or coupled to a second tracking member path, wherein the position of the second tracking member along the second tracking member path is indicative for the volume of second liquid remaining in the second cartridge and/or having been dispensed from the second cartridge;
a second dose indication member configured to indicate the size of the set dose;
a second dosing clutch member configured to couple two second mechanism members during only one of the dose setting operation and the dose delivery operation;
a second reset clutch member configured to couple two second mechanism members during the dose setting operation and the dose delivery operation; or
a second clicker member provided to generate an audible and/or tactile feedback during the dose setting operation and/or the dose delivery operation.

19. The arrangement of claim 18,
wherein the following members are non-interchangeable mechanism members:
the first and second piston rod;
the first and second bung interface member;
the first and second drive member; and
the first and second tracking member, and
wherein the following members are interchangeable mechanism members:
the first and second user interface member;
the first and second dose indication member;
the first and second dosing clutch member;
the first and second reset clutch member; and
the first and second clicker member.

20. The arrangement of claim 5,
wherein the following members are non-interchangeable mechanism members:
the first and second bung interface member; and
the first and second tracking member.

21. The arrangement of claim 7,
wherein the following members are interchangeable mechanism members:
the first and second dosing clutch member;
the first and second reset clutch member; and
the first and second clicker member.

22. A method of operating a first drug delivery to deliver a first liquid and/or a second drug delivery device to deliver a second liquid,
wherein the first drug delivery device comprises:
a first housing having a proximal end and a distal end;
a first cartridge unit releasably or permanently connected to the first housing or retained in the first housing;
the first cartridge unit comprising or provided to retain a first cartridge containing the first liquid, wherein the first cartridge comprises a first bung and a first cartridge body, the first bung being movable in the distal direction relative to the first cartridge body to dispense the first liquid from the first cartridge; and
a first dose setting and drive mechanism which is at least partly arranged in the first housing, the first dose setting and drive mechanism comprising a plurality of first mechanism members which are movable relative to the first housing and/or relative to one another during a dose setting operation and/or a dose delivery operation,
wherein the second drug delivery device comprises:
a second housing having a proximal end and a distal end;
a second cartridge unit releasably or permanently connected to the second housing or retained in the second housing;
the second cartridge unit comprising a second cartridge containing the second liquid, wherein the second cartridge comprises a second bung and a second cartridge body, the second bung being movable in the distal direction relative to the second cartridge body to dispense the second liquid from the second cartridge; and
a second dose setting and drive mechanism which is at least partly arranged in the second housing, the second dose setting and drive mechanism comprising a plurality of second mechanism members which are movable relative to the second housing and/or relative to one another during a dose setting operation and/or a dose delivery operation,
wherein:

the first liquid and the second liquid are different, the first mechanism members and the second mechanism members each comprise at least one interchangeable mechanism member configured to assemble both the first dose setting and drive mechanism and the second dose setting and drive mechanism, the first mechanism members and the second mechanism members each comprise at least one non-interchangeable mechanism member, and the first cartridge and the second cartridge have different dimensions, and wherein the method comprises:

moving the first bung in the distal direction relative to the first cartridge body to dispense the first liquid from the first cartridge, or moving the second bung in the distal direction relative to the second cartridge body to dispense the second liquid from the second cartridge.

23. A method of producing a first mechanism unit which is configured to be connected to a first cartridge unit to form a first drug delivery device, the method comprising:

providing a second mechanism unit as a model for the first mechanism unit, the second mechanism unit being configured to be connected to a second cartridge unit which is different from the first cartridge unit, wherein the second mechanism unit comprises a second housing and a second dose setting and drive mechanism which is at least partly arranged in the second housing, the second dose setting and drive mechanism comprising a plurality of second mechanism members which are movable relative to the second housing and/or relative to one another during a dose setting operation for setting a dose of a second liquid and/or a dose delivery operation for delivering the set dose;

providing a first housing for the first mechanism unit;

producing one interchangeable mechanism member in accordance with one of the second mechanism members;

producing one non-interchangeable mechanism member which is adjusted to the first cartridge unit; and assembling a first dose setting and drive mechanism for the first mechanism unit, the first dose setting and drive mechanism comprising the interchangeable mechanism member and the non-interchangeable mechanism member, and arranging the interchangeable mechanism member and the non-interchangeable mechanism member in the first housing, wherein the first cartridge unit is provided to retain a first cartridge containing a first liquid and wherein the second cartridge unit is provided to retain a second cartridge containing the second liquid, wherein the first cartridge and the second cartridge have different dimensions, and wherein the first liquid and the second liquid are different.

* * * * *